US012663414B2

(12) United States Patent
Ho et al.

(10) Patent No.: US 12,663,414 B2
(45) Date of Patent: Jun. 23, 2026

(54) PLATFORM FOR CO-CULTURE IMAGING TO CHARACTERIZE IN VITRO EFFICACY OF HETEROTYPIC EFFECTOR CELLULAR THERAPIES IN CANCER

(71) Applicant: TEMPUS AI, INC., Chicago, IL (US)

(72) Inventors: Chi-Sing Ho, Redwood City, CA (US); Madhavi Kannan, Bloomington, IL (US); Sonal Khare, Chicago, IL (US); Brian Larsen, Chicago, IL (US); Brandon Mapes, Chicago, IL (US); Ameen Salahudeen, Oak Park, IL (US); Jagadish Venkataraman, Menlo Park, CA (US)

(73) Assignee: TEMPUS AI, INC., Chicago, IL (US)

( * ) Notice: Subject to any disclaimer, the term of this patent is extended or adjusted under 35 U.S.C. 154(b) by 452 days.

(21) Appl. No.: 17/816,395

(22) Filed: Jul. 29, 2022

(65) Prior Publication Data

US 2023/0036156 A1     Feb. 2, 2023

Related U.S. Application Data

(60) Provisional application No. 63/263,761, filed on Nov. 8, 2021, provisional application No. 63/227,877, filed
(Continued)

(51) Int. Cl.
*G01N 33/50*     (2006.01)
*G01N 21/64*     (2006.01)
(Continued)

(52) U.S. Cl.
CPC ..... *G01N 33/5082* (2013.01); *G01N 21/6428* (2013.01); *G01N 21/6456* (2013.01);
(Continued)

(58) Field of Classification Search
CPC ........... G01N 33/5082; G01N 21/6428; G01N 21/6456; G01N 33/5011;
(Continued)

(56) References Cited

U.S. PATENT DOCUMENTS 10,395,772 B1     8/2019   Lucas et al.
10,746,736 B2 *   8/2020   Varadarajan ..... G01N 33/56966
(Continued)

FOREIGN PATENT DOCUMENTS

WO     2020/142563 A1     7/2020
WO     2020/168008 A1     8/2020
(Continued)

OTHER PUBLICATIONS

Larsen B, Kannan M et al. A pan-cancer organoid platform for precision medicine. Cell Rep. Jul. 27, 2021;36(4):109429. doi: 10.1016/j.celrep.2021.109429. PMID: 34320344. (Year: 2021).*
(Continued)

*Primary Examiner* — Stephen R Koziol
*Assistant Examiner* — Joshua Chen
(74) *Attorney, Agent, or Firm* — MARSHALL, GERSTEIN & BORUN LLP

(57)     ABSTRACT

A method for characterizing cancer organoid response to an immune cell based therapy, includes providing a panel of different combinations of cancer organoid cells and immune cells to culturing wells and culturing the different combination under conditions that support organoid growth. Bright-field and corresponding fluorescence images of the culturing wells are captured and provided to one or more trained machine learning algorithms that identify and distinguish cancer organoid cells from immune cells and characterize cancer organoid morphology changes caused by an immune cell based therapies, from which an analytical report includ-
(Continued)

ing a characterization of cancer organoid cell death caused by the immune cell based therapy is provided.

38 Claims, 31 Drawing Sheets
(23 of 31 Drawing Sheet(s) Filed in Color)

Related U.S. Application Data on Jul. 30, 2021, provisional application No. 63/203, 749, filed on Jul. 29, 2021.

(51) Int. Cl.

| | |
|---|---|
| *G06T 3/06* | (2024.01) |
| *G06T 7/00* | (2017.01) |
| *G06T 7/11* | (2017.01) |
| *G06V 10/774* | (2022.01) |
| *G06V 20/69* | (2022.01) |
| *G16H 15/00* | (2018.01) |
| *G16H 30/40* | (2018.01) |

(52) U.S. Cl.
CPC ............ *G01N 33/5011* (2013.01); *G06T 3/06* (2024.01); *G06T 7/0016* (2013.01); *G06T 7/11* (2017.01); *G06V 10/774* (2022.01); *G06V 20/695* (2022.01); *G06V 20/698* (2022.01); *G16H 15/00* (2018.01); *G16H 30/40* (2018.01); *G01N 2021/6439* (2013.01); *G06T 2200/04* (2013.01); *G06T 2207/10064* (2013.01); *G06T 2207/20081* (2013.01); *G06T 2207/30024* (2013.01); *G06T 2207/30072* (2013.01)

(58) Field of Classification Search
CPC . G01N 2021/6439; G06T 3/06; G06T 7/0016; G06T 7/11; G06T 2200/04; G06T 2207/10064; G06T 2207/20081; G06T 2207/30024; G06T 2207/30072; G06T 2207/20084; G06T 7/12; G06T 2207/10016; G06T 2207/10024; G06T 2207/10056; G06T 2207/30096; G06V 10/774; G06V 20/695; G06V 20/698; G06V 10/82; G06V 20/69; G16H 15/00; G16H 30/40; G16H 20/10; G16H 50/20; G16H 50/70
See application file for complete search history.

(56) References Cited

U.S. PATENT DOCUMENTS

| | | | |
|---|---|---|---|
| 10,902,952 B2 | 1/2021 | Lucas et al. | |
| 10,957,041 B2 | 3/2021 | Yip et al. | |
| 10,975,445 B2 | 4/2021 | Venkat et al. | |
| 11,043,283 B1 | 6/2021 | Bell et al. | |
| 11,043,304 B2 | 6/2021 | Lozac'Hmeur et al. | |
| 11,081,210 B2 | 8/2021 | Perera | |
| 11,211,144 B2 | 12/2021 | Zhu et al. | |
| 11,211,147 B2 | 12/2021 | Finkle et al. | |
| 11,414,700 B2 | 8/2022 | Perera et al. | |
| 11,415,571 B2 | 8/2022 | Larsen et al. | |
| 11,422,355 B2* | 8/2022 | Jackson ............. | G01N 21/6428 |
| 11,475,981 B2 | 10/2022 | Tell et al. | |
| 11,610,307 B2* | 3/2023 | Yip .......................... | G06T 1/20 |
| 12,241,830 B2* | 3/2025 | Boehm ............. | G01N 33/5026 |
| 2020/0075169 A1 | 3/2020 | Lau et al. | |
| 2020/0098448 A1 | 3/2020 | Shah et al. | |
| 2020/0118644 A1 | 4/2020 | Khan et al. | |
| 2020/0135303 A1 | 4/2020 | Barber | |
| 2020/0210852 A1 | 7/2020 | Igartua et al. | |
| 2020/0211716 A1 | 7/2020 | Lefkofsky et al. | |

| | | | |
|---|---|---|---|
| 2020/0258601 A1 | 8/2020 | Lau | |
| 2020/0335102 A1 | 10/2020 | Lefkofsky et al. | |
| 2020/0365232 A1 | 11/2020 | Jaros et al. | |
| 2020/0365268 A1 | 11/2020 | Michuda et al. | |
| 2020/0381087 A1 | 12/2020 | Ozeran et al. | |
| 2020/0395097 A1 | 12/2020 | Chang et al. | |
| 2021/0057042 A1 | 2/2021 | Beaubier et al. | |
| 2021/0057071 A1 | 2/2021 | Barber et al. | |
| 2021/0090694 A1 | 3/2021 | Colley et al. | |
| 2021/0098078 A1 | 4/2021 | Lozac'Hmeur et al. | |
| 2021/0115511 A1 | 4/2021 | Blidner | |
| 2021/0118526 A1 | 4/2021 | Barber | |
| 2021/0118559 A1 | 4/2021 | Lefkofsky | |
| 2021/0151192 A1 | 5/2021 | Lucas et al. | |
| 2021/0155989 A1 | 5/2021 | Salahudeen et al. | |
| 2021/0172931 A1* | 6/2021 | Larsen .............. | G01N 33/5005 |
| 2021/0269878 A1 | 9/2021 | Blidner | |
| 2021/0325308 A1 | 10/2021 | Kannan et al. | |
| 2021/0398617 A1 | 12/2021 | Finkle et al. | |
| 2021/0407080 A1* | 12/2021 | Szu ........................ | G16H 10/40 |
| 2022/0341914 A1 | 10/2022 | Larsen et al. | |
| 2023/0289968 A1* | 9/2023 | Martinelli ............... | G06T 7/254 |
| 2024/0029409 A1* | 1/2024 | Aidt ....................... | G06V 10/22 |
| 2024/0168016 A1* | 5/2024 | Cai ...................... | G01N 33/582 |
| 2024/0272161 A1* | 8/2024 | Taube ..................... | A61P 35/04 |

FOREIGN PATENT DOCUMENTS

| | | |
|---|---|---|
| WO | 2020/198380 A1 | 10/2020 |
| WO | 2021/081253 A1 | 4/2021 |
| WO | 2021/113821 A1 | 6/2021 |
| WO | 2021/113846 A1 | 6/2021 |
| WO | 2021/168143 A1 | 8/2021 |

OTHER PUBLICATIONS

Bar-Ephraim et al., Organoids in immunological research, Nat. Rev. Immunol., 20(5):279-293 (2020).

Berryman et al., Image-based Cell Phenotyping Using Deep Learning, Communications Biology, 22: (2020).

Borten et al.,Automated brightfield morphometry of 3D organoid populations by OrganoSeg. Scientific Reports, 8:5319: (2018).

Cancian et al., Development of a Deep-Learning Pipeline to Recognize and Characterize Macrophages in Colo-Rectal Liver Metastasis, Cancers, 13(3313):10 (2021).

Cepa., Segmentation of Total Cell Area in Brightfield Microscopy Images, Methods and Protocols, 1(43):8 (2018).

Daoust., Image Classification., TensorFlow Documentation., Web. Jan. 7, 2021; 10 pages.

International Application No. PCT/US22/038960, International Search Report and Written Opinion, mailed Nov. 1, 2022.

Kepp et al., A fluorescent biosensor-based platform for the discovery of immunogenic cancer cell death inducers, Oncoimmunology, 8(8):e1606665 (2019).

Larsen et al., A pan-cancer organoid platform for precision medicine, Cell Reports, 36(4):109429 (2021).

Mencattini et al., Discovering the hidden messages within cell trajectories using a deep learning approach for in vitro evalualion of cancer drug treatmertts, Scientific Reports, 10:7653 (2020).

Neal et al., Organoid modeling of the tumor immune microenvironment, Cell, 40: (2018).

Noller et al., A Practical Approach to Quantitative Processing and Analysis of Small Biological Structures by Fluorescent Imaging, J Biomol Tech, 27(3):90-97 (2016).

Piccinini et al., Software tools for 3D nuclei segmentation and quantitative analysis in multicellular, aggregates Computational and Structural Biotechnology Journal, 18:1287-1300 (2020).

Scanlan et al., Cancer/testis antigens: an expanding family of targets for cancer immunotherapy, Immunol. Rev., 188:22-32 (2002).

Takuoka et al., 3D convolutional neural networks-based segmentation to acquire quantitative criteria of the nucleus during mouse embryogenesis, Systems Biology and Application, 6(32):12 (2020).

Wu et al., RCNN-SliceNet: A Slice and Cluster Approach for Nuclei Centroid Detection in Three-Dimensional Fluorescence Microscopy Images, arXIV, 11: (2021).

(56) References Cited

OTHER PUBLICATIONS

Zhou et al., Self Pre-training with Masked Autoencoders for Medical Image Analysis. arXiv, 12: (2022).

Zhuge et al., Deep learning 2D and 3D optical sectioning microscopy using cross-modality Pix2Pix Cgan image translation, Biomedical Optics Express, 12(12):18 (2021).

Bhinder et al., Artificial Intelligence in Cancer Research and Precision Medicine, Cancer Discovery, 11(4):900-915 (Apr. 2021).

European Application No. 22850400.7, European Search Report and Written Opinion, mailed Apr. 14, 2025.

Xing et al., Robust Nucleus/Cell Detection and Segmentation in Digital Pathology and Microscopy Images: A Comprehensive Review, IEEE Reviews in Biomedical Engineering, 9:234-263 (Jan. 2016).

* cited by examiner

700

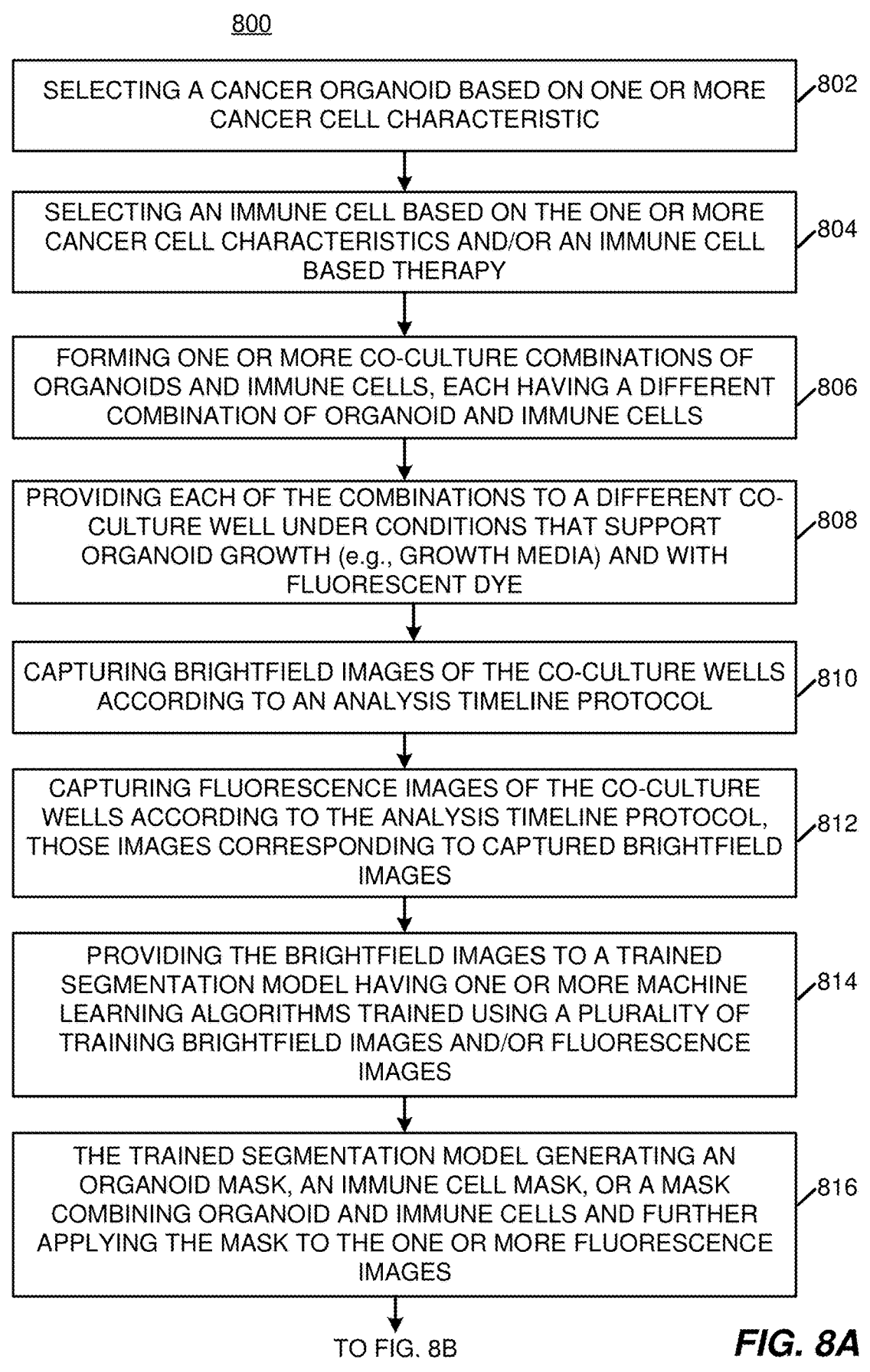

800

SELECTING A CANCER ORGANOID BASED ON ONE OR MORE CANCER CELL CHARACTERISTIC ⟋802

↓

SELECTING AN IMMUNE CELL BASED ON THE ONE OR MORE CANCER CELL CHARACTERISTICS AND/OR AN IMMUNE CELL BASED THERAPY ⟋804

↓

FORMING ONE OR MORE CO-CULTURE COMBINATIONS OF ORGANOIDS AND IMMUNE CELLS, EACH HAVING A DIFFERENT COMBINATION OF ORGANOID AND IMMUNE CELLS ⟋806

↓

PROVIDING EACH OF THE COMBINATIONS TO A DIFFERENT CO-CULTURE WELL UNDER CONDITIONS THAT SUPPORT ORGANOID GROWTH (e.g., GROWTH MEDIA) AND WITH FLUORESCENT DYE ⟋808

↓

CAPTURING BRIGHTFIELD IMAGES OF THE CO-CULTURE WELLS ACCORDING TO AN ANALYSIS TIMELINE PROTOCOL ⟋810

↓

CAPTURING FLUORESCENCE IMAGES OF THE CO-CULTURE WELLS ACCORDING TO THE ANALYSIS TIMELINE PROTOCOL, THOSE IMAGES CORRESPONDING TO CAPTURED BRIGHTFIELD IMAGES ⟋812

↓

PROVIDING THE BRIGHTFIELD IMAGES TO A TRAINED SEGMENTATION MODEL HAVING ONE OR MORE MACHINE LEARNING ALGORITHMS TRAINED USING A PLURALITY OF TRAINING BRIGHTFIELD IMAGES AND/OR FLUORESCENCE IMAGES ⟋814

↓

THE TRAINED SEGMENTATION MODEL GENERATING AN ORGANOID MASK, AN IMMUNE CELL MASK, OR A MASK COMBINING ORGANOID AND IMMUNE CELLS AND FURTHER APPLYING THE MASK TO THE ONE OR MORE FLUORESCENCE IMAGES ⟋816

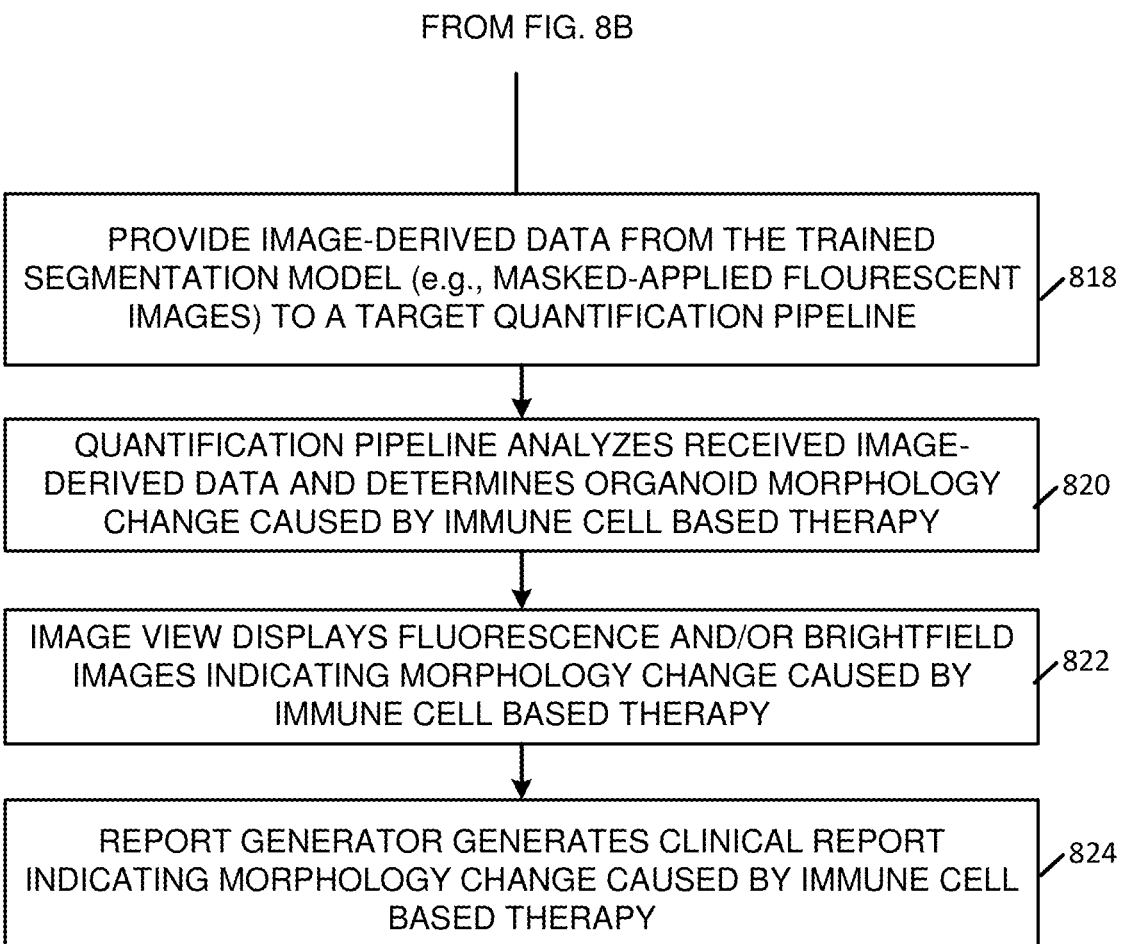

FROM FIG. 8B

PROVIDE IMAGE-DERIVED DATA FROM THE TRAINED SEGMENTATION MODEL (e.g., MASKED-APPLIED FLOURESCENT IMAGES) TO A TARGET QUANTIFICATION PIPELINE — 818

QUANTIFICATION PIPELINE ANALYZES RECEIVED IMAGE-DERIVED DATA AND DETERMINES ORGANOID MORPHOLOGY CHANGE CAUSED BY IMMUNE CELL BASED THERAPY — 820

IMAGE VIEW DISPLAYS FLUORESCENCE AND/OR BRIGHTFIELD IMAGES INDICATING MORPHOLOGY CHANGE CAUSED BY IMMUNE CELL BASED THERAPY — 822

REPORT GENERATOR GENERATES CLINICAL REPORT INDICATING MORPHOLOGY CHANGE CAUSED BY IMMUNE CELL BASED THERAPY — 824

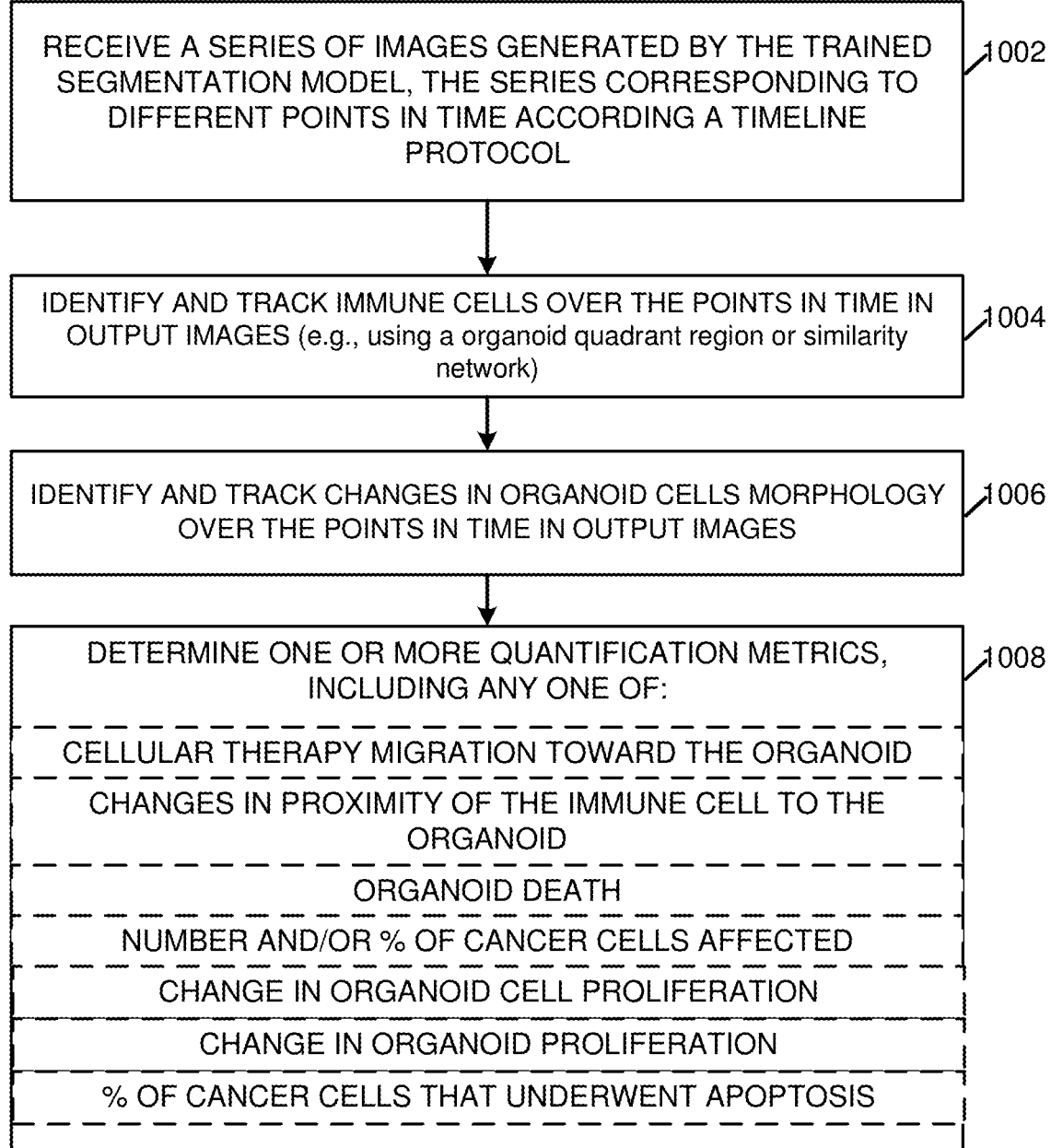

RECEIVE A SERIES OF IMAGES GENERATED BY THE TRAINED SEGMENTATION MODEL, THE SERIES CORRESPONDING TO DIFFERENT POINTS IN TIME ACCORDING A TIMELINE PROTOCOL — 1002

IDENTIFY AND TRACK IMMUNE CELLS OVER THE POINTS IN TIME IN OUTPUT IMAGES (e.g., using a organoid quadrant region or similarity network) — 1004

IDENTIFY AND TRACK CHANGES IN ORGANOID CELLS MORPHOLOGY OVER THE POINTS IN TIME IN OUTPUT IMAGES — 1006

DETERMINE ONE OR MORE QUANTIFICATION METRICS, INCLUDING ANY ONE OF: — 1008

CELLULAR THERAPY MIGRATION TOWARD THE ORGANOID

CHANGES IN PROXIMITY OF THE IMMUNE CELL TO THE ORGANOID

ORGANOID DEATH

NUMBER AND/OR % OF CANCER CELLS AFFECTED

CHANGE IN ORGANOID CELL PROLIFERATION

CHANGE IN ORGANOID PROLIFERATION

% OF CANCER CELLS THAT UNDERWENT APOPTOSIS

FIG. 10

PLATFORM FOR CO-CULTURE IMAGING TO CHARACTERIZE IN VITRO EFFICACY OF HETEROTYPIC EFFECTOR CELLULAR THERAPIES IN CANCER

CROSS-REFERENCE TO RELATED APPLICATIONS

This application claims priority to U.S. Provisional Application No. 63/203,749, filed Jul. 29, 2021, U.S. Provisional Application 63/227,877, filed Jul. 30, 2021 and U.S. Provisional Application No. 63/263,761, filed Nov. 8, 2021, which are incorporated herein by reference in their entirety.

FIELD OF THE INVENTION

The present disclosure relates to analyzing organoid response to immune-oncology (IO) therapies and, more particularly, to techniques for characterizing organoid morphology changes in an organoid and immune cell co-culture using trained machine learning models.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Cell engager and adoptive cell therapeutics have emerged as efficacious and durable treatments in patients with B-cell malignancies. Though many analogous strategies are under development in solid tumors, none have received approval. Preclinical development of these therapies requires cell labeling of immortalized cell lines and/or primary expanded T cells to distinguish target and effector cells. However, cell engager and adoptive cell therapies have limited evidence of reproducibility in primary patient-derived models. There is a need in the art for in vitro methods of examining the activity of immunotherapeutics which more closely mimic in vivo settings.

SUMMARY OF THE INVENTION

In an embodiment, a method for characterizing cancer organoid response to an immune cell based therapy, the method includes: providing a first combination of cancer organoid cells and immune cells to a first culturing well and culturing the combination under conditions which support organoid growth; capturing, at different time points, a plurality of brightfield images and corresponding fluorescence images of the culturing well comprising the first combination of cancer organoid cells and immune cells; providing the plurality of brightfield images and the plurality of corresponding fluorescence images to a trained model and, using the trained model, identifying and distinguishing cancer organoid cells and/or immune cells within the plurality of brightfield images and within the plurality of corresponding fluorescence images and characterizing cancer organoid morphology change caused by an immune cell based therapy, wherein the trained model comprises a one or more machine learning algorithms trained using a plurality of training brightfield images and/or a plurality of training fluorescence images; and generating an analytical report including a characterization of cancer organoid cell death caused by the immune cell based therapy.

In a variation of this embodiment, the method includes performing a stacking process on the plurality of corresponding fluorescence images to generate flattened fluorescence images of organoids within the first culturing well for each different time point; and wherein providing the plurality of images of corresponding fluorescence images to a trained model comprises providing the flattened fluorescence images to the trained model.

In another variation of this embodiment, wherein the fluorescence images of the culturing well are three-dimensional (3D) fluorescence images, the method further includes: performing a flattening process on the 3D fluorescence images to generate two-dimensional (2D) fluorescence images of organoids within the first culturing well for each different time point; and wherein providing the plurality of images of corresponding fluorescence images to a trained model comprises providing the 2D fluorescence images to the trained model.

In a variation of this embodiment, wherein the fluorescence images of the culturing well are three-dimensional (3D) fluorescence images, the method further includes: performing a slice on the 3D fluorescence images to generate 2D fluorescence images of organoids within the first culturing well for each different time point; and wherein providing the plurality of images of corresponding fluorescence images to a trained model comprises providing the 2D fluorescence images to the trained model.

In a variation of this embodiment, the method further includes, prior to the providing the first combination to the first culturing well: selecting the cancer organoid cells and the immune cells forming the first combination based on cancer cell characteristics and the immune cell based therapy.

In a variation of this embodiment, the method further includes providing a second combination of cancer organoid cells and immune cells to a second culturing well, wherein the second combination represents a different concentration of cancer organoids cells to immune cells than the first combination. In a variation, generating the analytical report further comprises providing a comparison of immune cell based therapy efficacies between the first combination and the second combination.

In another variation of this embodiment, characterizing cancer organoid morphology change caused by an immune cell based therapy comprises: characterizing cell death, cytokine secretion, and/or a shape change.

In another variation of this embodiment, characterizing the cancer organoid morphology change comprises: quantifying the number of cancer organoid cell deaths corresponding to each respective periodic capture of the plurality of brightfield and corresponding fluorescence images of the culturing well.

In a variation of this embodiment, characterizing the cancer organoid morphology change comprises: determining (i) the number and/or percentage of cancer organoid cells undergoing a phenotypic change over the different time points, (ii) proliferation of the cancer organoid cells over the different time points, and/or (iii) a change in morphology of the cancer organoid cells over different time points.

In a variation of this embodiment, the method further includes: identifying, using the trained model, the organoid cells that are surrounded by the immune cells; identifying, using the trained model, organoids that are infiltrated by the immune cells; identifying, using the trained model, a spatial relationship between organoid cells resistant to the immune cell based therapy; characterizing, using the trained model, immune cell migration and/or chemotaxis, and/or characterizing, using the trained model, co-localization of the immune cells and the cancer organoid cells.

In a variation of this embodiment, the method further includes: identifying and quantifying the number of immune cell deaths corresponding to each respective periodic capture of the plurality of brightfield and corresponding fluorescence images of the culturing well.

In a variation of this embodiment, the trained model comprises an organoid trained segmentation model for identifying cancer organoid cells in the brightfield images.

In a variation of this embodiment, the trained model comprises an immune cell trained segmentation model for identifying immune cells in the fluorescence images.

In a variation of this embodiment, identifying and distinguishing cancer organoid cells and/or immune cells within the plurality of brightfield images and within the plurality of corresponding fluorescence images comprises: using the trained model, generating from the plurality of brightfield images a masking image of segmented organoids and/or immune cells; and applying the masking image to the plurality of fluorescence images to identify the segmented organoids and/or immune cells in the fluorescence images In a variation of this embodiment, the masking image comprises a binary mask of segmented cancer organoid cells, the masking image comprises a binary mask of segmented immune cells, or the masking image comprises a categorical mask differentiating between cancer organoid cells and one or more types of immune cells, the categorical mask comprising a plurality of boundary types, each identifying a different one of the cancer organoid cells and types of immune cells.

In a variation of this embodiment, the trained model comprises a machine learning algorithm trained using a plurality of training images, wherein at least some of the plurality of training images include annotations identifying one or more of organoid targets, organoids of different morphology, organoids of different locations, and organoids generated by different culturing methods.

In a variation of this embodiment, the trained model comprises a machine learning algorithm trained using a plurality of training images, wherein at least some of the plurality of training images include annotations identifying one or more of fluorescence dye regions, different cell types, immune cell therapies, and degrees of immune cell therapy response.

In a variation of this embodiment, the trained model comprises a machine learning algorithm trained using a plurality of training images obtained from a pre-trained segmentation model that segmented out from a series of input images cancer organoid cells leaving immune cells remaining.

In a variation of this embodiment, the trained model comprises a machine learning algorithm trained using a plurality of training images obtained from a pre-trained segmentation model that segmented out from a series of input images immune cells leaving cancer organoid cells remaining.

In a variation of this embodiment, the trained model comprises a machine learning algorithm trained using a plurality of training images obtained from a pre-trained segmentation model that segmented out from a series of input images immune cells and cancer organoid cells.

In a variation of this embodiment, the trained model comprises a segmentation model trained to detect organoid cells and having a first machine learning algorithm trained using a plurality of training brightfield images.

In a variation of this embodiment, the trained model comprises a segmentation model trained to detect immune cells and having a first machine learning algorithm trained using a plurality of training brightfield images and a plurality of corresponding training fluorescence images having immune cells labeled.

In a variation of this embodiment, generating the analytical report further comprises generating a time-lapse imaging of the characterized cancer organoid cell deaths and/or the immune cells at the different time points.

In a variation of this embodiment, generating the analytical report further comprises identifying organoids resistant to the immune cell based therapy and/or organoids susceptible to the immune cell based therapy based on the changes in the characterized cancer organoid cell death over the different time points.

In a variation of this embodiment, the analytical report further includes a structured file of intensity values, pixel location, size, index, and/or death of the cancer organoid cells within the plurality of brightfield and corresponding fluorescence images.

In a variation of this embodiment, method further includes applying an intensity normalization process to each of the plurality of brightfield images by determining a background intensity of each respective brightfield image and normalizing the intensity by subtracting the background intensity from each respective brightfield image.

In a variation of this embodiment, providing the plurality of brightfield images and the plurality of corresponding fluorescence images to the trained model comprises: combining the plurality of brightfield images and the plurality of corresponding fluorescence images into one or more multi-channel images to be provided to the trained model.

In a variation of this embodiment, the method further including: quantifying metabolic activity of the cancer organoid cells and/or immune cells.

In a variation of this embodiment, the method further includes: characterizing a presence or amount of one or more biomarkers; and generating the analytical report to further include the characterized presence or amount of one or more biomarkers.

In a variation of this embodiment, the method further includes: quantifying a proportion of specific cell types from the first combination of the cancer cell organoids and the immune cells using fluorescence-activated cell sorting (FACS); and generating the analytical report to further include the quantified proportion of specific cell types.

In a variation of this embodiment, the immune cells include peripheral blood mononuclear cells (PBMCs).

In a variation of this embodiment, the immune cells are lymphocytes, monocytes, and/or dendritic cells.

In a variation of this embodiment, the immune cells include T cells and/or Natural Killer (NK) cells.

In a variation of this embodiment, the immune cells include neutrophils, eosinophils, basophils, and/or macrophages.

In a variation of this embodiment, the organoids are derived from at least one of anal cancer, a basal cell skin cancer, a squamous cancer, a benign cancer, a brain cancer, a glioblastoma, a breast cancer, a bladder cancer, a cervical cancer, a colon cancer, a colorectal cancer, an endometrial cancer, an esophageal cancer, a head and neck cancer, a liver cancer, a hepatobiliary cancer, a kidney cancer, a renal cancer, a gastric cancer, a gastrointestinal cancer, a lung cancer, a non-small cell lung cancer (NSCLC), a mesothelial cancer of the pleural cavity, a mesothelioma, an ovarian cancer, a pancreatic cancer, a prostate cancer, a rectal cancer, a lymphoma, a melanoma, a skin cancer, a meningioma, a sarcoma, and a thymus cancer.

In accordance with another embodiment, a method for characterizing cancer organoid response to an immune cell based therapy, includes: providing a first combination of cancer organoid cells and immune cells to a first culturing well and culturing the combination under conditions which support organoid growth; periodically capturing, at different time points, a plurality of brightfield images of the culturing well comprising the first combination of cancer organoid cells and immune cells; providing the plurality of brightfield images to a trained model and, using the trained model, identifying and distinguishing cancer organoid cells and immune cells within the plurality of brightfield images, generating an organoid segmentation mask and an immune segmentation mask; providing the organoid segmentation mask and dye images corresponding to the plurality of brightfield images to an organoid tracking process and generating organoid cell death tracking data; providing the organoid segmentation mask and the immune segmentation mask to an immune cell tracking process and generating immune cell tracking data, wherein the trained model comprises a one or more machine learning algorithms trained using a plurality of training brightfield images; and generating an analytical report including the immune cell tracking data and/or organoid cell death tracking data.

In a variation of this embodiment, the immune cell tracking data comprises immune cells clustered around organoids and/or immune cells infiltrated into organoids.

In another variation of this embodiment, the immune cell tracking data comprises immune cell type.

In a variation of this embodiment, the immune cells comprise CAR-T cells.

In a variation of this embodiment, the immune cells include peripheral blood mononuclear cells (PBMCs).

In a variation of this embodiment, the immune cells are lymphocytes, monocytes, and/or dendritic cells.

In a variation of this embodiment, the immune cells include T cells and/or Natural Killer (NK) cells.

In a variation of this embodiment, the immune cells include neutrophils, eosinophils, basophils, and/or macrophages.

In a variation of this embodiment, the organoid cell death tracking data comprises organoid cell death, organoid cell apoptosis, a number of organoid cells, and/or morphology organoid cells.

BRIEF DESCRIPTION OF DRAWINGS

This patent or application file contains at least one drawing executed in color. Copies of this patent or patent application publication with color drawing(s) will be provided by the United States Patent and Trademark Office upon request and payment of the necessary fee.

FIGS. 8A and 8B illustrate an example process for analyzing a co-culture formed of a combination of organoid cells and immune cells using a trained image model, of an image-based co-culture analysis system, in accordance with an example.

FIG. 10 illustrates a process that may be implemented by a quantification pipeline of an image-based co-culture analysis system, in accordance with an example.

Figure 1:
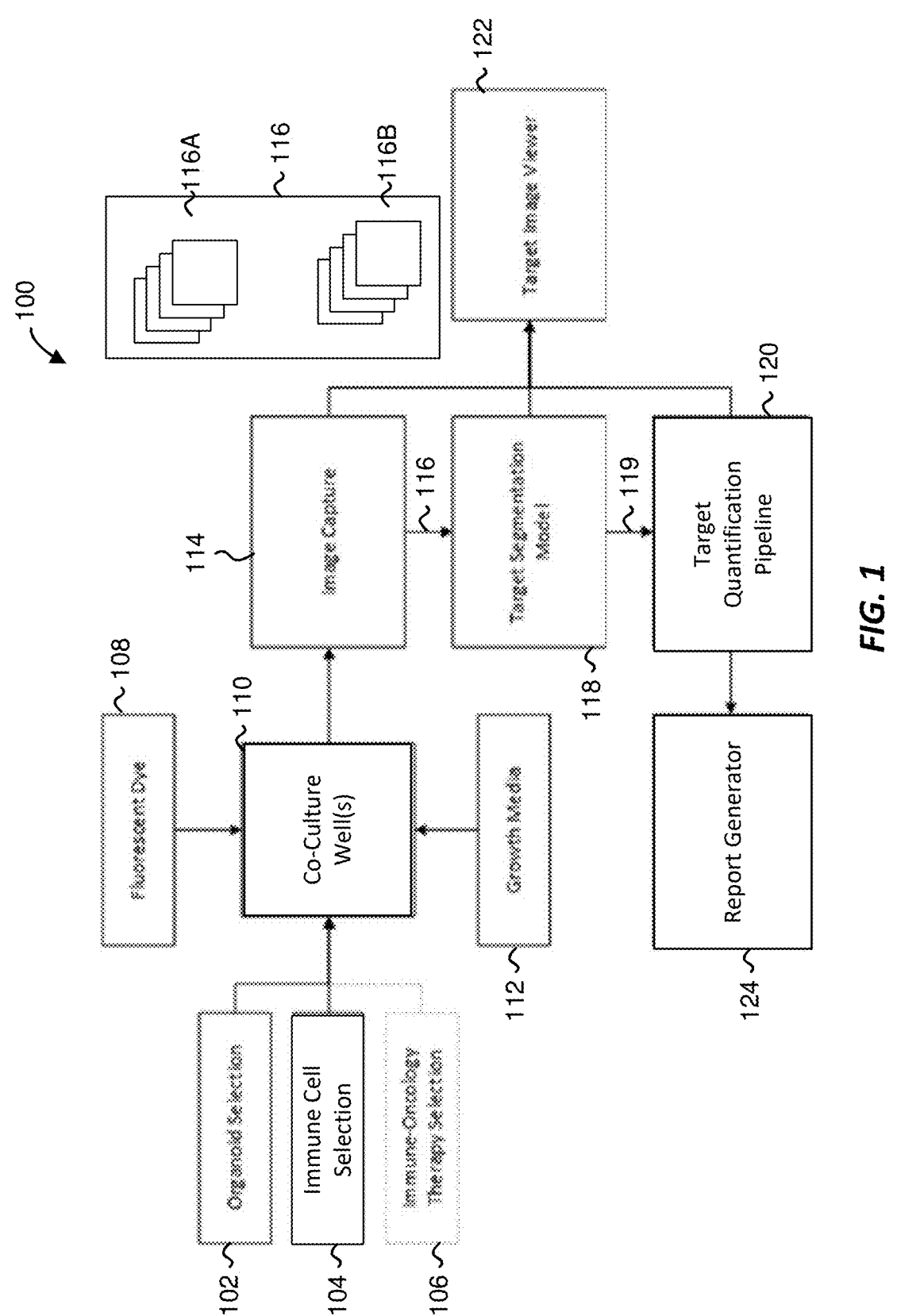
FIG. 1 is a schematic of an image-based co-culture analysis system, in accordance with an example.

The figures described below depict various aspects of the system and methods disclosed herein. It should be understood that each figure depicts an example of aspects of the present systems and methods.

DETAILED DESCRIPTION

The present application describes a cell culture system where multiple cell types may be cultured and analyzed together, providing an improved in vitro model system to study, e.g., the effect of therapeutic agents on a mixed population of cells, including the interaction between different cell types (e.g., tumor cells and immune cells) and changes in the phenotype of cells in the mixed population.

When measuring immunotherapy effects in human in vitro model systems, it is important to resolve tumor cell death from immune cell death in order to create an accurate assay with high precision. This typically requires fluorescence counter-staining of immune cells and nucleus staining, a time-consuming procedure that may introduce experimental confounders due to stain toxicity.

The present application describes systems and methods that allow for the co-culturing of tumor organoids with immune cells, such as peripheral blood mononuclear cells (PBMCs) or other effector cells, in the presence of therapeutic agents (optionally at various dosage levels) to assess the agent's effectiveness in enabling the immune cells to kill the tumor organoids. The system and methods described herein overcome many obstacles associated with existing in vitro methods. Utilizing machine vision coupled with time-lapse-microscopy, the techniques described herein enable, e.g., multiparameter kinetic readouts of changes in tumor organoid phenotype (such as, for example, organoid cell death) and immune cells.

In some examples, the systems and methods automatically segment organoids and distinguish them from immune cells using brightfield images, then quantify the amount of cell death, or apoptosis, from a single cell death indicator within organoids. The systems and methods may quantify other phenotypic changes in organoids identifiable from brightfield and/or fluorescence images. In other examples, the amount of cell death is quantified from more than one cell death indicator.

The systems and methods include an automated process that distinguishes cellular phenotypes between various cell populations, such as tumor cells and immune cells in microscopy based assays. The nature of the assay allows for time-lapse imaging to quantify the effectiveness of a therapeutic agent over time.

In some examples, the systems and methods may comprise automated segmentation and quantification of immune cell mediated cytotoxicity in time-lapse, co-culture imaging assays involving patient-derived tumor organoids and immune cells. The immune cells may or may not be derived from the same patient, or from a patient having the same HLA type(s) as the patient source of the organoids.

The systems and methods may include one or more of the following: an in vitro assay using human tumor cells in the form of cells or three-dimensional organoids and autologous or allogeneic primary human immune cells or autologous or allogeneic modified immune cells; a protocol that sets the temporal, cell quantities, culture, and drug treatment conditions; an imaging protocol to record tumor and immune cell images over time via microscopy; a neural network that is able to process these images and resolve tumor cells from immune cells; an automated recording of all individual organoids within each image; spatial tracking of individual organoids and/or individual heterotypic effector cells (e.g., PBMC, such as T-cells, macrophages, etc.) in relation to one and other in two-dimensional (2D) space, three-dimensional (3D) space, or space and time series; an automated quantitation of tumor organoid size/shape, like microscopy visual features and or any vital dye staining that measures cellular phenotypes such as apoptosis or death. In various embodiments, the immune cells include T-cells, which are optionally isolated from PBMCs or another source and expanded.

Immunotherapy is a type of treatment that leverages a patient's immune system to fight disease. "Immune cell based therapy" includes both cellular therapeutics (e.g., T cells comprising chimeric antigen receptors (CAR T cells)) and non-cellular therapeutics that modulate immune cell activity to achieve a desired biological response. Non-cellular therapeutics include, but are not limited to, small molecule (i.e., traditional pharmaceutical) agents and large molecule (i.e., biological) agents which modulate immune cell activity. "Immune cell based therapy" is also referenced herein as "immune-oncology (IO) therapies" or "immune-oncology (IO) agents." It will be appreciated that descriptions provided herein with respect to therapeutic agents apply to agents previously established to have immune modulating (and, optionally, anti-cancer) activity as well as candidate (or experimental) agents where immune modulation activity is under investigation.

FIG. 1 displays an exemplary image-based co-culture analysis system 100. In the illustrated example, an organoid selection 102 results from an organoid selection process, e.g., that may include identifying organoids most relevant to the instant assay and selecting them from other organoids not relevant to the instant assay, as described herein. An immune cell 104 may result from a cellular therapy selection process, e.g., that may include identifying one or more heterotypic cellular therapies which are expected to initiate a phenotypic change (e.g., apoptosis) within the selected organoids after exposure to the heterotypic cellular therapy and, optionally, immune-oncology therapy. An immune-oncology (IO) therapy 106 may result from an immune-oncology selection process, e.g., that may include identification of one or more IO therapies for inclusion into the instant assay to assess the effects of the IO therapy. In some implementations, when assaying the efficacy of a cellular therapy against the organoids without an IO therapy present, an IO therapy may not be selected.

Once selected, patient-derived organoids 102 and immune cells 104 (such as PBMC material or selections of types of PBMCs, such as T cells) may be combined to form a co-culture and distributed into one or more culture wells 110, each well including a growth media 112 to promote the growth of the co-culture. A cell death indicator, for example, a fluorescent dye 108 or other marker of apoptosis and/or an immune oncology therapy candidate 106 may be added to one or more culture wells that contain the co-culture combination. The identified organoid cells and immune cells may be combined into co-culturing wells in different combinations. For example, a co-culture combination may be formed by selecting the cancer organoid cells and the immune cells based on cancer cell characteristics and/or based on the immune cell based therapy. Different characteristics and/or therapies may result in different co-culture combinations. The different combinations of organoid cells and immune cells may be provided to different co-culturing wells. For example, cancer organoid tissue associated with the same original sample tissue may be combined with different types of immune cells and placed in different co-culturing wells. As a further example, different combinations may have different concentrations or ratios of cancer organoid cells to immune cells. Further still, as used herein, references to organoid tissue include organoids that may be multiple passages removed from the sample tissue. Further organoid tissue may be directly grown from a sample tissue from a subject or may be grown from organoids that were grown from that tissue.

With the present techniques, various cancer (organoid) cell characteristics and immune cell based therapies characteristics may be measured and used to create co-cultures and/or to determine the efficacy of immune therapies. The various characteristics include cell mortality, transcriptional profile, proteomic profile, epigenetic profile, cell morphology, growth rate, abundance of extracellular protein in the culture of the tumor organoid cell line, cellular membrane potential, mitochondrial membrane potential of the organoid cell line, morphology or architectural change of the organoid cells line, upregulation of autophagy of the organoid cell line, chromosomal changes in ploidy in the organoid cell line, chromosomal breakage, telomere length change, cytoskeletal change or cell motility change. These characteristics may be determined from gene sequencing data, for example, and may be determined, in various embodiments, before co-culturing, as a part of selection of the constituents for co-culturing, and/or after a co-culturing experimentation.

The resulting combination within the co-culture wells 110 is examined by microscopy, such as through use of a confocal microscope (ImageXpress), via an image capture stage 114. The resulting microscopy images 116 may be analyzed by a trained target segmentation model 118, which determines the boundary for individual targets within the microscopy images 116, such as determining which cells in the image are organoids (e.g., cancer cells), which are immune cells (e.g., PBMCs), and filtering out non-cellular targets such as background noise or artifacts. The images 116 from the image capture stage 114 may be brightfield images 116A and corresponding fluorescence images 116B, for example. The output 119 from the segmentation model 118 may be brightfield images, fluorescence images, or a combination of brightfield and fluorescence images. In some examples, one or more types of the input images 116 may be combined into multi-channel images and/or projections that flatten all intensity information into one 2-dimensional image. In some examples, image flattening occurs after the segmentation model 118 has identified and classified the cell types in the input images 116.

In some examples, the output 119 from the segmentation model 118 may be a structured CSV file or other image-derived data having organoid locations and sizes and pixel intensities and/or a mask generated by the segmentation model 118. This output data may then be processed by a quantification pipeline 120 configured to perform a target quantification process that determines the number and/or percentage of cancer cells that underwent a phenotypic change, such as apoptosis, alterations in cytokine secretion, change in proliferation, change in morphology, etc., and these features can be visualized by light microscopy or with the aid of fluorescent staining, or chromogenic or fluorescent vital dyes.

In some examples wherein apoptosis is examined, the quantification pipeline 120 may determine the total number of apoptotic cells in the culture well based on activation of a fluorescent molecule that activates upon cleavage by the enzymes caspase 3 or caspase 7; the percent of cancer cells in the culture well that underwent apoptosis; the number of apoptotic cells in each organoid; and/or the percentage of the cancer cells in an organoid that underwent apoptosis. The organoid cell death may be caused directly or indirectly by effector cells in the co-culture, which may be enhanced by one or more IO agents. In one example, one or more organoids may be resistant to the IO agent/immune cell mediated killing and few of the cancer cells in the organoid die after exposure to the IO agent/immune cells. In another example, one or more organoids may be susceptible to the IO agent/immune cell mediated killing and many of the cancer cells in the organoid die after exposure to the IO agent/immune cells.

It will be appreciated that, while various examples described herein relate to apoptosis, the disclosure contemplates characterization of other cell phenotypes instead of, or in addition to, apoptosis. Examples of cell phenotypes include, but are not limited to, necrosis, proliferation, morphology, cytokine secretion, chemotaxis, and the like. The system and methods described herein are not limited to use in examining the phenotype of a particular cell type, but also are suitable for characterizing the interaction of organoid cells with immune cells in the co-culture. For example, phenotypic changes also may include co-localization of organoid cells and immune cells in the culture, special organization of the organoid cells and immune cells, or immune cell infiltration into the organoid structure. It will be appreciated that descriptions of the system and methods with respect to characterizing apoptosis also may apply to characterization of one or more of the other phenotypic changes described herein.

Once image capture is complete, and a combination of image capture and target segmentation are complete, or a combination of image capture, target segmentation and target quantification are complete, an image viewer 122 may receive one or more of the output 119, e.g., in the form of an image, a mask, the fluorescent channel, an overlay of the target quantification for viewing, or a combination of these or multiples of these. In some examples, the target image view 122 forms an image capture system with the image capture stage 114, such that the output 119 may be viewed in real time or may be viewed from a display at any time after generation passively (such as a slide show or wall panel) or on demand (such as at the instruction to view a specific image and/or segmentation mask and/or target quantification report or overlay).

In some examples, the system 100 may also include a report generator 124 configured to generate a report of the distribution of immune cells and/or organoids developed from the output of the target quantification pipeline 120. For example, after exposure to the IO agent, the system 100 may be used to determine whether susceptible organoids are surrounded by PBMCs, and/or if immune cells are infiltrating organoid volume/space, and/or if resistant organoids are located in proximity to effector cells or far from the effector cells, which may be useful for understanding, e.g., how resistant organoids avoid cell death.

In various examples, the systems and methods may be used to test the efficacy of immunology drugs in causing the death of patient derived tumor organoids cultured with autologous or HLA matched or mismatched allogeneic effector cells from another individual. The systems and methods may be used to measure the efficacy of immune oncology drugs or cell therapies on human systems in vitro, where the drugs or therapies are either FDA approved, or in clinical or pre-clinical development.

Figure 2:
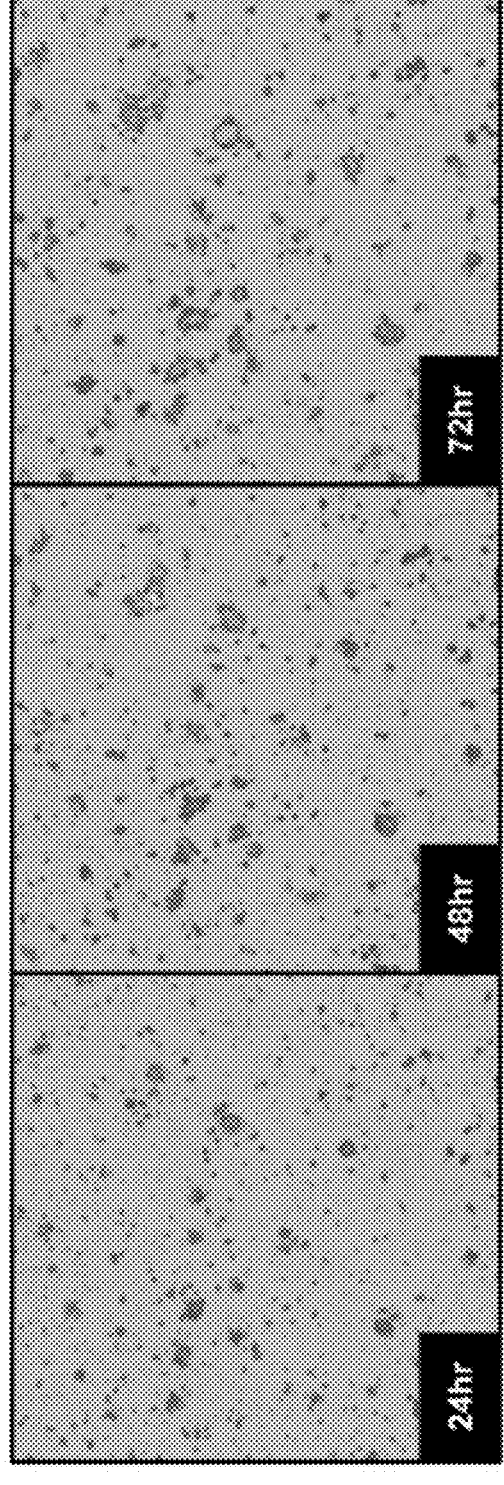
FIG. 2 are brightfield images that are output from the image-based co-culture analysis system of FIG. 1, at multiple points in time, in accordance with an example.

The co-culture system 100 may be used to characterize organoid morphology changes over time, for example, in response to immune cell based therapies. FIG. 2 illustrates an example output of the co-culture system 100, showing a resulting co-culturing image analysis of captured images at multiple points in time used to analyze growth of individual organoids in the co-culture and to analyze the movement of immune effector cells in the co-culture. Shown are brightfield images taken at 24 hrs, 48 hrs, and 72 hours after introduction of all components necessary for instantiation of the assay into the co-culture well. The co-culture system 100 has generated brightfield images showing highlighted cellular apoptosis or other markers (depending on the dye included) in a raw, unfiltered image. In some instances, not illustrated, the channels of the image may be illustrated separately, or they may be provided together as an overlapped image to emphasize the fluorescence of the dyes and any colocalization of two or more dyes. In an example, each channel may show a different color (different fluorescent dye), and each dye may be for a different molecule. For example, the molecule tagged by the dye could be a cell death marker, or the molecule could be a protein that is specific to a certain type of cell, etc. CD8 and CD4 are example markers of certain T-cells, for example. FOXP3 is another marker. In some examples, the co-culture may first be introduced to promote growth while in other examples, all components of the assay are provided to the co-culture well within a reasonable time.

In another example, the co-culture system 100 may be used to examine culturing one or more organoids in the presence of effector cells, such as T-lymphocytes. In some examples, the co-culturing of organoids does not involve expansion of T-cells. The co-culturing process may include the application of one or more drugs or other agents used in the treatment of disease, such as cancer. The co-culturing system may be used to determine whether the agents applied in the co-culture system may stimulate effector cells in the co-culture system to kill one or more organoids, or co-localize the effector cells to the organoids.

The immune cells in the co-culture may be a mixed population of immune cells or a single type of immune cell. As referenced above, an immune cell selection process (e.g., at the selector 104 of FIG. 1) may be performed on a number of cell-types, including effector cells, heterotypic cells, or other cells which are expected to have an effect on the cells of the organoid. Effector cells may be primary cells from various lineages from the hematopoietic or mesenchymal lineages. Effector cells may be long-term primary cell cultures, immortalized cell lines, or genetically or chemically modified cells. Effector cells may be provided in the form of primary immune cells, such as peripheral blood mononuclear cells (PBMCs) from an individual. PBMCs comprise a mix of immune cells, such as monocytes, lymphocytes (T cells, B cells, and Natural Killer (NK) cells), and dendritic cells that reside in circulation. The PBMCs may be provided by the same subject from whom the organoids were derived or may be provided by a different subject. Commercially available PBMCs are known in the art. Another primary immune cell population contemplated herein includes immune cells (e.g., monocytes, T cells, and/or macrophages) that reside within tumors (for example, tumor infiltrating lymphocytes) and are isolated from enzymatic digestions of tumors. Other immune cells suitable for use in the co-culture of the disclosure include, but are not limited to, neutrophils, eosinophils, basophils, and macrophages. Any combination of the immune cell types described herein is contemplated, and co-culture with a single type of immune cell is also contemplated. In various embodiments, the immune cells (e.g., PBMCs) have the same HLA type(s) as the tumor organoid cells (i.e., the immune cells and organoid cells are HLA matched).

In some aspects, the immune cells in the co-culture are cellular therapeutics, themselves. In other aspects, cellular therapeutics (i.e., Heterotypic Cellular Therapies) are provided to the co-culture in addition to the immune cells. Examples of cellular therapeutics include, but are not limited to, natural killer cells, lymphocytes, plasma cells, macrophages, monocytes, effector cells of myeloid lineage, effector cells of lymphoid lineage, effector cells from stromal/fibroblast lineage, cells from hematopoietic lineage, and cells from mesenchymal lineage. For the purposes of this disclosure, cellular therapies (e.g., heterotypic cellular therapies) include one or more types of effector cells such as those listed above.

Different ratios of immune cells and organoid cells may be employed in the co-cultures of the methods described herein. In one example, a 1:1 ratio of immune culture (for example, the number of immune cells) to organoid culture (for example, the number of individual cells including the organoids) may be used in the co-culture system. In other examples, ranges between 2:1 and 20:1 may be used. For example, the ratio of immune cells to organoid cells may be about 1:1, about 2:1, about 3:1, about 4:1, about 5:1, about 6:1, about 7:1, about 8:1, about 9:1, about 10:1, about 11:1, about 12:1, about 13:1, about 14:1, about 15:1, about 16:1, about 17:1, about 18:1, about 19:1, or about 20:1. Alternatively, the ratio of organoid cells to immune cells may be about 2:1, about 3:1, about 4:1, about 5:1, about 6:1, about 7:1, about 8:1, about 9:1, about 10:1, about 11:1, about 12:1, about 13:1, about 14:1, about 15:1, about 16:1, about 17:1, about 18:1, about 19:1, or about 20:1.

Cell culture techniques are well understood in the art. In the context of the instant disclosure, the organoid cells and immune cells are maintained under conditions which support the growth and propagation of the cells for a period of time suitable to characterize changes in phenotype in response to an immune cell based therapeutic. General culture conditions for mammalian cells are disclosed in, e.g. Animal cell culture: A Practical Approach, D. Rickwood, ed., Oxford University Press, New York (1992). In some examples, the co-culture media comprises both organoid growth media and immune cell growth media. In other examples, the co-culture media comprises organoid growth media, but not immune cell growth media. In other examples, the co-culture media comprises immune cell growth media, but not organoid growth media.

In one example, recombinant human IL-2 may be provided, such as at a concentration of 0-100 ng/mL, and at least one of CD2, CD3, and/or CD28 antibodies, such as StemCell ImmunoCult Human CD3/CD28/CD2 T Cell Activator may be added at a concentration such as 10-50 microliters/mL to present a 'cocktail' before or during introduction of immune cells (e.g., PBMC) with tumor organoid to enhance stimulation of T cells present in the immune cell population.

In another example, the cell culture media cocktail may include human recombinant IFN-gamma, such as at a concentration 0-400 ng/ml, before or during introduction of immune cells (e.g., PBMC) with tumor organoid to enhance stimulation of T cells present in the immune cell population.

In another example, one or more antibodies, including active ingredients/factors from immune media, may be added to the organoid media at the same concentration as they would be in the immune media. One or more antibodies alternatively may be provided as plate-bound antibodies or antibody conjugated Dynabeads.

An example implementation of the processes for the stages 102, 104, 110, and 112 is as follows. It will be appreciated that the example implementation is provided to illustrate various features of the system and method of the disclosure; the features described below are applicable to other implementations.

For the organoid selection 102, tumor organoids were first dissociated into single cells, which were then seeded into individual partitions in the presence of tumor organoid culture media. Tumor organoids, for example, may be derived from cells from any suitable cancer including, but not limited to, an anal cancer, a basal cell skin cancer, a squamous cancer, a benign cancer, a brain cancer, a glioblastoma, a breast cancer, a bladder cancer, a cervical cancer, a colon cancer, a colorectal cancer, an endometrial cancer, an esophageal cancer, a head and neck cancer, a liver cancer, a hepatobiliary cancer, a kidney cancer, a renal cancer, a gastric cancer, a gastrointestinal cancer, a lung cancer, a non-small cell lung cancer (NSCLC), a mesothelial cancer of the pleural cavity, a mesothelioma, an ovarian cancer, a pancreatic cancer, a prostate cancer, a rectal cancer, a lymphoma, a melanoma, a skin cancer, a meningioma, a sarcoma, and a thymus cancer. In various aspects, the organoid comprises a single cancer cell type. In other aspects, the organoid comprises more than one cancer cell type. In various aspects, the organoid comprises cancer cells and other types of host cells.

In various implementations of the organoid selection 102, organoids may be derived (for example, from patient specimens), cultured and analyzed according to the systems and methods disclosed in U.S. patent application Ser. No. 16/693,117, titled "Tumor Organoid Culture Compositions, Systems, and Methods", filed Nov. 22, 2019; PCT/US20/56930, titled "Systems and Methods for Predicting Therapeutic Sensitivity", filed Oct. 22, 2020; U.S. patent application Ser. No. 17/114,386, titled "Large Scale Organoid Analysis", filed Dec. 7, 2020; PCT/US2020/063619, titled "Systems and Methods for High Throughput Drug Screening", filed Dec. 7, 2020 and U.S. patent application Ser. No. 17/301,975, titled "Artificial Fluorescent Image Systems and Methods", filed Apr. 20, 2021, which are each incorporated herein by reference and in their entirety for all purposes.

Example Immune Cell Culture Media.

In some example implementations of the cellular selection 104, an immune cell culture media that is specific to one immune cell type is used, such as monocytes or macrophages. In some examples, the culture media for the immune cells may be a combination of media. In an example, immune cell culture media may include RPMI-1640 medium (Gibco, cat #11875-093), Fetal Bovine Serum (Gibco, cat #A31604-02), and ImmunoCult™-XF T Cell Expansion Medium (Stemcell Technologies, cat #10981).

Well.

In some examples, the co-culture well 110 may be present in a multi-well plate, such as CELLSTAR® 96-w plate black clear flat bottom (Greiner Bio-One cat #655090). In various embodiments, other culture well plate sizes may be used (for example, 48-well, 384-well plates, etc.). In various embodiments, a plate (for example, a 24-well plate) may be used with a dome of matrigel (for example, 50-100% matrigel).

Example Tumor Organoid Culture Media.

In an example, the culture media for the tumor organoids was prepared using the following components in the following concentrations:

| Component | Stock Concentration | Final Concentration |
|---|---|---|
| Advanced DMEM/F12 | 1x | 1x |
| HEPES | 1M | 1 mM |
| GlutaMax | 100x | 1x |
| B-27 w/o vit A | 50x | 1x |
| Pen-Strep | 100x | 1x |
| N-acetyl-cysteine | 500 mM | 1 mM |
| Nicotinamide | 1M | 10 mM |
| A83-01 | 5 mM | 0.5 μM |
| SB202190 | 5 mM | 0.5 μM |
| rh EGF | 50 μg/mL | 50 ng/ml |
| rh Noggin | 50 μg/mL | 100 ng/ml |
| rh Wnt-3A | 10 μg/mL | 100 ng/ml |
| rh R-Spondin 1 | 500 μg/mL | 500 ng/ml |

-continued

| Component | Stock Concentration | Final Concentration |
| --- | --- | --- |
| rh FGF7 | 50 µg/mL | 25 ng/ml |
| rh FGF10 | 50 µg/ml | 100 ng/ml |

Dissociation of Tumor Organoids.

Organoids in log phase growth may be dissociated from matrigel, for example, using Corning Cell Recovery Solution. A fixed volume aliquot of the resultant organoid suspension may be digested with TrypLE to approximate the number of cells per unit volume. Depending on the required number of target cells, organoids may be resuspended at a volume of 500-10,000 cells per 50 µL of media per well containing 5-50% vol:vol Matrigel or other extracellular matrix in a 15 ml conical tube and stored on ice.

Effector Cell Preparation for Co-Culture.

The immune or effector cell selection of 104 may be prepared as follows. Primary effector cells may be freshly isolated from biospecimens, be utilized from long-term cultures, or may be thawed from cryo-aliquots and cultured to recover from cryo-preservation in selected media for a period of time ranging from several hours to 24 hours as previously described (see, Yotam E Bar-Ephraim, Kai Kretzschmar, Hans Clevers; Organoids in immunological research Nat Rev Immunol. 2020 May; 20 (5): 279-293. doi: 10.1038/s41577-019-0248-y. Epub 2019 Dec. 18.).

Immune Cell Addition to TOs.

In an example, PBMCs were counted and checked for viability. Depending on the required effector cells:target cells ratio, a required number of live PBMCs were mixed with tumor organoids in 50 µL media containing 5%-50% matrigel and plated in plates, such as 96-well plates of the co-culture well device 110. The plates were incubated at 37° C. for 15 min-30 min for polymerization of the matrix. Once the matrigel was polymerized, 200-300 µL of media was added to the wells containing PBMCs-tumor organoids cultures. In various embodiments, other culture well plate sizes may be used (48-well, 384-well plates, etc.). In various embodiments, a 24-well plate may be used with a dome of matrigel (for example, 50-100% matrigel).

Apoptotic Response/Cell-Death Reagent Addition to Culture.

TO/Single cells-PBMCs. Sufficient volume of the growth media 112 is prepared containing a viability dye such as Caspase 3/7 activity, Annexin V/Alexa Fluor reagent, APO-BrdU TUNEL Assay Kit, or other DNA-binding/cell membrane permeability assay like YO-PRO-1, or TO-PRO-3. In one example, the final concentration may be 1.25 µM. An immune cell based therapeutic, negative controls and positive controls may also be added to culture. Depending on current volume per well, the growth media containing viability dye and candidate immune cell based therapeutic was prepared. In one example, a growth media containing viability dye and candidate immune cell based therapeutic in the amount of 50 µL was added in each well, to achieve a total volume of 300 µL per well.

While exemplary laboratory values such as for temperatures, concentrations, and ratios are provided herein, it should be understood to one of ordinary skill in the art that differing temperatures, concentrations, and ratios are covered herein such as to successfully instantiate an instant assay using laboratory values necessary for the specific organoids, cellular therapies, IO therapies, fluorescent dyes, growth media, and/or co-culturing wells as may be selected herein.

In various examples, each IO therapeutic agent of the IO therapy selection 106 (for example, an IO therapeutic agent or a clinical candidate) may be added to the organoid selection, organoid and immune cell co-culture, etc. in an amount that achieves a final concentration of 100 ng/ml-1 mg/mL. In some examples, the IO therapeutic agent or clinical candidate is a biologic, such as an antibody, and the final concentration for each biologic may be approximately 0.01 ug/ml to 50 ug/ml. In some examples, the IO therapeutic agent or clinical candidate is a small molecule, and the final concentration may be approximately 0.1 pM to 1 nM. The bounds may be increased and/or decreased based upon the therapeutic agent selected. More than one IO therapeutic agent or clinical candidate may be assayed, and the concentration of each may be the same or different.

In one example, the growth media containing viability dye, IO therapeutic agent (referenced below as "experimental compound(s)") and reagents were added to appropriate wells as per following conditions:

1. Organoids only [without experimental compound(s)]
2. Organoids+PBMCs [alone without experimental compound(s)]
3. PBMCs+Experimental compound(s) [in the absence of Organoids]
4. Organoids+PBMCs+Experimental compound(s)
5. Organoids+PBMCs+Negative control [where a "Negative control" is a vehicle or compound not expected to elicit organoid death/apoptosis itself or enhance affinity of PBMC/Organoid mediated death/apoptosis]
6. Organoids+PBMCs+Positive control [where a "Positive control" compound that is known to elicit organoid death/apoptosis itself or enhance affinity of PBMC/Organoid mediated death/apoptosis]

After adding the assay reagents and viability dye, the plates were transferred to a humidified 37° C. mammalian tissue culture incubator with 5% $CO_2$ and ambient oxygen.

Types of Agents/Drugs for Testing Use.

The co-culturing system 100 may be used to test the efficacy of any IO therapeutic agent, alone or in combination with other therapeutic agents (such as one or more other IO therapeutic agents). As described above, immune cell based therapeutic agents include cellular therapeutics, as well as large molecule (biologics) and small molecule (pharmaceutical) agents that modulate immune cell activity. Examples of adoptive cell therapies include, for example, tumor-infiltrating lymphocyte therapy and immune cells (such as T cells and NK cells) engineered to express chimeric antigen receptor (CAR T-cells). Autologous or allogeneic effectors cells are contemplated, as well as autologous or allogeneic engineered or synthetic effector cell populations such as CAR T-cells. Examples of CAR T cell therapies include, but are not limited to, Axicabtagene ciloleucel (Yescarta®), Brexucabtagene autoleucel (Tecartus™), Idecabtagene vicleucel (Abecma™), Lisocabtagene maraleucel (Breyanzi®), and Tisagenlecleucel (Kyrmriah®). Examples of biologics include recombinant proteins, such as antibodies and antibody-like constructs, which modulate the activity of immune cells and/or recruit immune effector cells to tumor cells. In various aspects, the immune cell based therapeutic is recombinant protein (e.g., an antibody or antibody-like construct) which engages/activates effector immune cells when in the presence of the tumor organoid cells. For example, in some aspects, the immune cell based therapeutic is a bispecific antibody or bispecific antibody-like construct (such as scFv-based constructs, bispecific Fabs, diabodies, and the like) which binds an immune effector cell and a tumor cell antigen. In various aspects, the antibody or antibody-like construct is a checkpoint inhibitor. The immune cell based therapeutic also may be DNA or RNA-based, such as RNA-based nanoparticles which upregulate T cell activation. Alternatively, the immune cell based therapeutic may be a small molecule drug, such as those which inhibit PI3K or Btk or activate T cells via, e.g., TLRs.

The plates of the co-culture well 110 may be imaged with a standard or inverted microscope at the desired time points, such as 0 h, 6 h, 12 h, 24 h, 48 h, and 72 h (or other time periods over seconds, minutes, hours, days, as desired). Identification of time periods may include measuring the kinetics of a specified phenotype/endpoint of interest and terminating the assay when a slowing down/inflection point of the rate of the phenotype has been observed or measured. Assays may be terminated after 72-96 hours when the effector cell killing/viability saturates or slows down. 5-10 µl of media may be harvested at 24 h, 48 h and 72 h for analyzing cell proliferation and metabolic activity such as MTS, LDH, or Cell-titer Glow assay(s) as an indicator of the presence and abundance of living cells.

10-50 µl of media may be harvested from each co-culture well at desired time periods (for example, 24 h, 48 h, and 72 h) for other biomarkers such as chemokines and cytokines as measured by ELISA/multiplex-cytokine assay or other immuno-assays using commercially available kits (Bio-techne/R&D Systems). Media containing PBMC (or other component immune cells), and/or organoids can be harvested from individual wells, or combined by treatment-type for sorting and analyses by FACS (fluorescence-activated cell sorting) to compare relative proportions of remaining live cell types by treatment type (such as proportions of CD8+ T-cells).

In various embodiments, T-cells or other immune cells may be analyzed by single-cell RNA sequencing, for example, to assess activation and/or exhaustion of the cells.

The system may further comprise an image analysis system for analyzing a readout at one or more time points for each condition of the cells in the culture media. In some examples, the image analysis may be a fluorescence-based image analysis. A neural network architecture may be used to distinguish between tumor organoids killed and immune cells killed.

Figure 3:
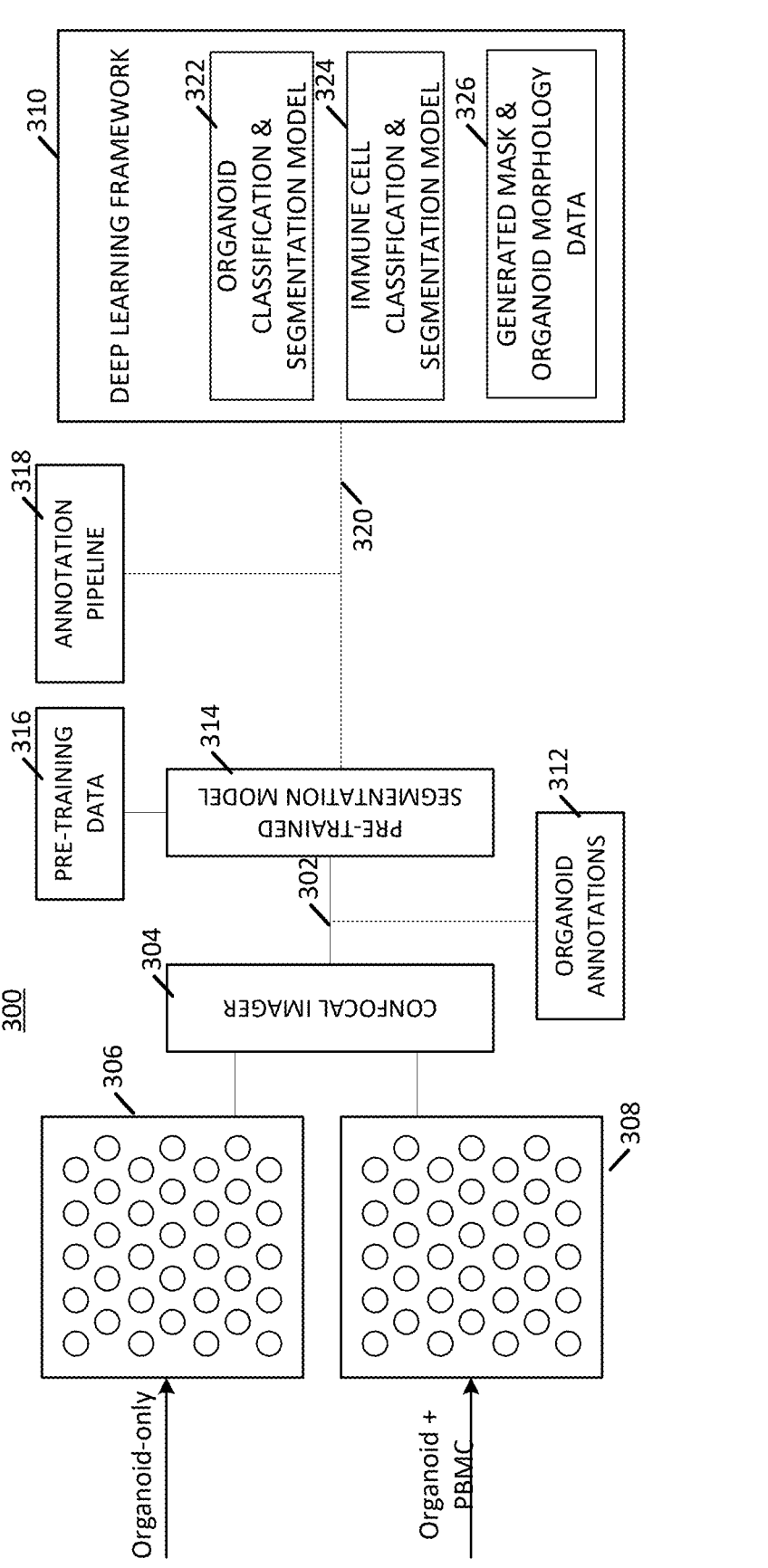
FIG. 3 is a schematic of an example architecture for training an image-based co-culture analysis system showing an organoid classification and segmentation model and an immune cell classification and segmentation model, in accordance with an example.

FIG. 3 illustrates an example training system 300 for training a co-culture analysis system, in particular for training a deep learning framework 310 to identify organoid cells and immune cells within captured images for quantification pipeline analysis. In the illustrated example, training images 302 are generated by a confocal imager 304. In an example, these training images 302 are images of culture wells and, more specifically, different types of culture wells. In the illustrated example, a first culture well plate 306, for example, may contain only organoid cultures, and a second culture well plate 308 may contain organoids co-cultured with PBMCs. During training of the deep learning framework 310, the confocal imager 304 captures brightfield images of the well plates 306 and 308 and these brightfield images are used for training. In other examples, the confocal imager 304 captures fluorescence images which are used for training. In yet other examples, a combination of brightfield and corresponding fluorescence images are used for training. In an example training process, the confocal imager 304 generated brightfield images taken from an organoid-only cultures in 384-well plates 306 and other brightfield images taken from organoids co-cultured with PBMCs in Matrigel at different concentrations in 96-well plates 308. For example, the brightfield images 302 were acquired at 10× magnification using an ImageXpress Micro Confocal High-Content Imaging System (Molecular Devices) as the confocal imager 304, where each image was sized of 1024×1024 pixels. The captured images used for training may include more than one image magnification and may include images of different pixel sizes. The deep learning framework 310 trained on a first mag/size may still perform co-culture analysis on images captured at other magnifications and at other sizes, whether or not such magnification and/or size imaged were included in the training image set. Example ranges of co-culture well magnification include: 5×-100× (or any option that the microscope allows). Example range for image sizes: 128×128 pixels to 2048×2048 pixels (or any option allowed by a photodetector). Further, the size of the input image can be changed by downsampling. The resulting brightfield images 302 were 2D projections of Z-stacks, with a range of 300 um in 15 um steps. These images 302 were provided to an organoid annotation process 312 prior to training, where that process included a human-in-the-loop annotation. In some examples, the organoid annotation process 312 applied an automated process to automatically generate annotations and then manually reviewing and editing those annotations was performed. The result is that the brightfield images 302 represent a range of experimental conditions: organoid-only images, organoid & PBMC co-cultures at high Matrigel concentration where organoids remained suspended and spherical, as well as organoid & PBMC co-cultures at low Matrigel concentration where organoids adhered to well plate surfaces, resulting in widespread morphologies. In total, in an example, the training dataset contained ~400 images. In various implementations, a dye may be used to distinguish immune cell types in training input images, for example, B cell and T cell lymphocytes to assist in the annotation of cellular therapies.

To generate segmentation labels in the images 302, in the illustrated example a pre-trained segmentation model 314 was used. In the illustrated example, that model 314 is configured with a machine learning algorithm and, more particularly, as a convolution neural network, such as a Mask R-CNN model. For example, the segmentation model 314 may be a pre-trained Mask R-CNN model trained from pre-training data 316. As a Mask R-CNN model, the model 314 is configured and trained to produce masks for each recognized object in the brightfield images 302. Therefore, in the illustrated example, training of the deep learning framework 310 is achieved using a human-in-the-loop annotation protocol where organoid segmentations were seeded using predictions from the pre-trained Mask R-CNN model 314. In an example, the pre-trained Mask R-CNN model was trained on the Kaggle 2018 Data Science Bowl nucleus dataset, and generalized readily to organoid brightfield images. These predictions were preloaded in a custom CellProfiler annotation pipeline 318 to be corrected by human annotators to generate the final ground truth organoid segmentation images 320. The resulting ground truth organoid segmentation images 320 were provided to the deep learning framework 310 for training, where in the described example all PBMCs were excluded from the annotations. Thus, the segmental model 314 may be trained on a public data set of organoid images, which may include fluorescence, brightfield, and stained histopathology images.

The deep learning framework 310 is trained as an imaging model, such as an artificial intelligence engine including one or more machine learning models or neural networks (e.g., models 322 and 324), trained to segment an input image into one or more targets and to generate an output 326 that may include a binary mask for the input image, a categorical mask (differentiating between organoids and one or more immune cell therapies), and/or a list of organoid locations, sizes, and/or degree of apoptosis. The deep learning framework 310, and the models therein 322 and/or 324 may include gradient boosting models, random forest models, neural networks (NN), regression models, Naive Bayes models, or machine learning algorithms (MLA). MLAs include supervised algorithms (such as algorithms where the features/classifications in the data set are annotated) using linear regression, logistic regression, decision trees, classification and regression trees, Naïve Bayes, nearest neighbor clustering; unsupervised algorithms (such as algorithms where no features/classification in the data set are annotated) using Apriori, means clustering, principal component analysis, random forest, adaptive boosting; and semi-supervised algorithms (such as algorithms where an incomplete number of features/classifications in the data set are annotated) using generative approach (such as a mixture of Gaussian distributions, mixture of multinomial distributions, hidden Markov models), low density separation, graph-based approaches (such as mincut, harmonic function, manifold regularization), heuristic approaches, or support vector machines. NNs include conditional random fields, convolutional neural networks, attention based neural networks, deep learning, long short term memory networks, or other neural models. While MLA and neural networks identify distinct approaches to machine learning and an artificial intelligence engine, the terms may be used interchangeably herein. Thus, a mention of MLA may include a corresponding NN or a mention of NN may include a corresponding MLA unless explicitly stated otherwise. A single instance of the above models, or two or more such instances in combination, may constitute a model for the purposes of models, artificial intelligence, neural networks, or machine learning algorithms, herein.

Figure 4:
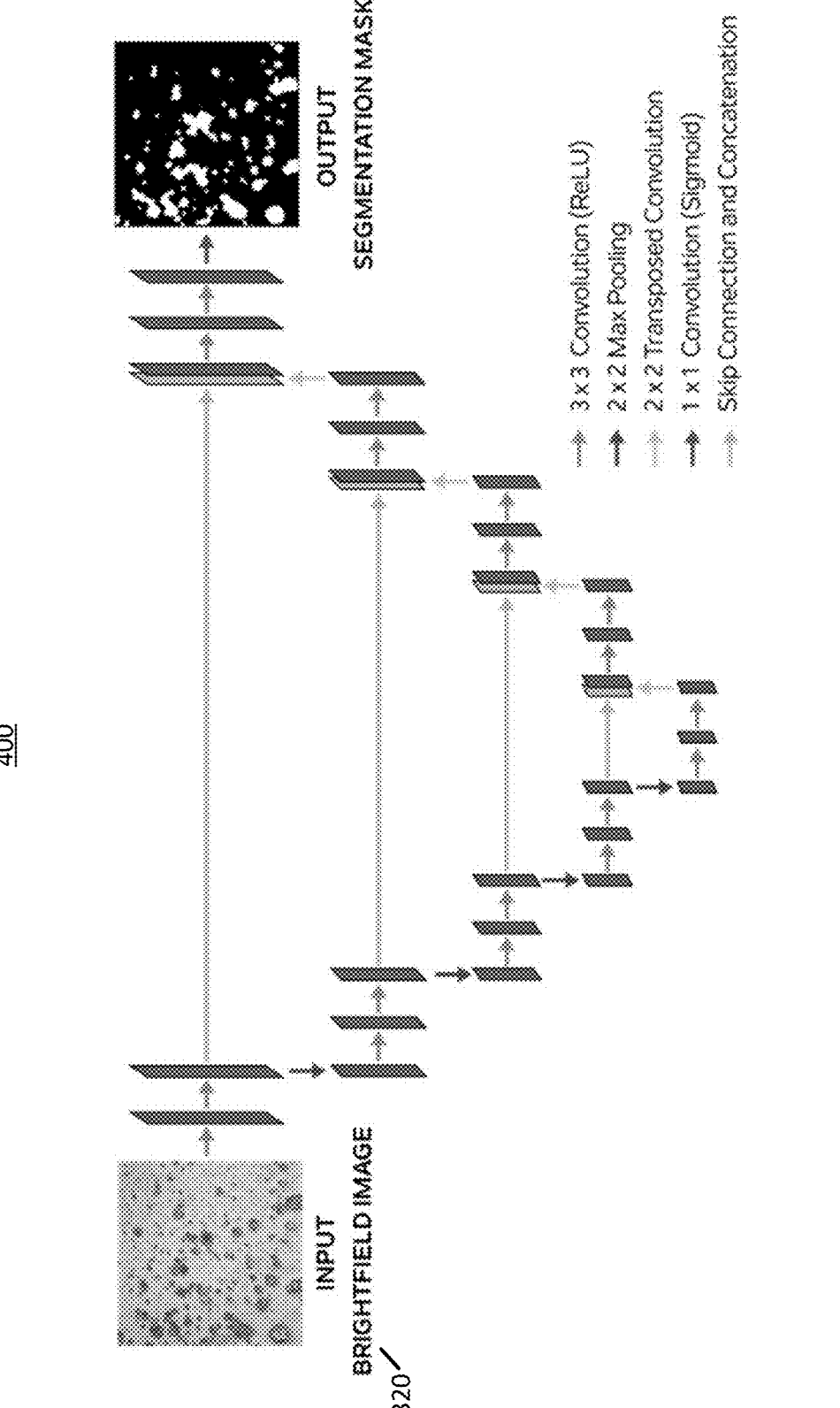
FIG. 4 is a schematic of an example machine learning algorithm configuration for classification and segmentation model of the architecture of FIG. 3, in accordance with an example.

In an example implementation, the deep learning framework 310 contains one or more machine learning algorithms to be trained, such as, for example, machine learning algorithms implemented in a UNET model and/or a mask R-CNN model. In an example, an organoid classification & segmentation model 322 may be configured as a UNET trained over 200 epochs using the Adam optimizer with a learning rate of 1e-3 and batch size of 2. An example UNET configuration 400 for the segmentation model 322 is shown in FIG. 4 where the input ground truth organoid images 320 are provided to train the UNET configuration 400 to generate an output segmentation mask. The UNET may have 16 features in the first layer, with 5 layers in total. In various implementations, a learning rate may be between 1e-1 and 1e-8, batch size between 1 and 20, number of layers between 3 and 9, and a number of first layer features between 4 and 1,024. In other examples, the organoid classification and segmentation models herein (322 and otherwise) may be configured as FCN.

Training annotations, e.g., performed at processes 312 and/or 318, may include identifying targets, varying degree of responders for differing cellular therapies or PBMCs (low, medium, high, or quantified response), fluorescent dye regions, and other targets.

Organoids are generally a three-dimensional (3D) collection of cells which may be imaged one slice at a time for each cellular layer in the organoid. The resulting 3D depiction of the organoid, or a flattened image, such as those generated via max projection may be generated which flattens each of the 2D images for an organoid into a single layer that may be contained as the training images 302.

In some examples, the training images 302 may include two corresponding images, consistent with a 2 channel brightfield image, both captured by the confocal imager 304 or each captured by different confocal imagers collectively represented by the imager 304 (such as, a brightfield imager and a fluorescent imager). For example, a first channel may include the organoid, the immune cell therapy, the background, and maybe artifacts. A second channel, alternatively called the fluorescent channel, may include the luminescence associated with the fluorescent dye. Both channels may be provided in series (or as a single concatenated image) to the deep learning framework, which may contain a single model, branch of a neural network, or other artificial intelligence engine. Or both channels may be provided to multiple models which are later combined. The images 302 may be provided in series with temporal component identifier, protocol identified by client, or other supplementary information such as metadata. In an example, different class weights for object/non-object classifications were used for training an organoid model (e.g., a class weight ratio of 2:1 for object/non-object) as compared to a training an immune model (e.g., a class weight ratio of 6:1 for object/non-object). Further, the training data may be gathered differently. For the organoid model, in an example, model-in-the-loop human annotations on brightfield images were gathered to generate the labels for the training set. For the immune model, labels were generated from counter-stained fluorescence images where only the immune cells were stained with a dye called CellTrace Far Red. Immune cell segmentation labels were then detected from these fluorescence images using a threshold-based segmentation method in CellProfiler.

Figure 6A:
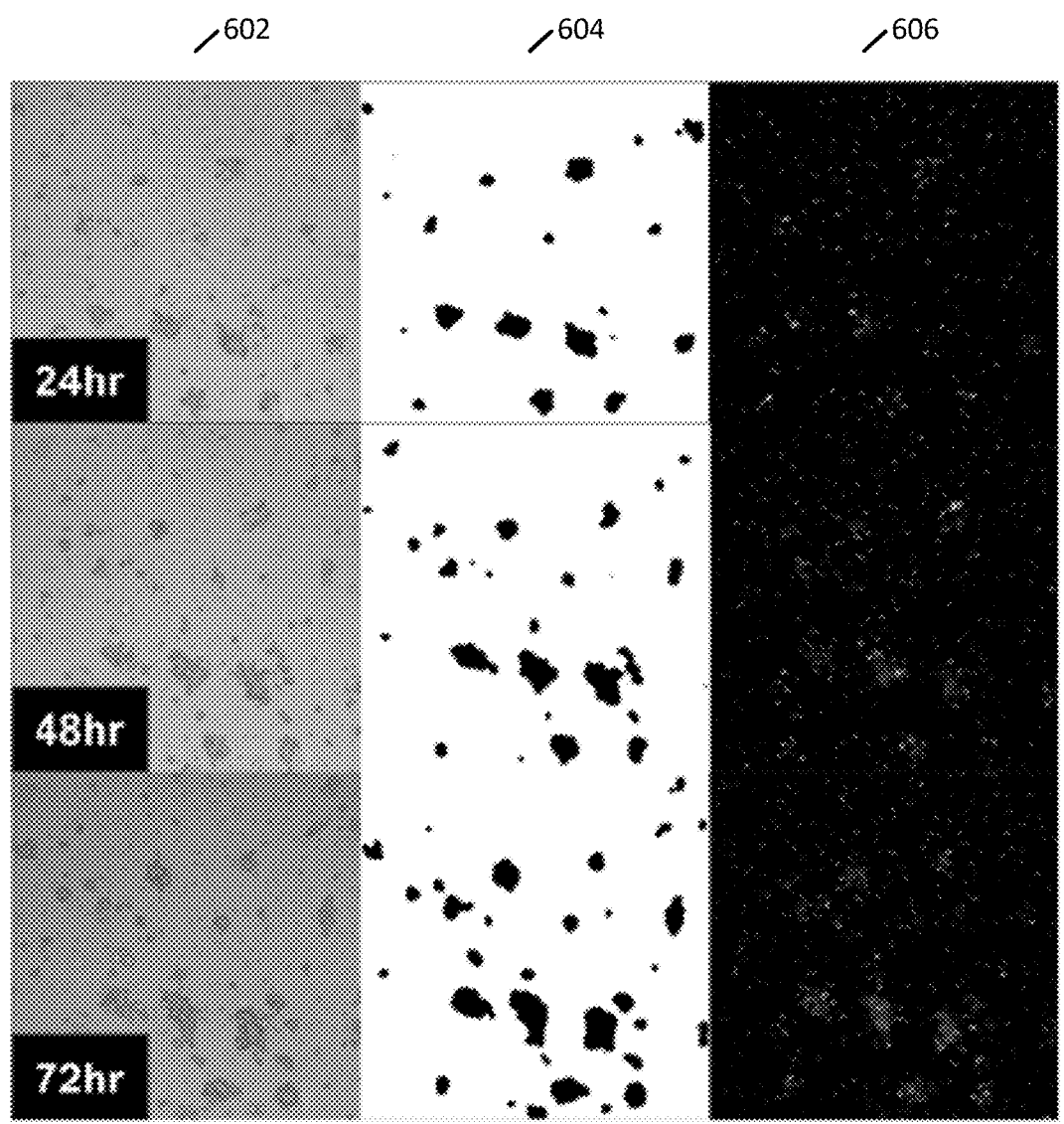
FIG. 6A are images of example brightfield images, generated mask, and processed fluorescence images, at different time periods, as may be generated by the co-culture analysis system, in accordance with an example.
Figure 6B:
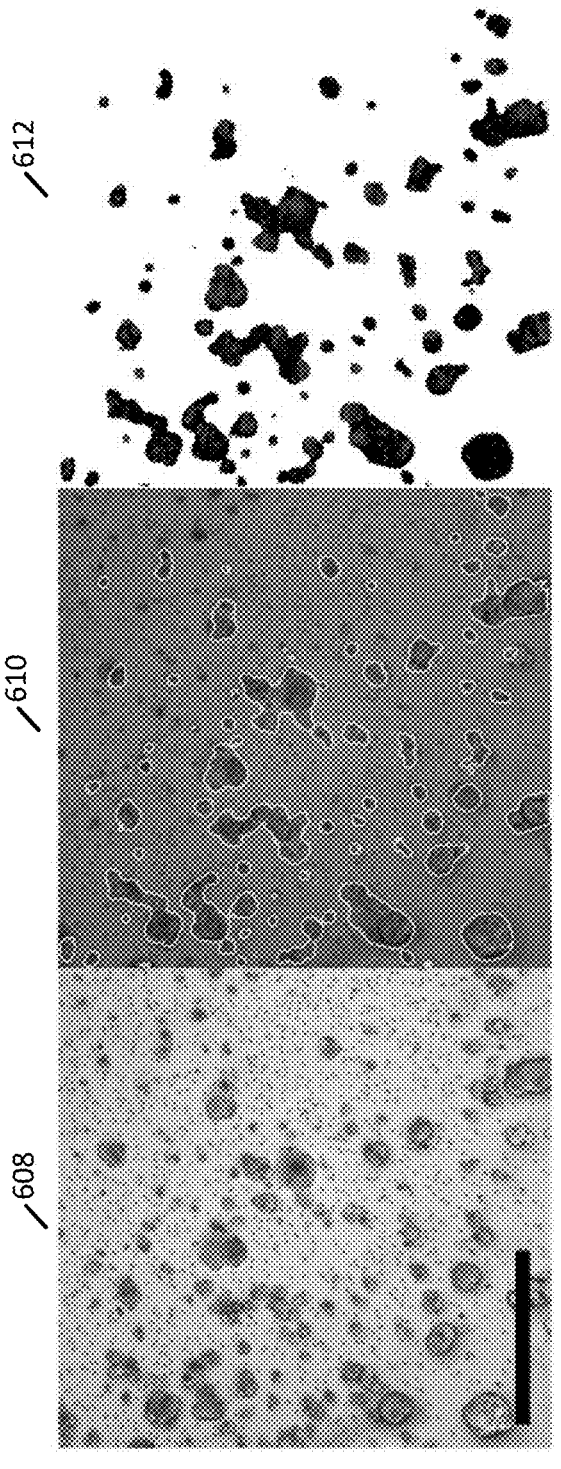
FIG. 6B are images of an example input brightfield image, organoid mask segmentation contours overlapped on a caspase fluorescence image, and the organoid-specific caspase mask, in accordance with another example.
Figure 7:
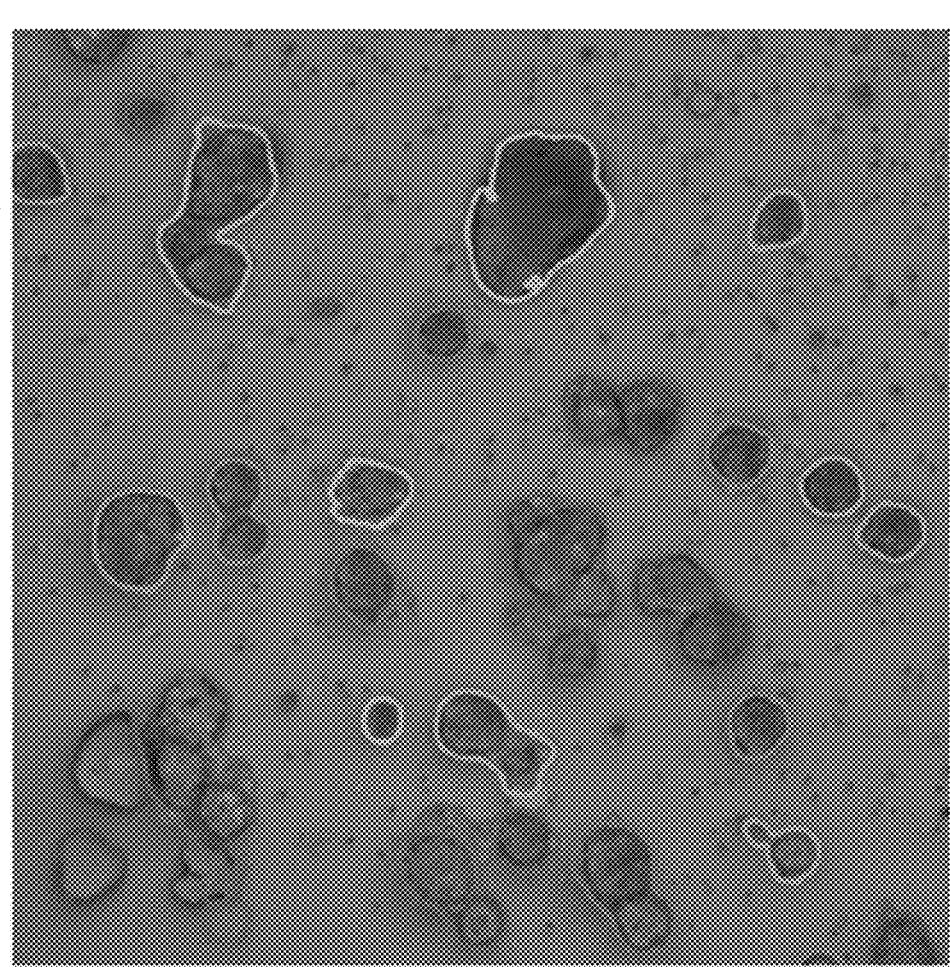
FIG. 7 is an image of an example categorical mask generated by a deep learning framework having multiple colored boundary identifiers rather than a binary mask, in accordance with an example.

In operation, the deep learning framework 310 may be trained to receive a 2 channel image, segment out only organoids using a mask, transfer the mask to the fluorescent channel and measure the cell death such as via pixel intensity quantification compared against threshold and then to count number of pixels exceeding the threshold within each target. In an embodiment, a resulting image contour may be delivered including, for example, a mask for both channels in a black and white representation such as depicted in FIG. 6A, a colored representation such as depicted in FIGS. 6B and 7, or a textual listing of organoids, sizes, and cellular death, which may be stored as the output 326. In another example, the model or a post processing quantification may generate a structured CSV file(s) and a summarization of the intensity of the organoids, such as via an overlay and/or structured CSV with a bar plot of intensities may be provided. A CSV may include pixel location of organoids, size of organoids, index of organoids, and/or apoptosis of organoids. Such output, if generated by the deep learning framework 310 may be stored as the output date 326.

In an example, the deep learning framework 310 may include a single branch, convolutional neural network to receive the input image and output a mask of that image. Training may include the annotated images 320 across different timepoints and organoid lines (such as organoids with different shapes). In another example, training may include annotated images 320 across different timepoints and specific organoid lines based upon the specific shape of the organoid. In some examples, a mask may be generated, such as a mask having black to represent background or non-target pixels, and having white as the target pixels (such as the organoid or immune cell based therapy).

In an example, organoids may be sparse within the image, and the organoid segmentation model 322 may be trained to lump any overlapping organoids into a single organoid. In another example, organoids may be dense with many overlaps, and the organoid segmentation model 322 may be trained to segment overlapping organoids from one another to improve model performance in a dense setting.

In yet another example, image input to the model may include a pixel array with a matrix of values [greyscale or RGB/RGBC; 256×256 px, 512×512, 1024×1024 or have non-uniform dimensions such as 256×512; 8 bit, 16 bit, 32 bit, or 64 bit].

Identifying the organoids, such as those called out in the model, may include counting the number of nuclei corresponding to each organoid and a separate count or percentage of those overlapping fluorescent dye pixels or identified via the number of pixels per organoid and the percentage of that organoid with fluorescence overlap.

Segmentation and quantification across two channels with time lapse identification may include centroid tracking across images that were observed over time. Targets are given an ID and then IDs are tracked over time. Immune cells are not masked in one implementation, but may be masked out in another embodiment. While the organoid segmentation model 322 and the immune cell classification & segmentation model 324 are illustrated separately, they may represent a combined, single trained classification model, and therefore references herein to either model are to be construed as a reference to a single, combined model as well. The segmentation model 322 may be trained to track which immune cell therapies move to surround organoids and which do not. While organoids do not move, the imaging is performed across wells in each slide, and an imaging apparatus may not return to the exact same location on each time, so a bit of error tolerance may be included knowing that the apparatus may returns to the same position within a number of pixels (such a 5 px, 10 px, or more). The effect of the imaging discontinuity may be reduced by increasing resolution of the imaging, so that the targets are substantially larger than the error tolerance in size, such as each target must be larger than 10 px in size for an error of 5 px so that tracking may be performed such as via nearest distance matching.

For the co-culture at well plate 308 that includes organoids and immune cell therapies, the model training may include dyes to take into account that immune cells are so high in number (typically 1000 s per image). A second dye which illuminates immune cells may be included and the new dye color similarly located in training by pairing each unstained slide with each subsequently stained slide to identify immune cell therapies within images and learn to track them without the dye. The immune cell segmentation model 324 may therefore be trained based on received images 320 with these dye locations annotated. The resulting mask generated by the trained deep learning framework 310 is a combined mask of organoid cells from the trained model 322 and immune cell therapies from the trained model 324 which may be stored as the output 326 and provided to quantification process (or another model, or the original segmentation model) to record multiple targets at once, such as both organoids and immune cell therapies. In an example, the immune cell segmentation model 324 may be trained by providing fluorescence images where immune cells (e.g., PBMCs) were tagged by immune cell (e.g., PBMC) specific stains. Then, applying fluorescence thresholding algorithm to these training images, any cell with fluorescence that satisfies the thresholding algorithm is considered an immune cell (e.g., PBMC). These fluorescence images with thresholding algorithm may then be applied to train the segmentation model 324. The segmentation model 324 may have a UNET configuration, FCN configuration, or any other suitable machine learning configuration, in accordance with the examples herein, as is the case for the segmentation model 322, as well.

In various embodiments, the segmentation performed by the trained imaging model (e.g., framework 310) may include classification such as identifying whether a particular object or cell is in an image, semantic segmentation such as identifying all pixels that comprise a particular object type or cell type, object detection such as identifying the location of each one of a particular object or cell type, and/or instance segmentation such as identifying all pixels that comprise each individual object or cell of a selected type.

In various embodiments, the images 302 or 320 in the training data may be selected such that all images were generated by imaging a particular culture well size (for example, wells from a 96-well plate, a 384-well plate, or a culture plate having a different number of wells), a particular average organoid size, organoids generated by a particular culturing method and/or having a particular morphology (for example, a particular size, density, roundness, sphericalness, etc.) or well location (for example, well bottom, matrigel adhered, suspended, etc.), organoid cultures having a particular percentage of cell death in the culture. In other embodiments, training data are selected such that the images include variety with respect to one or more of the following categories: culture well size, organoid morphology, location, and/or culturing method, cell death percentage. In an embodiment, each image in the training data may have one cell type. In another embodiment, each image in the training data may have two or more cell types. In another embodiment, each image in a subset of the training data may have one cell type and the other images in the training data may have two or more cell types.

In an example, hundreds of brightfield images of wells (e.g., from well plate 308) containing an organoid and immune cell co-culture were taken 0 hr, 24 hr, 48 hr, 72 hr, or 96 hr after combining the cell types (cultures) and/or IO therapy, each image was annotated using a CellProfiler brightfield-only annotation pipeline to generate a binary mask corresponding to each image (where a pixel in the mask has a 0 if an organoid is present in that pixel and a 1 if an organoid is not present), and the paired brightfield and mask images were used for training at least one image segmentation model.

In another example, hundreds of brightfield images of wells (e.g., from well plate 308) containing an organoid and immune cell co-culture and their corresponding binary masks were used to train a model, for example, the UNET configuration 400 for 200 epochs.

In various embodiments, steps are taken to avoid the merging of touching objects (for example, two objects that are touching in the brightfield image may appear as one object in the corresponding binary mask).

In various embodiments, Caspase-3/7 intensity calculations are performed for each organoid in an image (either the training images or the input images during operation). Custom background subtraction for caspase intensity may be performed such as, for example, by calculating the mode intensity of the image, identifying it to be a background intensity, and subtracting the background intensity from the intensity of each organoid, for each image to identify the intensity for each organoid.

In various embodiments, this subtraction is done to counteract the effect of the location of the organoid on the intensity of the organoid (for example, the proximity of the organoid to the edge of the well).

In various embodiments, nucleus stain+PBMC (or other immune cell) counter staining is used for organoid and/or immune cell segmentation.

Thus, as described, in some examples, a training dataset is generated by the system 300. An example training dataset may include hundreds or thousands of annotated images, where these training images result from using a segmentation model wherein organoids are segmented out and immune cells remain in the images. Another training data set may include images annotated with immune cells segmented out while organoids remain. Yet another training data set may include images annotated with both organoids and immune cells segmented out.

Figure 5:
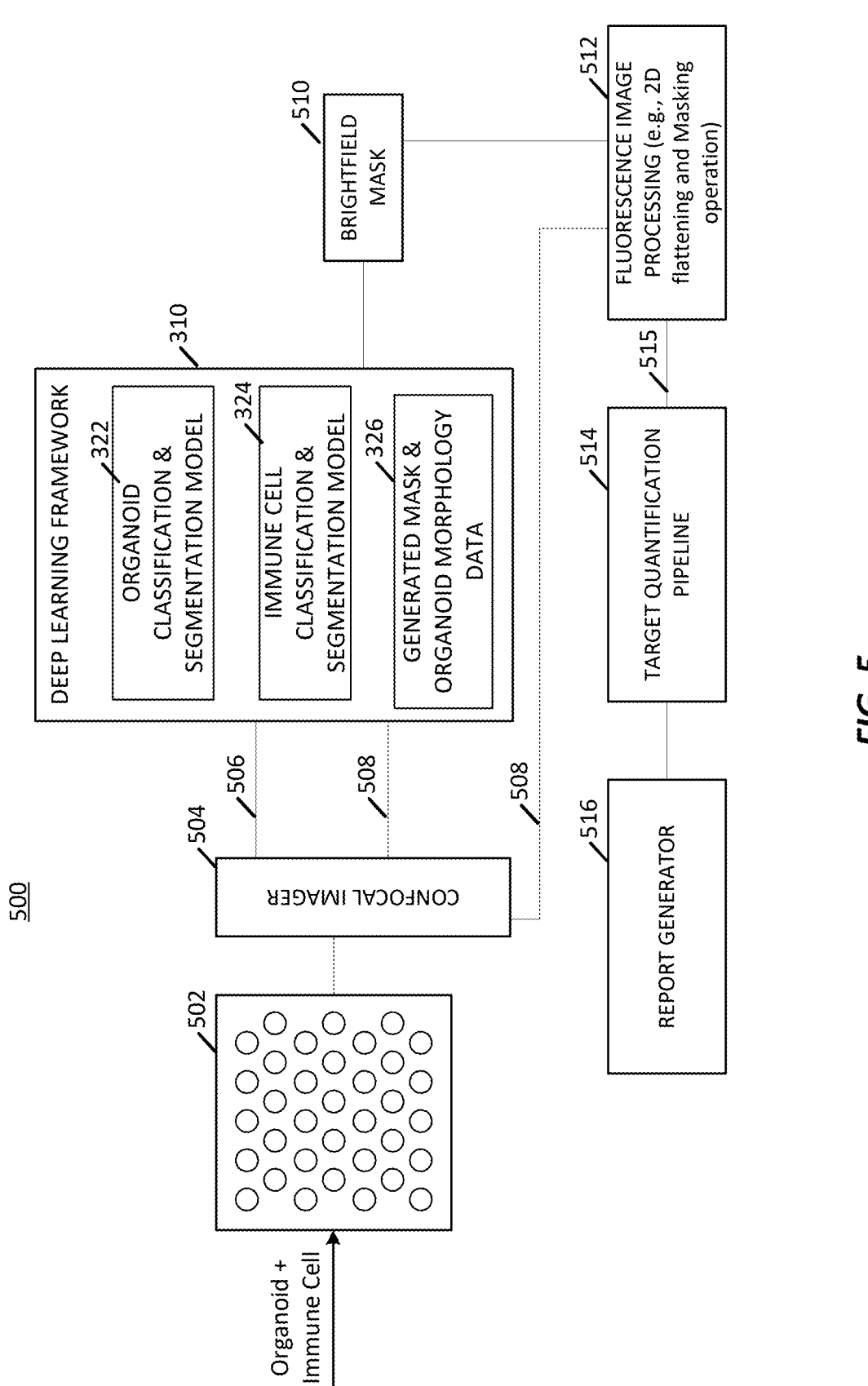
FIG. 5 is a schematic of an example architecture for implementing a deep learning framework of FIG. 3, in accordance with an example.

With the deep learning framework 310 trained, the trained organoid segmentation model 322 is able to receive input images of a co-culture of organoids and immune cells, generate segmented images separately identifying one or both of the organoids and immune cells and provide those segmented images to a post-processing pipeline for analysis. FIG. 5, for example, illustrates a configuration 500 of the deep learning framework 310. Organoid and immune cell co-cultures and created, for example, to assess an immune cell based therapy, and provided to a co-culture well plate 502, from which a confocal imager 504 obtains brightfield images 506 of the co-culture combinations and corresponding fluorescence images 508. The brightfield images 506 are provided to the deep learning framework and the organoid segmentation model 322 which generates organoid masks from these input images. In some examples, the brightfield images 506 are provided to the immune cell segmentation model 324 and the deep learning framework 310 generates a combined organoid and immune cell mask. In yet other examples, the brightfield images 506 are provided only to the immune cell segmentation model 324 and the deep learning framework 310 generates an immune cell mask. In any of these examples, the deep learning framework 310 generates a brightfield mask 510 identifying the organoid and/or immune cells and which is to be applied to the fluorescence images 508 at a fluorescence image processing 512, prior to processing quantification pipeline 514. In the illustrated example, the processing 512 is performed after the fluorescence images 508 are provided to the deep learning framework 310. In examples, all or part of the processing 512 occurs before provision to the deep learning framework 310. In some examples, the fluorescence images 508 are providing directly to the processing 512, instead. The processing 512 may perform a stacking process, such as a Z-stacking, on the received fluorescence images 508 to generate flattened fluorescence images of organoids within the co-culturing well 512. Different flattened images may be generated for each point in time to be examined by the configuration 500, e.g., to examine efficacy of an immune cell therapy over time. In some examples, the 3D images may be captured of the co-culture well plate 502, and the processing 512 may perform a flattening on the 3D images to generate flattened 2D images or the processing 512 may identify a slice on the 3D fluorescence images to generate a 2D fluorescence image from the slice of organoids within the first culturing well for each different time point. In the slice example, the processing 512 may identify the slice for use as the 2D fluorescence image based on position within the 3D space of the image, for example, at an upper surface, lower surface, or interstitial plane within that 3D space. In some examples, the processing 512 may determine image characteristics of the 3D image and determine a slice from those characteristics to generate the 2D image, such as my using as the 2D fluorescence image a slice that includes the largest two-dimensional area of targets (e.g., immune cells). The processing 512 may then apply the brightfield mask 510 to the processed fluorescence images and generate segmented fluorescence images 515 which are provided to the pipeline 514. The generated brightfield masks 510 may be binary masks indicating segmented organoid cells. The generated brightfield masks 510 may be binary masks indicating segmented immune cells. The generated brightfield masks 510 may be ternary marks that indicate organoid cells and immune cells.

The post-processing pipeline 514 is configured to receive the segmented fluorescence images and, depending on the configuration, calculate different quantification characteristics, in particular characteristics corresponding to changes in morphology of the organoid ell. In an example, the pipeline 514 determines average fluorescence intensity of the cell death marker per organoid using the following steps. First, the trained UNET model 322 was used to predict organoid segmentation masks from brightfield images. Then, these binary masks were separated into individual contours representing single organoids. These individual contours were filtered by size to eliminate 1-2 cell organoids that may be dead prior to imaging as well as any misclassified PBMCs from the final calculations. Then each individual mask was applied to the registered fluorescence image from which the quantification pipeline calculates the average cell death signal only within the contour of the organoid. In this example, the final result of the pipeline is the average cell death signal across all organoids for each experimental condition, which may be provided to a report generator 516. In this way, time-lapse data may be analyzed, for instance using a brightfield-only capture. The system 500 (as well as the other systems herein including system 100) can thus quantify organoid death or any number of organoid morphology changes, through analyzing heterogeneity and viability with fluorescence analysis.

The pipeline 514 may analyze the segmented fluorescence images to determine an amount of cell death per organoid. For example, the determination may be a quantification of cell death per organoid. In some examples, the system 500 may segment organoids to separate organoid signals from PBMC signals. In some examples, the processing 514 may determine a mean caspase fluorescence intensity per organoid.

FIG. 6A displays an example of corresponding brightfield, mask, and processed fluorescence images, at different time periods. The images 602 on the far left are an example of a brightfield image of an organoid and PBMC co-culture with caspase 3/7 fluorescent staining to indicate apoptotic cells (fluorescence not shown in brightfield image) and is repeated for three time frames of 24, 48, and 72 hours. Organoids may appear to grow in size over time even as they undergo apoptosis because the organoids naturally grow in size over the time span of the experiment due to the growth media supporting them. Additionally, cells dissociate and spread out during apoptosis and immune cells may attach to or even infiltrate the organoids. Subsequently, the masks for the input images may change over time to track the differing targets. For example, a mask for organoids may need to slightly expand while still tracking the same organoid, or a mask for immune cell therapies may move to track immune cells which are infiltrating the tumor cells of an organoid.

Subsequently, the corresponding images 604 in the center are masks of the organoid segmentations generated by the neural network (e.g., the organoid segmentation model 322) using brightfield images. This mask is applied to the fluorescence images 606 on the right to quantify the intensity of caspase 3/7 fluorescent staining in the organoids. In the images on the right, pixels having greater fluorescence intensity are white and pixels having less fluorescence intensity are black (the fluorescence image was captured in the same field of view as the brightfield image), therefore an intensity quantification for each tracked target may be performed.

FIG. 6B shows another example, with an input Brightfield image 608, organoid mask segmentation contours overlapped on a caspase fluorescence image 610, and the organoid-specific caspase mask 612. The organoid mask 612 is transferred over the caspase fluorescence image 610, masking out signals from background and from PBMCs allowing for standardized automated detection of organoid-specific caspase signals.

FIG. 7 illustrates another example categorical mask 700 generated by the deep learning framework 310 for organoids that may include multiple colored boundary identifiers rather than a binary mask. Instead of being binary, the mask 700 is an example of a color-coated boundary identifier mask, e.g., ternary or higher classification mask, generated as an overlay for the brightfield image. The mask 700 may use only a single color or multiple colors to identify and distinctly display differing targets, which are segmented out in the image (such as a first color for organoids and a second color for immune therapies, or a plurality of colors for each depending on the level of classification desired). In an example, the categorical mask 700 may segment an input image based on cancer organoid cells, different organoid cell types, and/or one or more types of immune cells. In some such examples, the trained segmentation models herein may be trained multi-class segmentation models, such as using a three-class or higher-class semantic segmentation fully convolution neural (FCN) network built upon a UNET architecture, as discussed in reference to the cell segmentation model of U.S. application Ser. No. 16/830,186, which is hereby incorporated by reference in its entirety. In one embodiment, that network would be trained on fluorescent, brightfield, and/or paired fluorescent and corresponding brightfield microscopy images.

Instant assays that may be implemented with the systems 100 and 500 and methods herein may be implemented in response to an analysis from an automated clinical decisional support system, such as in response to an immune infiltration machine learning framework as described in U.S. patent application Ser. No. 16/533,676, which is hereby incorporated by reference in its entirety. For example, if patient has low tumor infiltrating lymphocytes, e.g., as determined by the immune infiltration machine learning framework, a patient might not be designated as a good candidate for IO therapy. But that TIL measurement may just be a snapshot of the patient's tumor immune microenvironment (usually from a specimen that was collected before treatment, before immune cells were mobilized to infiltrate the tumor). The systems 100 and 500 and methods herein may measure for infiltration over time and then be used to determine that organoids from the patient are susceptible to immune cell mediated killing and the patient could be a good candidate for IO therapy. In another example, even if the patient has high TILs measured, the present techniques can be used as a way to narrow down the list of the most effective therapies that should be tried first for the patient.

Instant assays that may be implemented with the systems 100 and 500 and methods herein include establishing: the baseline ability of patient's T cells to recognize and kill organoids, for example, as a surrogate read-out of baseline anti-tumor immune activity; the baseline anti-tumor activity of patient T cells and patient organoids, which may be enhanced with checkpoint blockade antibodies; the impact of checkpoint blockade antibodies in T cell-tumor organoid co-culture, which may provide insight into the consideration of immunotherapy compared to other targeted therapies; the response an organoid may exhibit, such as reacting to immune cells, based on the organoid phenotype; and identifying and tracking immune cells over time to quantify cellular therapy migration toward the organoid, maintain proximity to the organoid, and/or kill the organoid. Identification and tracking may include concentrating immune cells in quadrants of the organoids may be performed, as well as tracking them individually using a similarity network.

For example, if the phenotype is quantifiable, systems and methods herein may be used to establish one or more thresholds that indicate which organoids are susceptible to an immune cell based therapy, such as a heterotypic cellular therapy with or without another immune-oncology therapy, and which are resistant. If a phenotype is categorizable, systems and methods herein may be able to establish one or more categories that indicate which organoids are susceptible to an immune cell based therapy, such as a heterotypic cellular therapy, with or without another immune-oncology therapy, and which are resistant. These thresholds may be useful for determining which patients to include or exclude in a clinical trial, or which patients are good candidates for receiving (predicted to respond to) a line of therapy, based on whether their tumor has characteristics that satisfy the threshold(s) and/or categories established by the systems and methods.

Instant assays, such as those supported by the systems 100 and 500 and the methods herein, may further include receiving a query about the efficacy of an immune cell based therapy, efficacy determined by cell death over time after applying differing concentrations of the immune cell based therapy, efficacy of immune cell based therapies may include or may be "built" or "designed" using car-T, car-NK, carmac, any effector cell used for killing cancer cells, immtac, tcr or T-cell engagers (for example, BiTEs), efficacy of other techniques for engineering immune cells which will attack and kill cancer cell organoids based on characteristics of the organoids, and characteristics of the organoids may include those derived from sequencing, analysis of histology slides, analysis of mass spectrometry results, analysis of protein composition, and other characteristics which may be visible from the surface of the organoid.

The systems 100 and 500 and methods herein may be used in establishing a database of organoid characteristics to identify the location of organoids within a laboratory setting based on their characteristics. Laboratories have a great many organoids which are derived from cancer biopsies of patients, and these organoids are isolated, grown, and provided to a number of testing procedures to generate a database, or library, of all the characteristics associated with each organoid. Then the organoids are stored in viably cryopreserved freezers until they are needed for use. Their locations: freezer, shelf, vials, etc. are recorded for ease of access in the future.

Figure 9A:
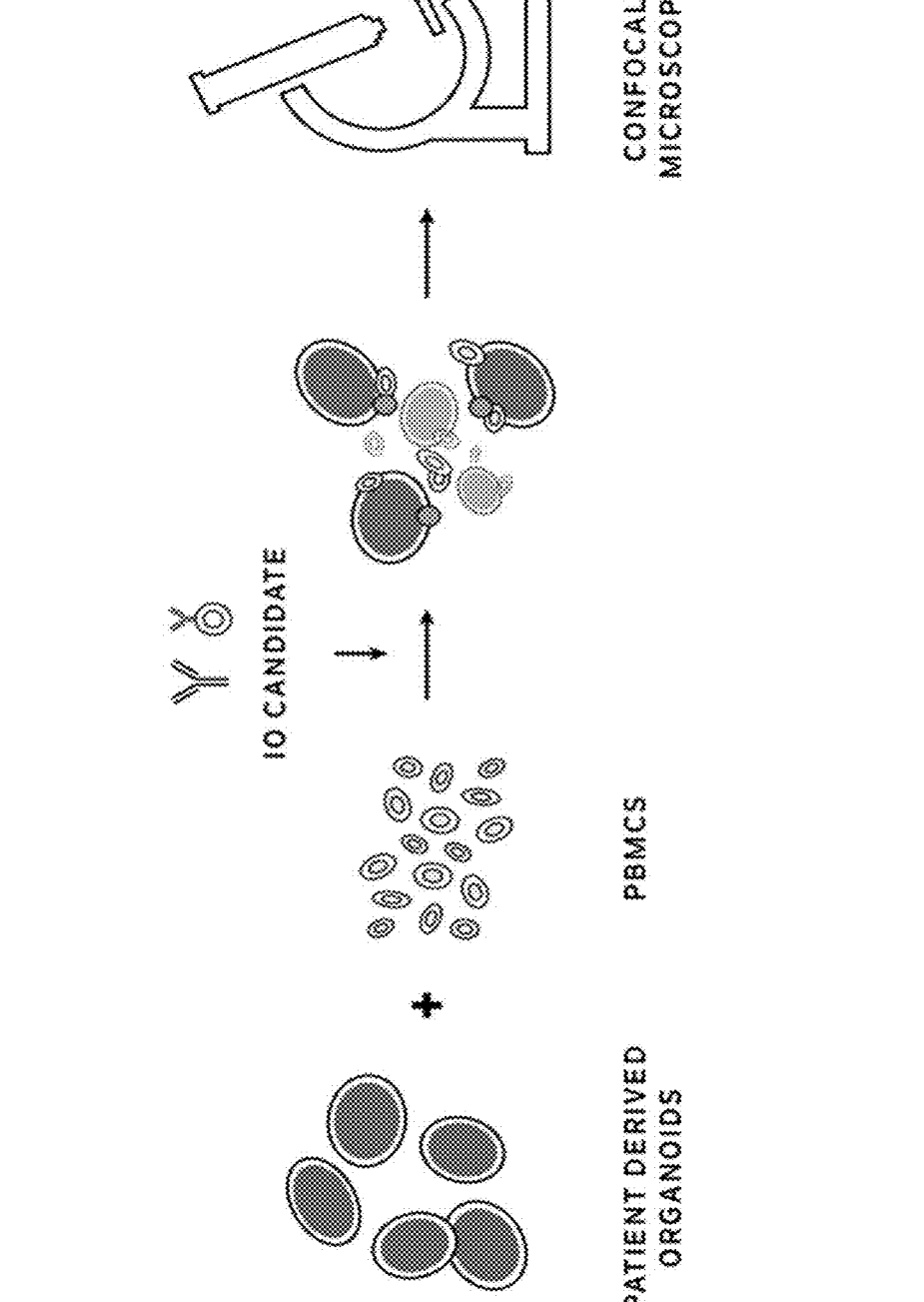
FIG. 9A illustrates an example process for co-culture generation, in accordance with an example.
Figure 9B:
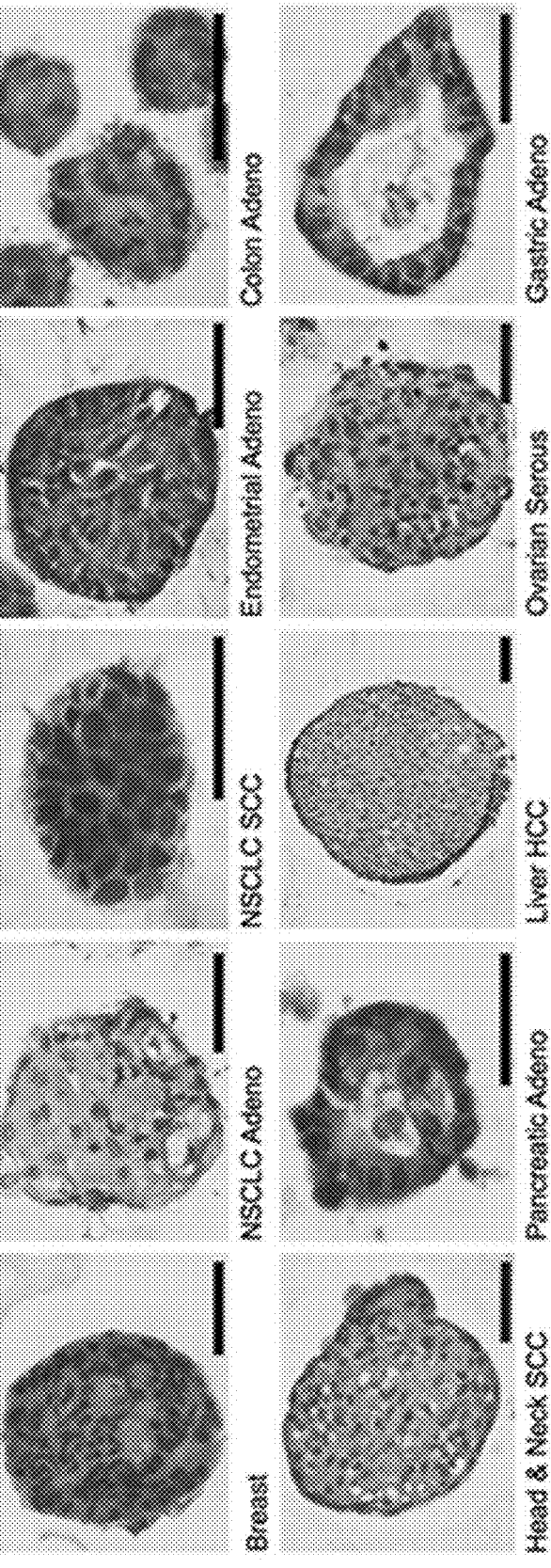
FIG. 9B are images of representative types of cancer organoid that may be co-cultured with immune cells.

FIGS. 8A and 8B illustrate an example process 800 for analyzing a co-culture formed of a combination of organoid cells and immune cells using a trained image model, such as may be implemented by the systems 100 and 500. Initially, cancer organoid cells and immune cells are selected at processes 802 and 804 respectively, for example, based on one or more cancer cell characteristics and/or one or more immune cell based therapies. In this regard, it is advantageous in various aspects to utilize an organoid sample and an immune cell sample which is as similar to a patient's tumor and immune cell population as possible (in the event that the tumor cells and/or immune cells are not originally isolated from the patient). An example workflow 900 is shown in FIG. 9A, showing patient derived organoids combined with PBMCs and candidate immune-oncology (IO) cell therapies to form a co-culture that is imaged by a confocal microscope or other imaging device. FIG. 9B illustrates examples of representative types of cancer organoid that may be selected and co-cultured with immune cells in various examples herein, as provided by Larsen et al., A pan-cancer organoid platform for precision medicine, Cell Reports, Vol. 36, Issue 4, 2021. Example characteristics and techniques for matching patient-derived organoids with immune cells include selecting PBMCs having similar characteristics as the tumor cells of the organoid (or patient), for example matching HLA type (HLA/MHC Class I alleles and serotypes; like, but not limited to subtypes: HLA-A*02:02, HLA-A*02:04, HLA-A*02:324, HLA-B*2701 to HLA-B*2728, C*01:04, C*03:07). Further example characteristics and techniques for matching patient-derived organoids with immune cells include the following.

In some examples, identification of organoid characteristics may be calculated by first growing the organoids and then sequencing the organoids to identify characteristics such as genetic variants, RNA transcripts, RNA expression levels, specific HLA or MHC type, epigenetic modifications, MSI (microsatellite instability) status, MMR (mismatch repair) deficiency, TMB (tumor mutational burden), or neoantigen predictions from nucleic acid sequencing data.

Identification of organoid characteristics may be calculated by first growing the organoids and then staining histological slides of the organoids to identify the presence of characteristics such as proteins of interest, particular sugar residues, proteoglycans, glycosaminoglycans, antigens that can be presented by class I or class II MHC/HLA, distinctions between glycans and lipids, cell surface molecules, aberrant gene product(s) directly or indirectly caused by mutation, or mutant enzyme not present in healthy cells (such as CEA on CRC cells, cancer testis antigens, magea4, magea3, CEA, CA-125, or CA-19-9), and the like.

Identification of organoid characteristics may be calculated by first growing the organoids and then performing mass spectrometry of the organoids (or other proteomic methods) to identify characteristics such as surface protein expression, post translational modifications, MHC presentation of peptide antigens or other MHC bound molecules, nucleic acid modifications (including DNA and RNA), or macromolecules such as proteoglycans and sugar residues on the cell surface.

Identification of organoid characteristics may be calculated by first growing the organoids and then performing Flow cytometry/Mass cytometry to identify characteristics such as surface and intracellular protein expression, which may be detected by antibody-conjugated stains.

In various aspects, the organoid is assayed for B2M (Beta-2-Microglobulin) expression.

Queries for characterization of organoids may include different modalities of data. When the modality is DNA, molecular information may be distinguished from a query such as a KRAS codon 12 missense mutation resulting in a neoantigen agnostic to HLA genotype, or a chromosomal rearrangement. When the modality is RNA, molecular information may be distinguished by transcript counts of (absolute presence or a threshold) aberrant expression of a cancer testis antigen/embryonic gene not normally expressed in an adult human such as NY-ESO-1, MAGE-A, SSX antigens, embryonic Fibroblast Growth Factors, etc. (see Scanlan M J, Gure A O, Jungbluth A A, Old L J, Chen Y T. Cancer/testis antigens: an expanding family of targets for cancer immunotherapy. Immunol Rev. 2002 October; 188:22-32. doi: 10.1034/j.1600-065x.2002.18803.x. PMID: 12445278.). When the modality is a protein target, molecular information may include identification of one or more protein products of the DNA or RNA as they exist in a solution. When the modality is a surface phenotype such as a sugar target, the molecular information may be an altered glycosylation residue on a surface protein or RNA molecule. In some examples, multiple modalities may be referenced together, such as using any of the above modalities to identify MHC allele restriction or a therapeutic which may be specific to a protein/peptide being presented on a particular MHC allele (for example, HLA A*01:01) if, for example, an antigen presentation is allele specific. Additional modalities may be included in the organoid characterization and may not be limited to molecular or genetic information.

In an example, organoid selection may include selecting for characteristics of an organoid that are expected to be indicators of the efficacy of an immune cell based therapy. Characteristics or characteristics expected during or after a co-culture assay may include: viability, apoptosis, cellular morphology changes, proximity of organoid to effector cells in the assay, effector cell density to organoid perimeter, effector cell penetration/infiltration into organoid, organoid proliferation, organoid size. In one embodiment, these features may be presented as a function of time.

In an example, querying the database for mature organoids such as those that are of sufficient size and satisfy the characteristic constraints identified. Due to the thorough documentation for each organoid, a query may be built that identifies, with particularity, the specific organoids needed to successfully conduct an efficacy analysis procedure.

In an example, organoid selection may include providing a map of where the organoids are located in the lab, and either manually or automatically collecting organoids for the upcoming "testing". A map may be a visual representation, a textual representation, or a combination of the two which identifies the location of all the organoids needed. The map may be optimized to show the most efficient route to follow to pick up all the vials needed.

In an example, immune cell selection may include providing a map of where the immune cells are located in the lab, and either manually or automatically collecting them for the co-culture. In instances where the immune cells are, themselves, an immune cell therapeutic, selection may include providing a map where the IO therapies are located in the lab, and either manually or automatically collecting them for co-culture.

A map, such as those provided by the organoid or immune cell selection may be a visual representation, a textual representation, or a combination of the two which identifies the location of all the organoids needed. The map may be optimized to show the most efficient route to follow to pick up all the vials needed.

Once collected, the immune cells may not be a perfect match with respect to the organoid or the patient. Additional steps may be taken to engineer the immune cells if needed.

In aspects of the disclosure wherein the immune cell based therapeutic is an adoptive cell therapy based on the immune cell, and the immune cell is not a "match" to the organoid or the patient, additional steps may be taken to engineer the immune cell to represent the exact immune cell therapy needed to satisfy the query. For example, an immune cell may be engineered to express a chimeric antigen receptor based on a T cell receptor sequence isolated from the patient. Engineering the immune cells to match the criteria of the immune cell based therapy may include first obtaining one or more commercially available cells or those that have been generated from patients or biospecimens received through a research agreement. These types of cells may include tumor infiltrating lymphocytes, peripheral circulating immune cells from blood, they can be derived from immortalized cell lines, they can be differentiated from iPS cells or Embryonic Stem cells. They could even be xenogenic i.e. non-human immune cells/effector cells. In another embodiment, these cells may be provided as a base cell and further engineering may be performed to limit the cells to those having one or more characteristics.

Figures 14A, 14B, 14C, 14D, 14E:
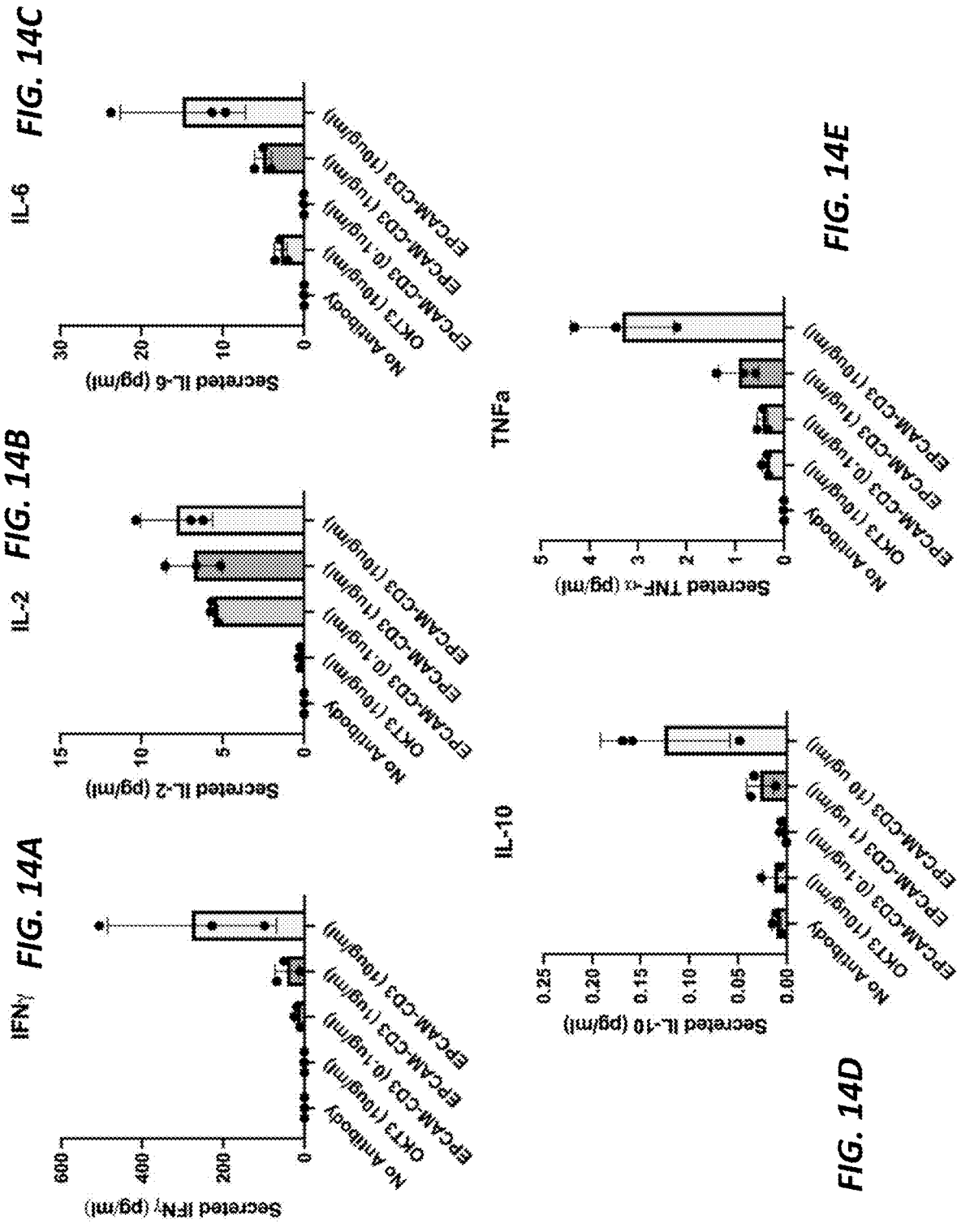
FIGS. 14A-14E are plots of profiles of secreted cytokines (interferon-gamma, IL-2, IL-6, IL-10, and tumor necrosis factor-alpha) for each of a number of different organoids and immune therapies, in accordance with an example.

At a process 806 the co-cultures are formed and at a process 808, the selected organoids, immune cells, IO therapies, growth mediums, and fluorescent dye(s) may be added to different wells in different concentrations to cover the range of concentrations, such as those described herein and/or depicted in FIG. 14. The differing concentrations are with respect to the organoids, the immune cells, and/or the IO therapies. For example, in an embodiment, the ratio of organoids to immune cells may be fixed while only the dosage of the IO therapy may be increased. In an example, the differing concentrations of the IO therapy may be 0.01 ug/ml, 0.1, ug/ml, 1 μg/ml, and 10 μg/ml.

At processes 810 and 812, images may then be taken by an imaging apparatus or device, such as a microscope for imaging slides, culturing wells, or petri dishes. In one example, an image may be generated at 512×512 pixels (such as for a 10× or 20× magnification); however, other sizes are available depending on the magnification of the image and user inputs.

These images may be brightfield images (process 810) and fluorescence images (process 812) and may be taken periodically, such as every hour, 6 hours, 12 hours, 24 hours, etc. Video may be taken from which still images may be extracted at different times. In another embodiment, the video may be analyzed for specific thresholds of cellular death or cellular therapy activity, such as tumor infiltrating lymphocytes invading the tumor cells of the organoid. Thresholds may be identified as concentration of lymphocytes in the organoids, concentration of the fluorescent dye for each organoid exceeding differing percentile, stand deviation, or cell count thresholds.

At a process 814, the captured images may then be sent to a trained imaging model (e.g., target segmentation model 118, organoid segmentation model 322, and/or immune cell segmentation model 324) for processing and generating (at a process 816) a mask of a target structure such as organoids, immune cell therapy, natural killer cells, lymphocytes, plasma cells, macrophages, monocytes, effector cells of myeloid lineage, effector cells of lymphoid lineage, effector cells from stromal/fibroblast lineage, cells from hematopoietic lineage, cells from mesenchymal lineage, or other targets.

At a process 816, the trained imaging model generates a segmentation mask (e.g., an organoid mask, an immune cell mask, or a combination thereof) and applies that mask to at least one type, or one channel, or the received input images, for example, to a fluorescence image channel. Image-derived data is determined and provided to a target quantification pipeline at a process 818, which receives the image-derived data and determines, at process 820, organoid phenotype and/or organoid morphology changes in response to the immune cell based therapies. The process 820 characterizing cancer organoid morphology change and or phenotype change may be executed by a machine learning algorithm, as described in various methods herein. A process 822 may display one or more fluorescent and/or brightfield images indicating the organoid morphology changes caused by the immune cell based therapy, and a report of the same may be generated at the process 824 (for example as may be implemented by report generators 124 or 516.

For example, at the process 824, report may be generated for providing the differing ratios of organoids to immune cells for each different concentration of IO therapies and the resulting apoptosis at different times to quantify the efficacy of which concentration and/or ratio best acts as an immune cell based therapy for the specific organoids, as determined by the pipeline at process 820.

The report may further include one or more brightfield, mask, and/or fluorescence images of the co-culture (which may be displayed at the process 822); results indicating which candidate therapies induced immune cell killing of cancer cells; results indicating which dose(s) of the candidate therapies induced immune cell killing of cancer cells; image/video of patient T cells interacting with/killing tumor organoids; impact of the percent increase of the addition of checkpoint blockade to the T cell/tumor organoid killing assay; or plots that compare tumor T cell killing to physiologically relevant IC50 curves for comparator targeted therapy or chemotherapy. A physician may reference a report and execute follow-up decisions based on their knowledge, experience, and treatment plan to decide to treat the patient with immunotherapy or other clinical candidate or to select clinical candidate (for example, immunotherapy) or targeted therapy as the next line of treatment. For example, when a patient has a similar cancer tumor as the organoids which were assayed with the immune therapy and/or IO therapy, where similarity may be based on comparing characteristics of the tumor and organoids.

Reports generated by the process 824 may include a summary of the assay. For example, organoids from a patient's specimen (tumor biopsy) are cultured as patient-derived organoids. Peripheral blood may be received and from which PBMCs may be isolated. Once the patient's organoids and the T cells are cultured successfully, the combination may be co-cultured. In one example, some baseline organoid killing activity may exist upon the first introduction of the co-cultured cells, but greatly increased activity may be observed when an IO therapy such as anti-PD-1 antibodies are added to the co-culture system. Furthermore, the dose-response curve anti-PD-1 and increasing T cells vastly outperforms physiologically relevant dose-response curves of alternative IO therapies such as palbociclib, olaparib, and pazopanib, or other IO therapies which have cytotoxicity to tumor organoids. Based on the efficacy identified in the report, the patient may be matched with anti-PD-1 therapy by their physician with confidence of an improved response to therapy.

Reporting generation at the process 824 may include generating a time-lapse imaging of the characterized cancer organoid cell deaths and/or the immune cells at the different time points and/or identifying organoids resistant to the immune cell based therapy and/or organoids susceptible to the immune cell based therapy based on the changes in the characterized cancer organoid cell death over the different time point, where such determinations were made at the process 824 or at the process 820.

FIG. 10 illustrates an example process 1000 as may be performed by a quantification pipeline, such as the pipelines 120 and 514. Segmented images of co-culture wells are received at a trained segmentation model (such as the target segmentation model 118, organoid segmentation model 322, and/or immune cell segmentation model 324) over a series of different points in time, for example, according to a timeline protocol (such as images captured every 12 hrs, 24 hrs, 48 hrs, etc. over some window of time). The images are buffered and tracked (which may include registration of images over time if needed), in particular to identify and track immune cells at a process 1004 and organoid cells at a process 1006 over the points in time and determine changes in morphology (shape, size, 2D area, 3D volume size, surface area, surface sharpness, and/or surface smoothness, etc.). For example, the process 1006 may identify organoid cells in images captured at a first time and organoid cells in images captured at a second time and perform a segmentation and registration of the images as a whole and/or localized segmentation and registration (e.g., at the organoid level) to identify the same organoids between the different images, from which changes in morphology are determined and then quantified and stored in a report and/or visualized to a user via a graphical display. From that tracking any number of quantification metrics may be determined from changes in morphology measured from such tracking, at process 1008. Example quantification metrics include: cellular therapy migration toward the organoid, changes in proximity of the immune cell to the organoid, organoid death, number and/or percentage of cancer cells affected by the IO therapy, change in cancer cell proliferation, change in organoid proliferation, and/or percentage of cancer cells that underwent apoptosis.

Figure 11:
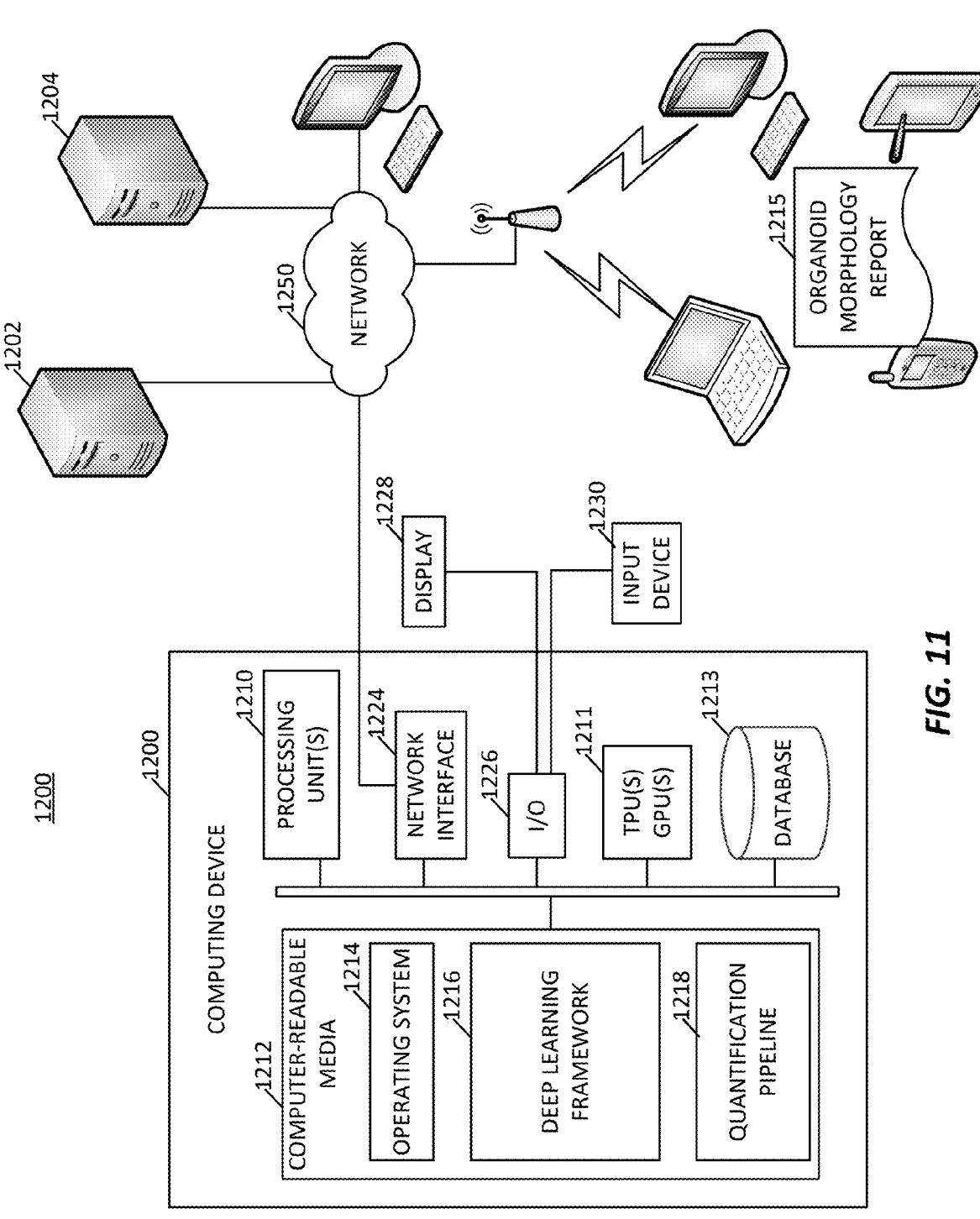
FIG. 11 illustrates a schematic of an example computing device for implementing image-based co-culture analysis systems, in accordance with an example.

FIG. 11 illustrates an example computing device 1200 for implementing the image-based co-culture analysis systems 100 or 500 of FIG. 1 and FIG. 5, respectively. As illustrated, the systems herein may be implemented on the computing device 1200 and in particular on one or more processing units 1210, which may represent Central Processing Units (CPUs), and/or on one or more or Graphical Processing Units (GPUs) 1211, including clusters of CPUs and/or GPUs, and/or one or more tensor processing unites (TPU) (also labeled 1211), any of which may be cloud based. Features and functions described for the systems 100 and 500 may be stored on and implemented from one or more non-transitory computer-readable media 1212 of the computing device 1200. The computer-readable media 1212 may include, for example, an operating system 1214 and the deep learning framework 1216 having elements corresponding to that of deep learning framework 310 or the trained target segmentation model 118, including the trained segmentation models 322 and 324. These and other models herein are implemented as executable code, for example, in separate executable software applications, in one or more software applications, or in hardware, and in a single computing device or across multiple computing devices. The media 1212 may include a quantification pipeline 1218. More generally, the computer-readable media 1212 may store trained deep learning models, executable code, etc. used for implementing the techniques herein. The computer-readable media 1212 and the processing units 1210 and TPU(S)/GPU(S) 1211 may store image data, cell classification data, cell segmentation data, organoid classification data, organoid segmentation data, and other data herein in one or more databases 1213. The computing device 1200 includes a network interface 1224 communicatively coupled to the network 1250, for communicating to and/or from a portable personal computer, smart phone, electronic document, tablet, and/or desktop personal computer, or other computing devices. The computing device further includes an input/output (I/O) interface 1226 connected to devices, such as digital displays 1228, user input devices 1230, etc. In some examples, as described herein, the computing device 1200 generates a report as an electronic document 1215 that can be accessed and/or shared on the network 1250. In the illustrated example, the system is implemented on a single server 1200. However, the functions of the system may be implemented across distributed devices 1200, 1202, 1204, etc. connected to one another through a communication link. In other examples, functionality of the system may be distributed across any number of devices, including the portable personal computer, smart phone, electronic document, tablet, and desktop personal computer devices shown. In other examples, the functions of the system may be cloud based, such as, for example one or more connected cloud TPU(s) customized to perform machine learning processes. The network 1250 may be a public network such as the Internet, private network such as a research institution's or corporation's private network, or any combination thereof. Networks can include, local area network (LAN), wide area network (WAN), cellular, satellite, or other network infrastructure, whether wireless or wired. The network can utilize communications protocols, including packet-based and/or datagram-based protocols such as internet protocol (IP), transmission control protocol (TCP), user datagram protocol (UDP), or other types of protocols. Moreover, the network can include a number of devices that facilitate network communications and/or form a hardware basis for the networks, such as switches, routers, gateways, access points (such as a wireless access point as shown), firewalls, base stations, repeaters, backbone devices, etc.

The computer-readable media 1212 may include executable computer-readable code stored thereon for programming a computer (e.g., comprising a processor(s) and GPU(s)) to the techniques herein. Examples of such computer-readable storage media include a hard disk, a CD-ROM, digital versatile disks (DVDs), an optical storage device, a magnetic storage device, a ROM (Read Only Memory), a PROM (Programmable Read Only Memory), an EPROM (Erasable Programmable Read Only Memory), an EEPROM (Electrically Erasable Programmable Read Only Memory) and a Flash memory. More generally, the processing units of the computing device 1300 may represent a CPU-type processing unit, a GPU-type processing unit, a TPU-type processing unit, a field-programmable gate array (FPGA), another class of digital signal processor (DSP), or other hardware logic components that can be driven by a CPU.

Figure 12:
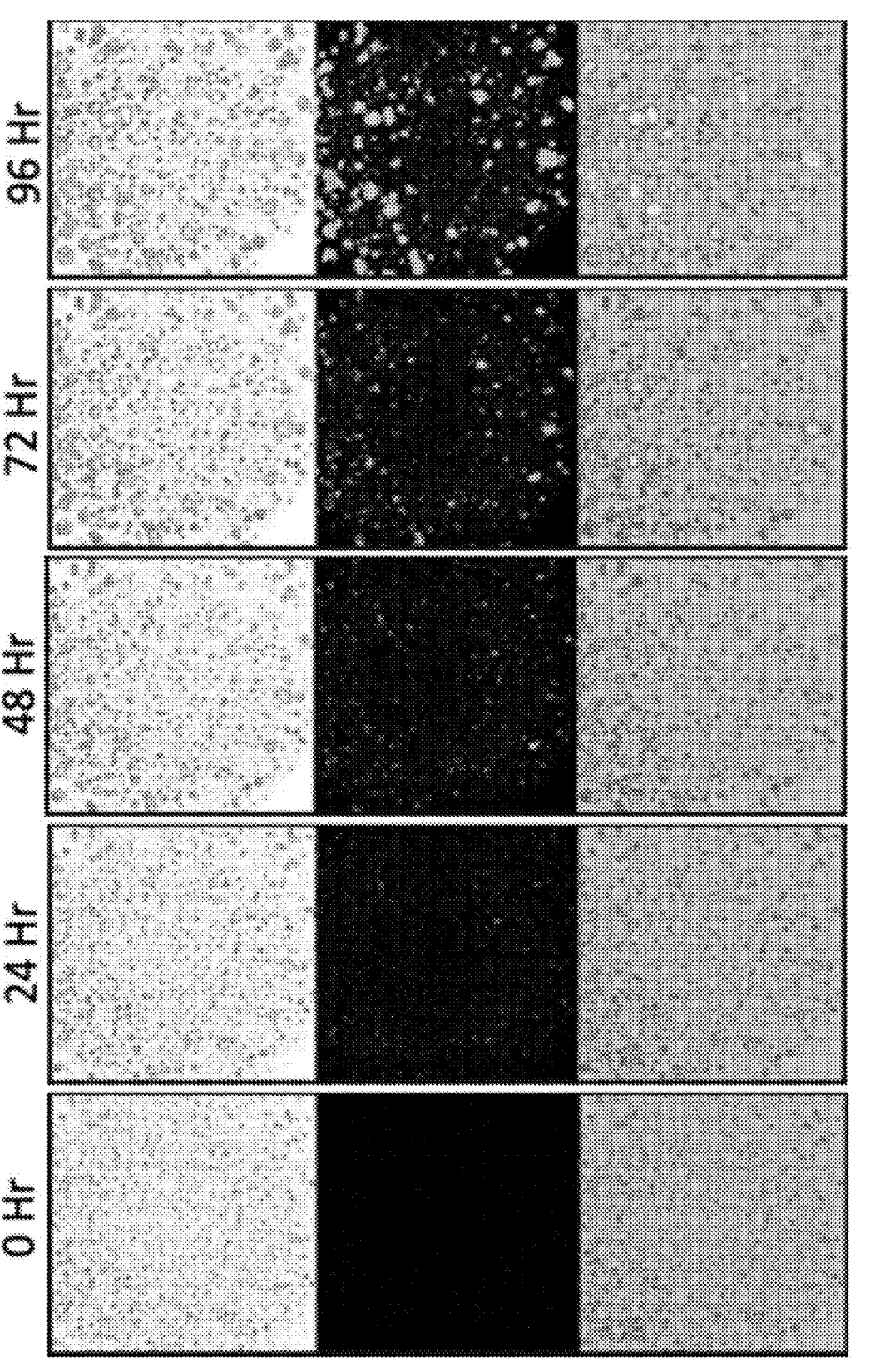
FIG. 12 illustrates brightfield images (top), caspase fluorescence images (middle), and overlaid images with segmentation mask (bottom), at different times, in accordance with an example.
Figure 13:
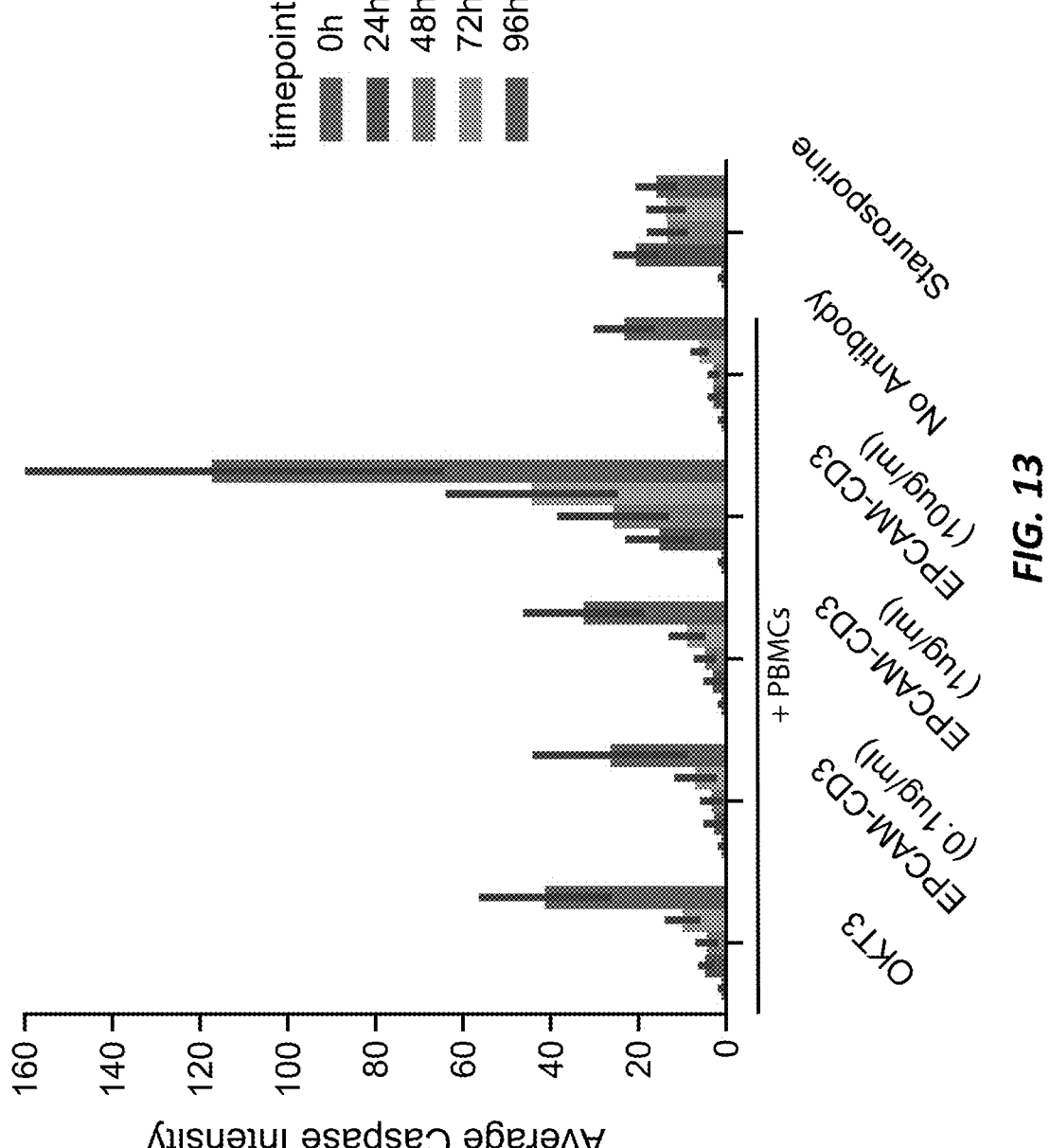
FIG. 13 are plots of average caspase intensities over time for each of a number of different organoids and immune therapies, in accordance with an example.
Figure 15:
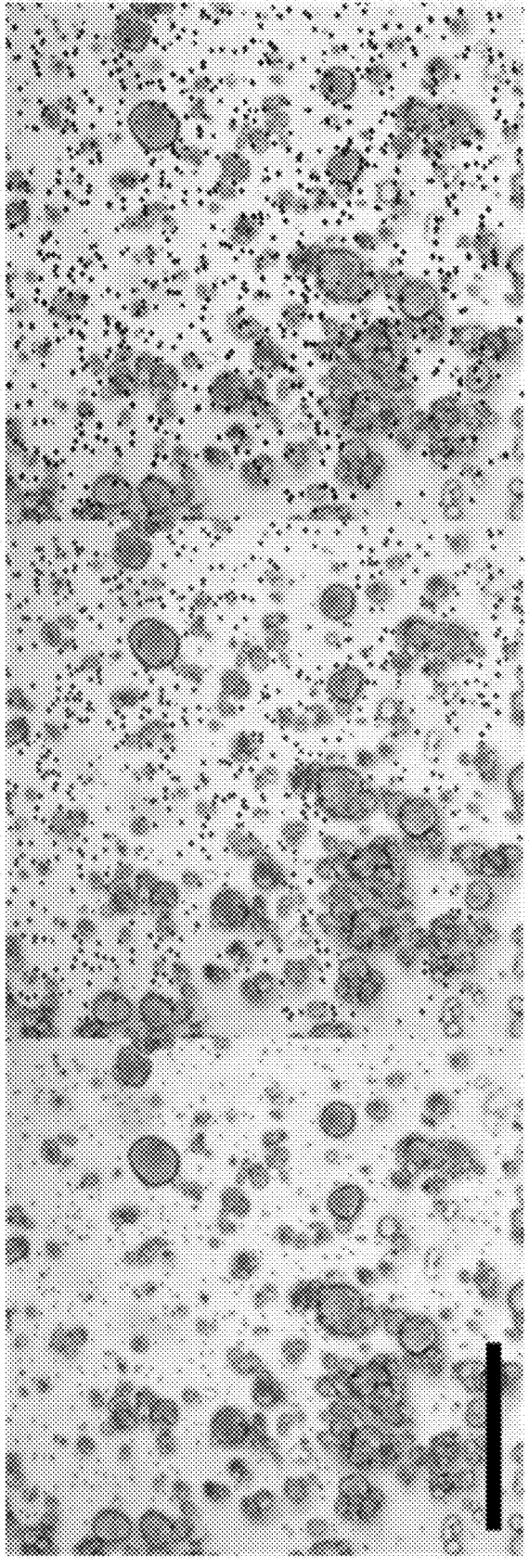
FIG. 15 are an input brightfield image, a ground truth peripheral blood mononuclear cells (PBMC) mask overlay, and a resulting PBMC mask generated by a trained segmentation model of an image-based co-culture analysis system, in accordance with an example.
Figure 16A:
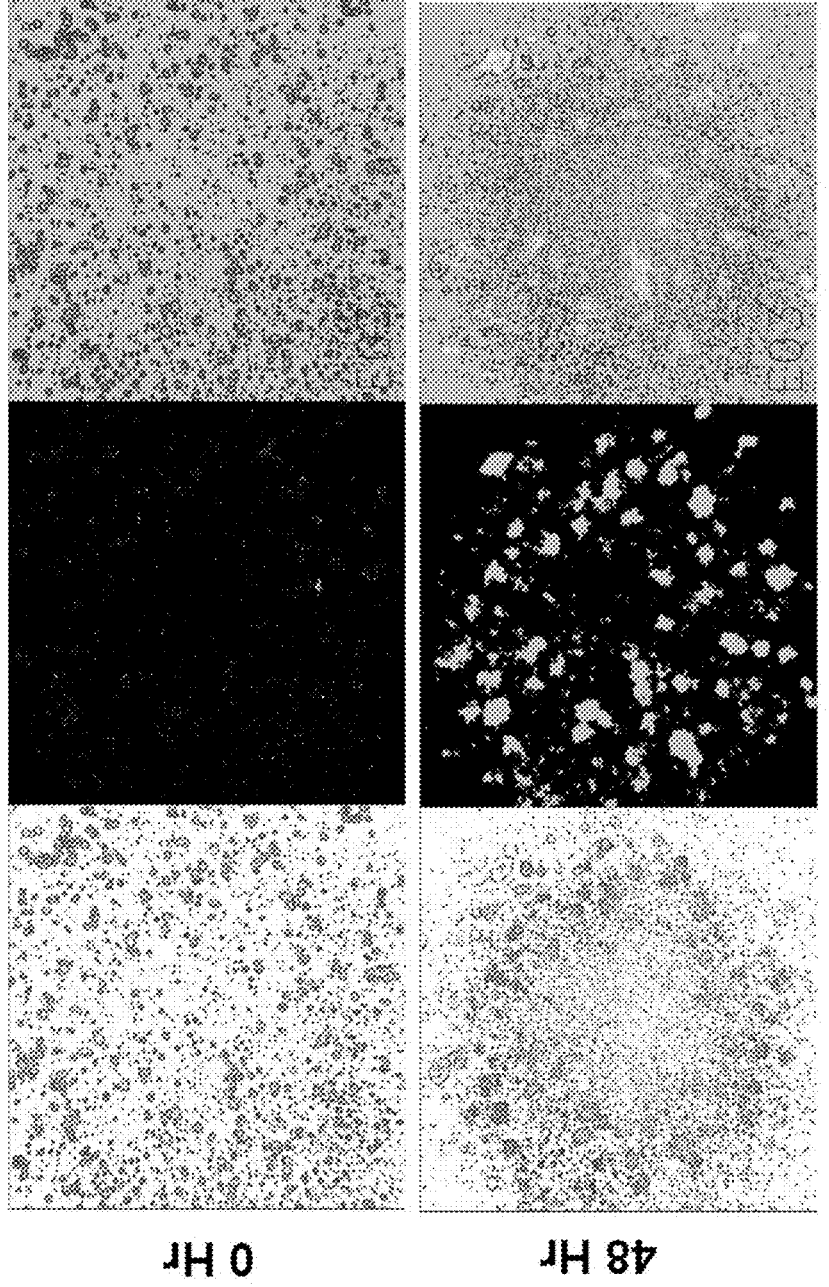
FIG. 16A are an input brightfield image, generated binary mask, and overlay segmented image, at two different time periods, for a co-culture of tumor organoids co-cultured with HER2-CAR-T cells in the presence of caspase-3/-7 green apoptosis assay reagent and imaged for brightfield and caspase dye to monitor organoid killing, in accordance with an example.
Figure 16B:
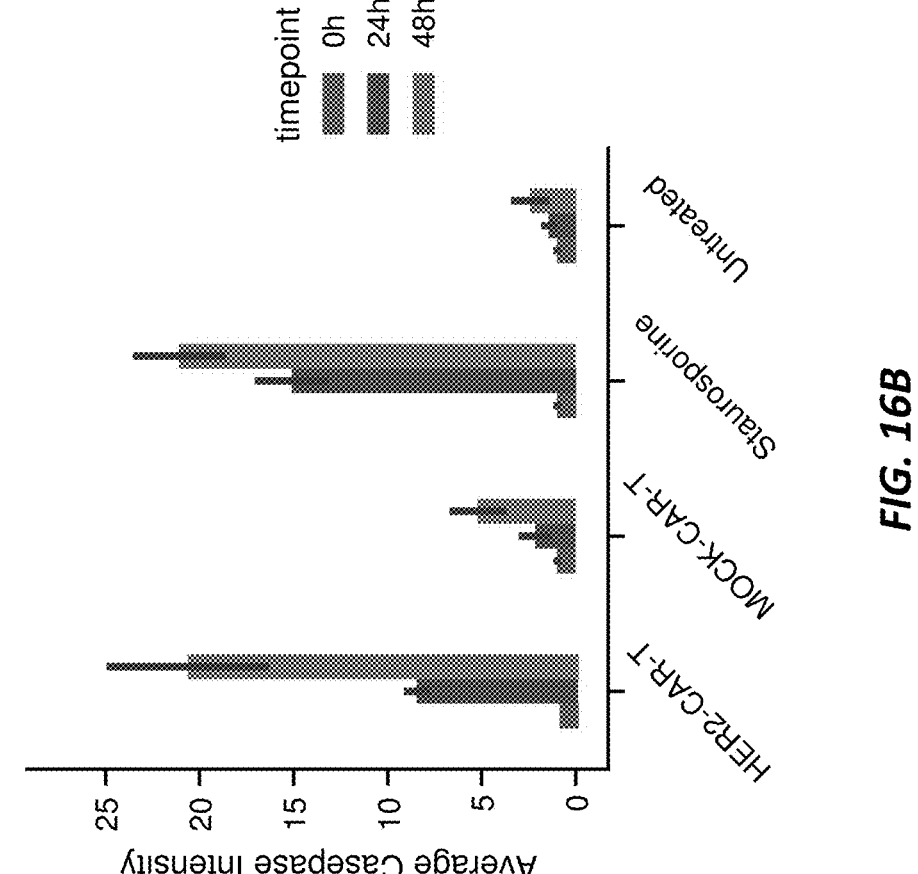
FIG. 16B is a plot of caspase channel intensities quantified for each of the organoids and aggregated across time and various treatments.

FIGS. 12-16 illustrate different experimental results obtained from using the systems and methods herein. Patient-derived tumor organoids were co-cultured with PBMCs in the presence of engagers/activators and vital dyes, and incubated in time course studies. The engagers/activators included the OKT3 antibody targeting CD3 and a bispecific antibody targeting CD3 and EPCAM (epithelial cellular adhesion molecule). Caspase dye was measured using fluorescent pixel intensities at different time points using high throughput imaging. A fully convolutional neural network was trained on 374 examples to segment out organoids from brightfield images comprised of organoids, immune cells and potential background artifacts. This segmentation mask was then transferred to registered caspase images to quantify tumor cell specific phenotypes in an automated manner. FIG. 12, illustrates whole co-culture well time lapse images (0 hrs, 24 hrs, 48 hrs, 72 hrs, and 96 hrs) with input brightfield images (top), caspase fluorescence images (middle), and overlaid images with segmentation mask (bottom). FIG. 13 is a plot of average caspase intensity over time for different time points (0 hrs, 24 hrs, 48 hrs, 72 hrs, and 96 hrs), where the caspase intensities are quantified for each of the organoids and aggregated across time and various IO therapies. Thus, the time-lapse imaging assay using the present systems and methods allows for quantification of the kinetics of engagers/activators in comparison to controls, resulting in accurate and precise technical reproducibility. FIGS. 14A-14E are plots showing profiling of secreted cytokines (interferon-gamma, IL-2, IL-6, IL-10, and tumor necrosis factor-alpha). The cell culture supernatants were harvested at different intervals of time and were analyzed for cytokine release using a custom V-PLEX biomarker panel from Meso Scale Discovery. FIG. 15 illustrates an input brightfield image (far left), a ground truth PBMC mask overlay (middle), and a resulting PBMC mask generated by a trained segmentation model (such as models 118, 322, and/or 324) showing PBMCs segmented from organoids and background, enabling colocalization and organoid-cell interaction studies. FIG. 16A illustrates an input brightfield image, generated binary mask, and overlay segmented image, at two different time periods, for a co-culture of tumor organoids co-cultured with HER2-CAR-T cells in the presence of caspase-3/-7 green apoptosis assay reagent and imaged for brightfield and caspase dye to monitor organoid killing. FIG. 16B is a plot of caspase channel intensities quantified for each of the organoids and aggregated across time and various treatments. Remarkably, immune cells and target cells were accurately distinguished without the need for cell labeling with chemical or transgenic markers.

Figure 17:
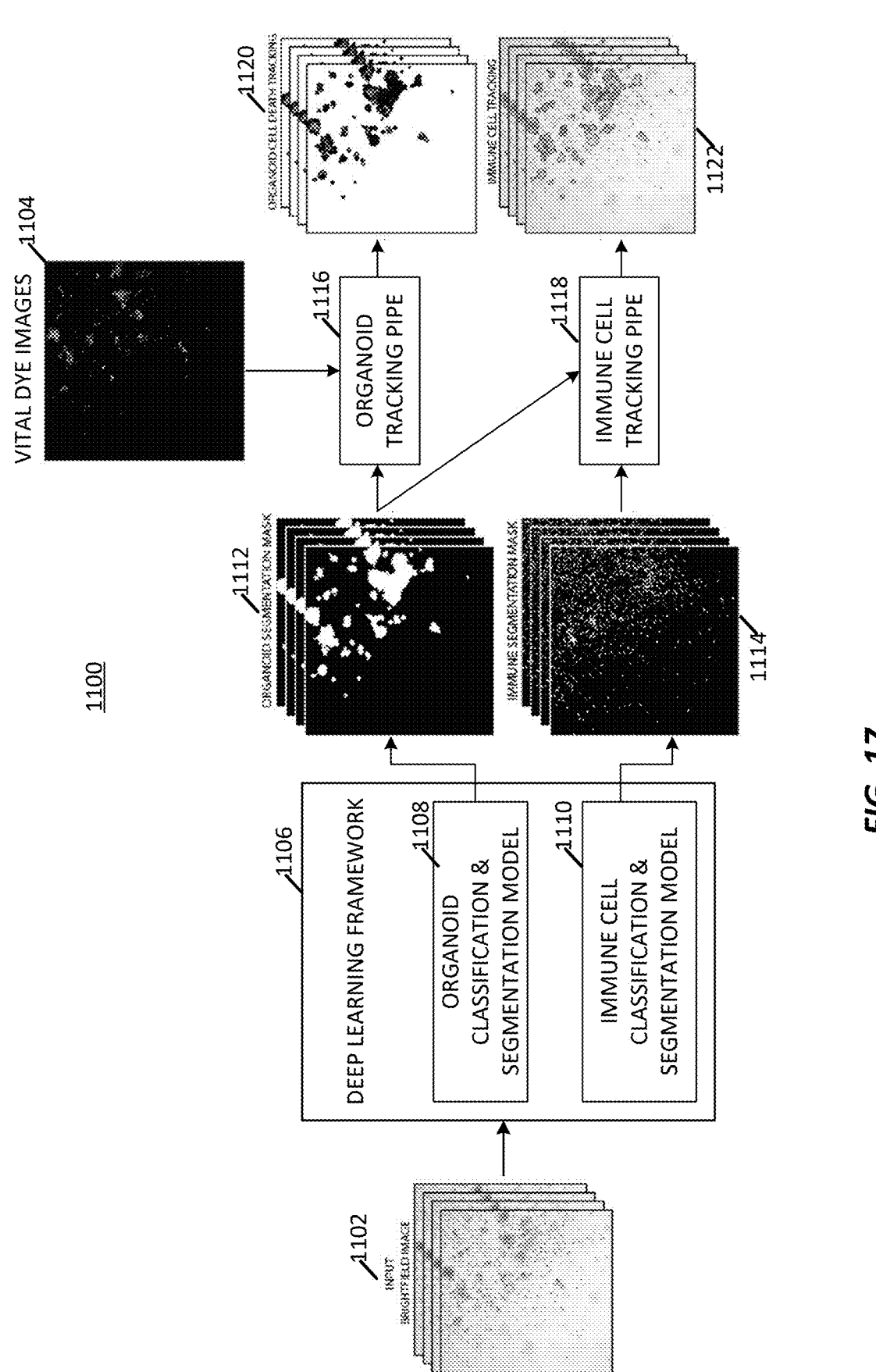
FIG. 17 is a schematic of another example co-culture analysis system, configured to identify organoid cells and immune cells within captured images, in particular using a single imaging modality, brightfield images, in accordance with an example.

FIG. 17 illustrates another example co-culture analysis system 1100 configured to identify organoid cells and immune cells within captured images, in particular using a single imaging modality, brightfield images in the illustrated example. The system 1100 may be used to measure tumor organoid response using time-lapse microscopy in co-culture assays. As with other techniques herein, these assays can be used to evaluate patient-derived tumor organoids with CAR-T cells or allogeneic MHC-matched PBMCs enhanced by T cell engager bispecific antibodies (generically referred to as "immune cells" herein). These assays allow us to quantify tumor organoid cell death via a vital dye stain while simultaneously providing insights into the kinetics of the killing by the immune cells.

As with other techniques herein, the system 1100 uses multi-channel, high-content imaging for co-culture assays providing a scalable and automated computational pipeline to process input images. The system 1100 is able to quantify tumor organoid cell death over time and correlate that cell death to immune cell kinetics over time. More particularly, the system 1100 is able to avoid the nonspecific phototoxicity and immune cell function impairment that can occur from fluorescent cell labeling imaging. In particular, a deep learning framework from multiple neural networks are used, a neural network to identify tumor organoids from brightfield images and generate a tumor organoid masks and another neural network to segment immune cells from brightfield images, from which the tumor organoid masks are used to quantify co-localization and kinetics of action in the tumor organoid.

As shown in FIG. 17, in an example, the system 1100 provides a patient-derived tumor organoid immune co-culture assay, that receives brightfield images 1102 collected over time and vital dye images 1104 collected over time. Both images types may be a series of time-lapse images for example. The brightfield images 1102 are provided to a deep learning framework 1106 trained as an imaging model, such as an artificial intelligence engine including one or more machine learning models or neural networks (e.g., models 1108 and 1110), trained to segment an input image into one or more targets and to generate different outputs (e.g., outputs 1112 and 1114) that may include a binary mask for the input image, a categorical mask (differentiating between organoids and one or more immune cell therapies), and/or a list of organoid locations, sizes, and/or degree of apoptosis. In the illustrated example, the deep learning framework 1106 includes an organoid classification & segmentation model 1108 which may have a configuration like that of model 322. Further, an immune cell classification & segmentation model 1110 is provided which may have a configuration like model 324. In some examples, the models 1108 and 1110 have a UNET configuration, such as using three-class or higher-class semantic segmentation fully convolution neural (FCN) network built upon a UNET architecture. In some examples, the models 1108 and 1110 are fully-connected FCNs. As with the models 322 and 324, while the models 1108 and 1110 are illustrated separately, they may represent a combined, single trained classification model, and therefore references herein to either model is to be construed as a reference to a single, combined model as well. As shown, the system 1100 provides a cascaded approach to tumor organoid analysis, using two FCN segmentation models and downstream quantification applied to detect both tumor organoids and immune cells for measuring tumor organoid-specific cell death and immune cell clustering and infiltration over time. The system 1100 provides label-free, tumor-organoid specific cell death tracking using brightfield image-based segmentation models and provides immune-tumor organoid cell-cell interaction tracking using two brightfield segmentation models that are combined to track the clustering and infiltration of immune cells around and into tumor organoids over time.

In an example implementation, co-culture, combining the organoids, PBMCs/immune cells and immunotherapy candidate, may be prepared such as by a process like that outlined in FIG. 9A. In some examples, the organoids may be prepared as described in Larsen et al., A pan-cancer organoid platform for precision medicine, Cell Reports, Vol. 36, Issue 4, 2021, such as the description of the development and culture of tumor organoids. For example, tumor organoids derived from patient tumor tissue may be stained with a reporter dye, for example, one that that measures apoptotic death via caspase 3/7 activation (the dye is low-dose and causes minimal phototoxicity over the course of the time series measurements). The tumor organoids are then co-cultured with immune cells, optionally in the presence of a drug candidate, and imaged via a confocal microscope as a series of time-lapse images to generate the brightfield images 1102 and the vital dye images 1104. The two neural networks models 1108 and 1110 have been trained, respectively, to segment the tumor-organoids and the immune cells directly from the brightfield images 1102. At an organoid tracking processing pipe 1116, the output tumor organoid 1112 mask output from the model 1108 is applied to the registered vital dye output 1104 to quantify the amount of tumor-organoid cell death. In other examples, both brightfield images 1102 and vital dye images 1104 are fed to the organoid processing pipe 116. The mean caspase 3/7 intensity within tumor organoids in a given well quantified the amount of TO cell death and was calculated by the processing pipe 1116 as:

$$TO \text{ cell death} = \frac{1}{O_w}\sum_{o=1}^{O_w}\frac{\sum_{i=1}^{A}I_{pixel}}{A} \qquad (1)$$

where $O_w$ is the number of tumor organoids in a well, A is the number of pixels in tumor organoid o, and $I_{pixel}$ is the caspase 3/7 fluorescence intensity in a pixel i. The processing pipe 1116 generates output images 1120 that represent tumor organoid tracking over time. The processing pipe 1116 may be configured to further calculate statistics across well-level technical triplicates. That is, in some examples, each co-culture condition may be replicated in at least 3 wells in a plate, that way any measurements from those wells can be analyzed statistically to account for biological variance/differences. For example, statistical outlier results may be removed, such as results greater or less than 1 or 2 standard deviations from other results. Mean or median results from the triplicate wells may be used, as an example. In the processing pipe, and in other examples herein, the method may calculate the per-organoid caspase intensity normalized by the area of the organoid, then average that value for each well. From there, the statistics between wells may then be analyzed statistically as described.

Simultaneously to operation of the processing pipe 1116, an immune cell tracking processing pipe 1118 receives the tumor organoid mask output 1112 from the model 1108 and the immune cell masks output 1114 from the model 1110 and quantifies the immune cells surrounding and in-filtrating the tumor organoids as a function of time. In an example, the processing pipe 1118 is configured to define, at each timepoint, a neighborhood around each of the tumor organoids by dilating the tumor organoid mask output 1112 using a kernel size of n pixels, e.g., 1000 pixels or fewer, 100 pixels or fewer, or 10 pixels or fewer. At the processing pipe 1118, the original tumor organoid mask output 1112 is subtracted from this dilated mask to obtain an annulus region that defines the co-localization neighborhood around each tumor organoid. By tracking the density of immune cells in this annulus region over time, the processing pipe 1118 can obtain a kinetic measurement of immune cell chemotaxis towards tumor organoids. Further, the processing pipe 1118 may calculate immune cell infiltration by quantifying the density of immune cells inside the area of the tumor organoid segmentation mask 1112 over time. Both of these measures are defined by the equations below:

$$\text{Density of clustered immune cells} = \frac{N_{cells\ inside\ annulus}}{Area_{annulus}} \qquad (2)$$

$$\text{Density of clustered immune cells} = \frac{N_{cells\ inside\ TO}}{Area_{TO}} \qquad (3)$$

The processing branch 1118 generates output images 1122 that represent immune cell tumor organoid interactions tracking over time.

The system 1100 is configured to generate reports of images visualizing the quantities defined by Equations (1)-(3) to summarize the amount of tumor organoid killing across time and correlate that to the degree of immune cell co-localization and infiltration providing a strong biological interpretability to the effectiveness of immunotherapies.

EXAMPLE

The system 1100 was used to perform a series of co-culture experiments, in particular measuring cell death by quantifying the caspase 3/7 vital dye pixel intensities at different time points using high-throughput imaging. All specimens for tumor organoids were collected from consented patients under protocols monitored by the Institutional Review Board at respective source institutions. We conducted PBMC experiments by co-culturing PBMCs with a breast cancer tumor organoid line in the presence of EPCAM-CD3 bispecific antibody (G&P Biosciences) for 96 hrs, and compared it with Muromonab-CD3 (CD3 monoclonal antibody (OKT3), Thermo Fisher Scientific). We conducted the CAR-T experiments using a gastric cancer tumor organoid line, co-cultured with a HER2-targeted CAR-T line for 72 hrs, compared against a non-targeted CAR-T line (ProMab Biotechnologies). We replicated the CAR-T experimental plate with all controls using CAR-T lines stained with CellTrace Far-Red (ThermoFisher) as a cell type-specific label. These 432 CAR-T fluorescent images were thresholded using a CellProfiler object detection pipeline to generate labels for training the immune cell segmentation model.

Figure 18:
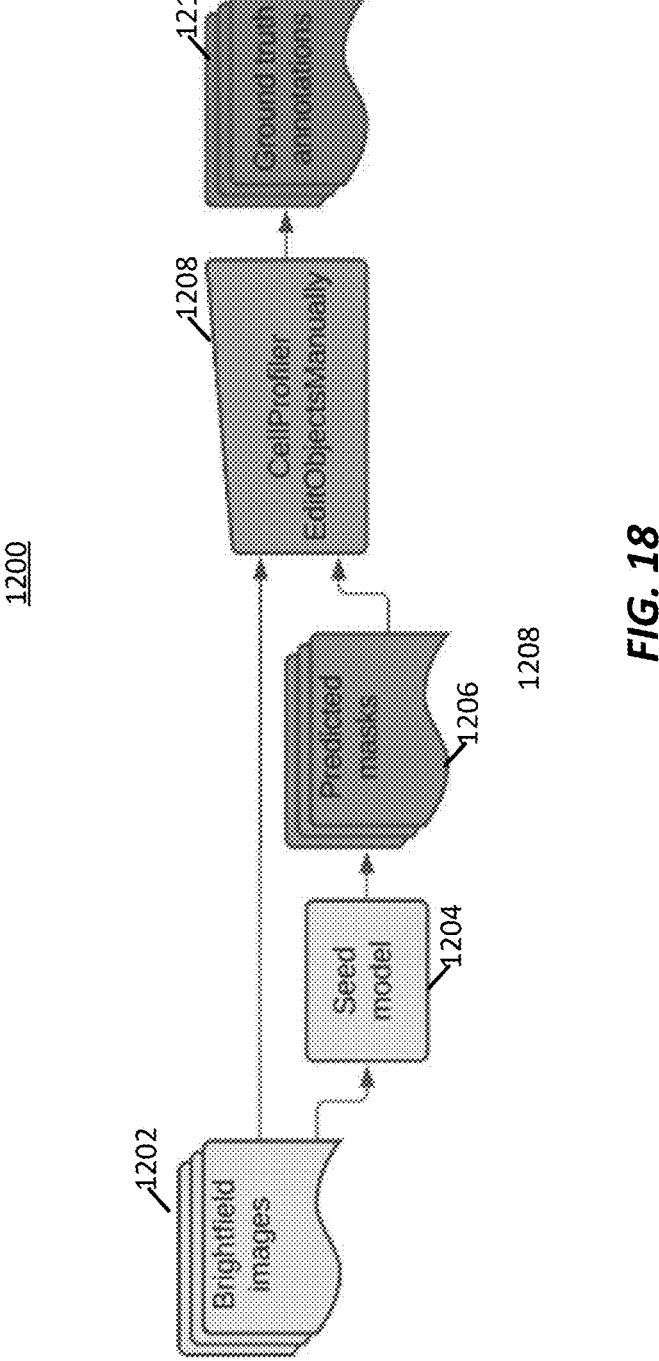
FIG. 18 is a schematic illustration of gathering ground truth labels for use in training a tumor organoid segmentation model using an annotation protocol, in accordance with an example.

We gathered ground truth labels for the tumor organoid segmentation model 1108 using the human annotations protocol shown in FIG. 18. The protocol is a model-in-the-loop annotation protocol 1200, in which brightfield images of organoids (1202) are provided to a seed segmentation model 1204 not trained on the organoid images. The seed segmentation model 1204 was used to infer segmentations on the brightfield images 1202 to reduce annotation time on training examples generating predicted masks 1206. At a process 1208, human annotators then corrected the predicted masks 1204 using a segmentation editing pipeline in Cell-Profiler based on EditsObjectsManually module, resulting in ground truth annotations 1210. Only in-focus tumor organoids were annotated in order to exclude any out-of-focus objects where associated cell death signal would not be measured due to better optical sectioning of the fluorescence image compared to the brightfield image. To exclude any nonviable tumor organoids at the start of the assay, we annotated only tumor organoids with >2 cells. We annotated a total of 407 images distributed across 4 cancer types (n=108 breast, n=72 gastric, n=167 head and neck, n=60 liver). The annotated set contained an even sampling of positive and negative controls in addition to the treated wells where possible. From each experimental plate, we chose 1 site out of 4 at random per well for the held-out test set and the rest were used for training. We held out an additional 10% of the training set as an internal validation set for model selection.

Both segmentation models 1108 and 1110 were implemented using a TensorFlow implementation of U-Net with 5 convolutional paired up-sampling and down-sampling layers, and 16 features in the first layer. We performed class weight parameter sweeps for both models 1108 and 1110 ranging from 1:1 to 10:1 in foreground: background weight ratio. We observed a ~2% change in model performance within 2 integer values of the optimal class weight. The tumor organoid segmentation model 1108 was trained with a class weight of 2, while the immune cell segmentation model 1110 implemented as CAR-T model was trained with a class weight of 6. We trained both models 1108 and 1110 using ~15 GB on a NVIDIA Tesla T4 GPU for 200 epochs over ~14 hrs, using the Adam optimizer and a learning rate of 0.001.

We benchmarked the tumor organoid segmentation model 1108 against an adaptive threshold-based approach based on brightfield intensity using a custom analysis module in MetaXpress software. We calculated the following evaluation metrics: image-mean Dice scores, calculated as the mean of Dice per image in the test set, as well as batch Dice, calculated as the Dice score of the concatenated images in the test set.

Figures 19A, 19B, 19C:
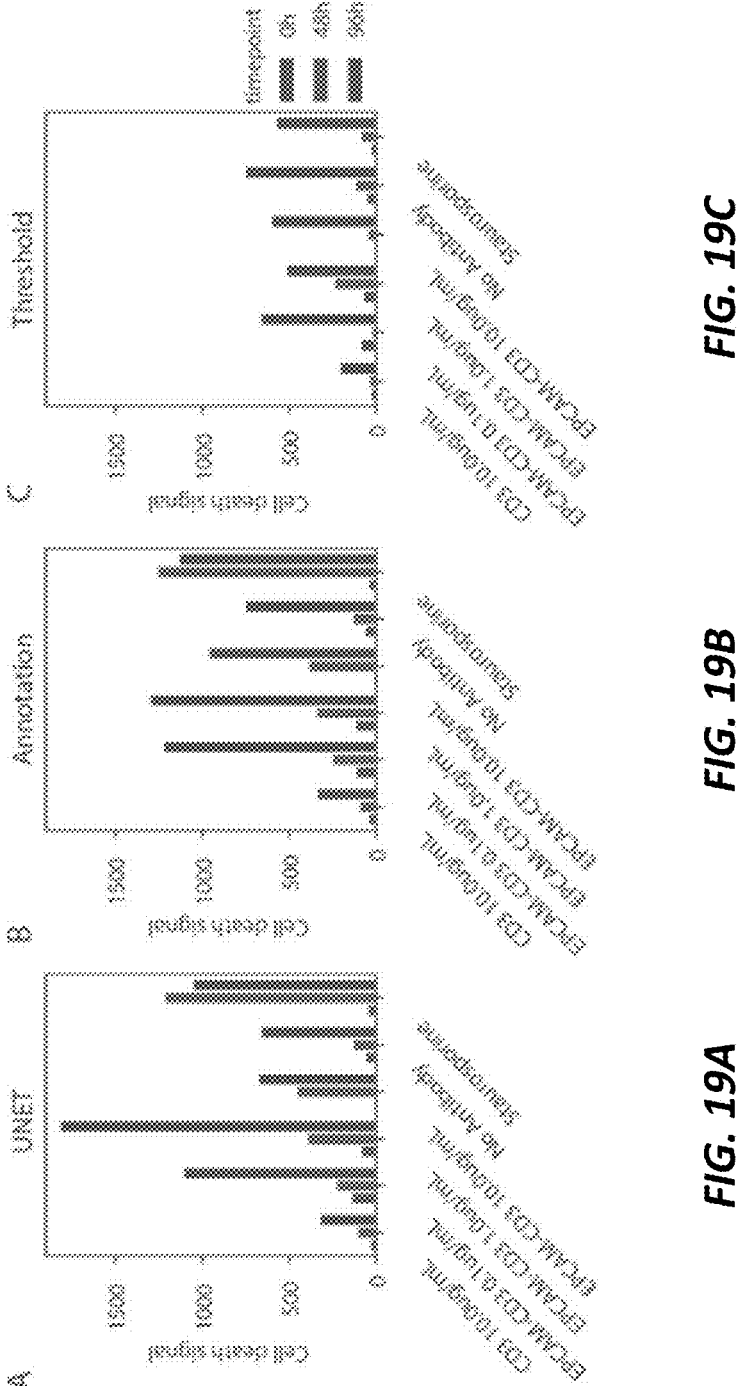
FIGS. 19A-19C are plots analyzing tumor organoid cell death determined from segmentations generated by a machine learning algorithm of the present techniques (FIG. 19A), ground truth organoid annotations (FIG. 19B), and threshold-based segmentation on brightfield images using MetaXpress (FIG. 19C), in accordance with an example.

The results of this example were as follows. We configured application-specific metrics for each segmentation model. The tumor organoid segmentation model 1108 was primarily used for object area detection, and the system 1100 calculated Dice scores across a held-out test set of 141 images. We compared the model 1108 performance against a threshold-based brightfield segmentation approach provided by MetaXpress (Molecular Devices). We found that tumor organoid segmentation significantly outperformed the brightfield threshold-based approach (batch Dice of 0.86 vs. 0.32; image-mean Dice score of 0.80±0.1 vs. 0.27±0.29, P<1e-6). Although Dice scores are a useful direct measure of model performance, the end use of the organoid segmentation mask was to obtain an accurate readout of cell death. We confirmed that the cell death signal over time using the predicted tumor organoid masks matched the cell death signal calculated from ground truth annotations much more closely than when using threshold masks. FIGS. 19A-19C illustrate tumor organoid cell death, determined from segmentations generated by the UNET model inference (FIG. 19A), ground truth organoid annotations (FIG. 19B), and threshold-based segmentation on brightfield images using MetaXpress (FIG. 19C).

Figures 20A, 20B, 20C:
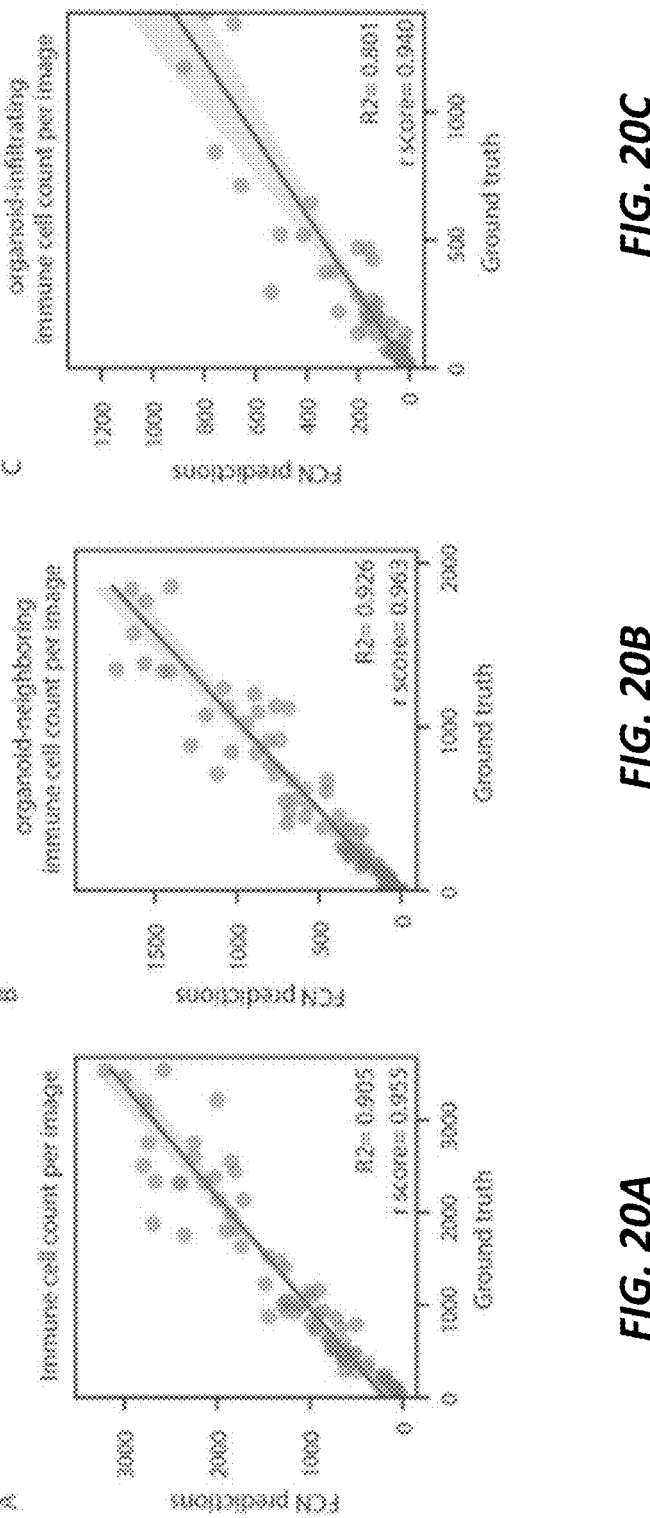
FIGS. 20A-20C are regression plots comparing ground truth immune cell counts from threshold cell statins on CAR-T cells to model predictions for all CAR-T cells in an image (FIG. 20A), CAR-T cells clustered around organoids (FIG. 20B), and CAR-Ts infiltrated into organoids (FIG. 20C), in accordance with an example.

The immune cell segmentation model 1110 was used to quantify immune cell counts both in and around the tumor organoids. Hence, the model 1110 was evaluated using regression based metrics of correlation coefficient (r) and coefficient of determination (R2) between the inferred count and the ground truth count obtained via fluorescent labeling. In an example, we compared the model predictions against a threshold-based fluorescence segmentation approach in CellProfiler. Overall, there were high correlations between inferred and ground truth count for all immune cell subset, as shown in Table 1 and in the examples in FIGS. 20A-20C, which show regression plots comparing ground truth immune cell counts from threshold cell statins on CAR-T cells to model predictions for all CAR-T cells in an image (FIG. 20A), CAR-T cells clustered around organoids (FIG. 20B), and CAR-Ts infiltrated into organoids (FIG. 20C).

TABLE 1

Performance metrics for the immune segmentation model, with reference to thresholded fluorescence-labeled images as ground truth.

| Immune cell counts | r | $R^2$ |
|---|---|---|
| All immune cells | 0.96 | 0.91 |
| Clustered immune cells | 0.96 | 0.92 |
| Infiltrated immune cells | 0.94 | 0.82 |

Figures 21A, 21B:
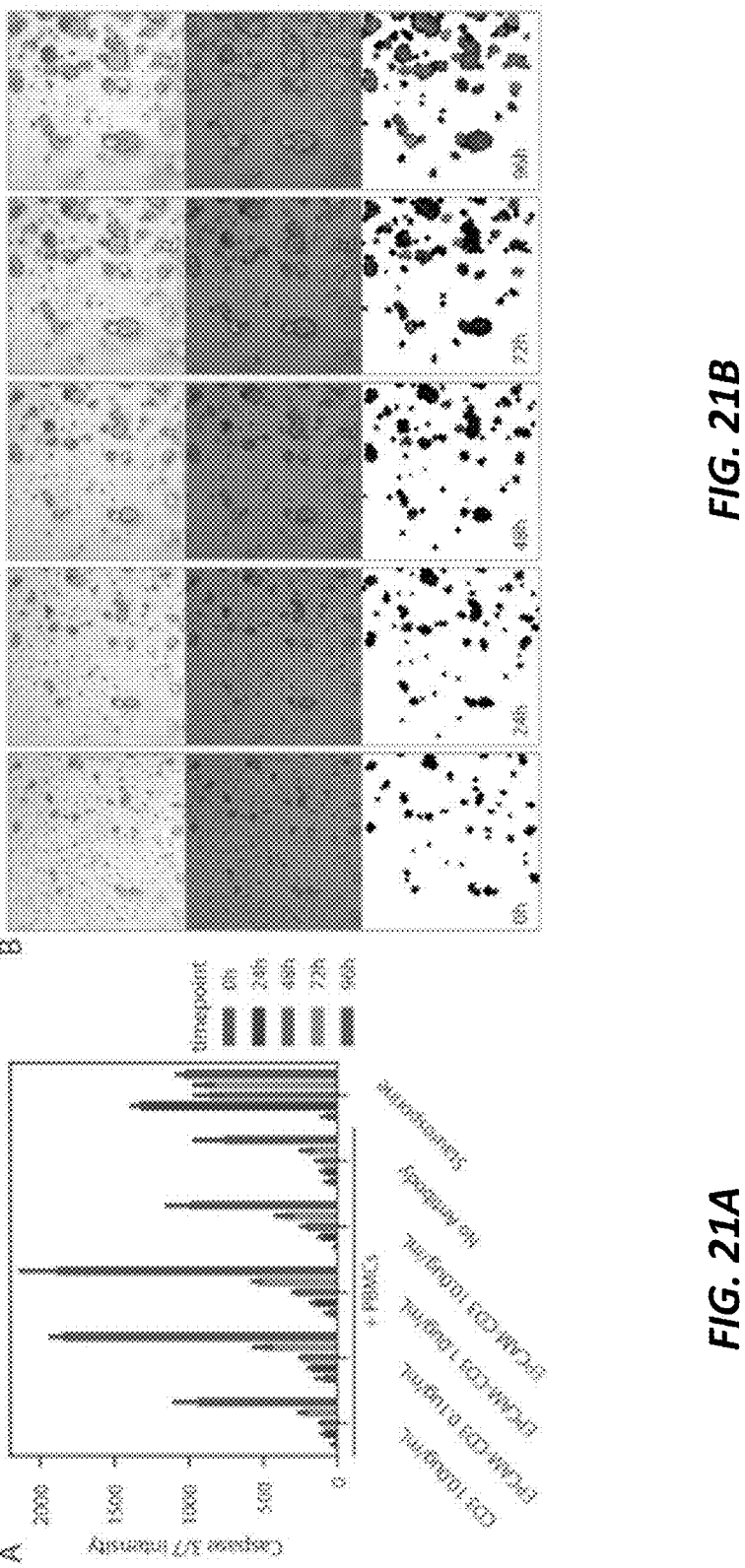
FIG. 21A is a plot of organoid cell death in comparison to positive controls, in accordance with an example.
FIG. 21B are images as analyzed and generated by an image-based co-culture analysis system analyzing organoid cell death, in accordance with an example.
Figures 22A, 22B:
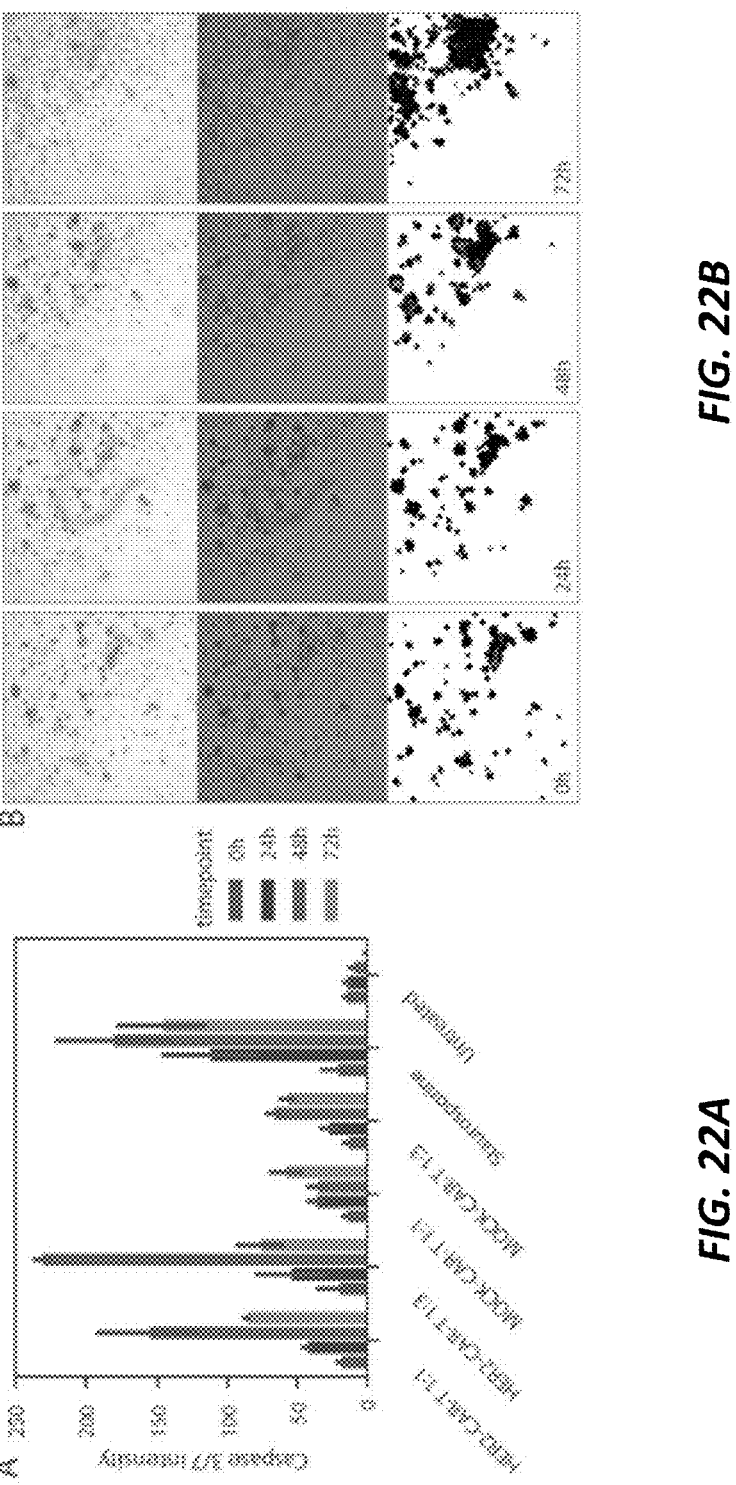
FIG. 22A is a plot of organoid cell death for targeted CAR-T cells, in accordance with an example.
FIG. 22B are images as analyzed and generated by an image-based co-culture analysis system showing CAR-T cells approaching, clustering, then invading and dissolving the intact tumor organoids into disparate dead cells over time, in accordance with an example.
Figures 23A, 23B, 23C, 23D:
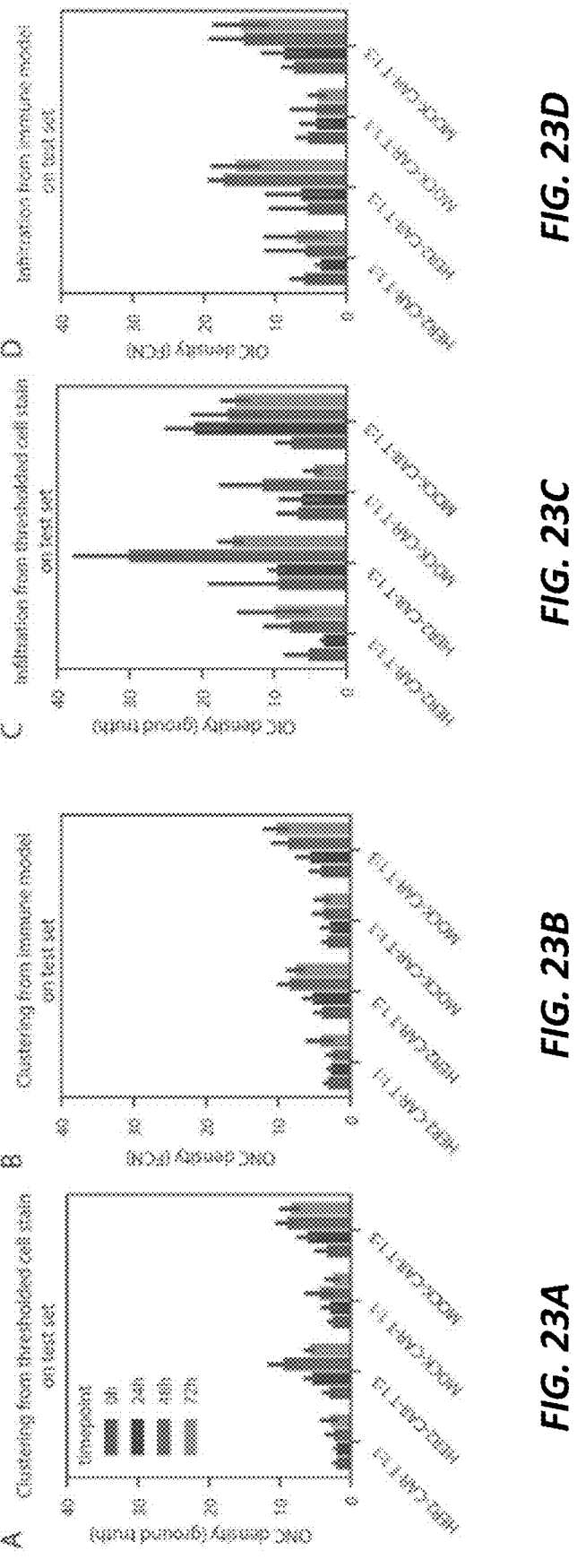
FIGS. 23A-23D are time series plots of different clustering and infiltration of immune cells as analyzed by an image-based co-culture analysis system, in accordance with an example.
Figures 24A, 24B, 24C, 24D:
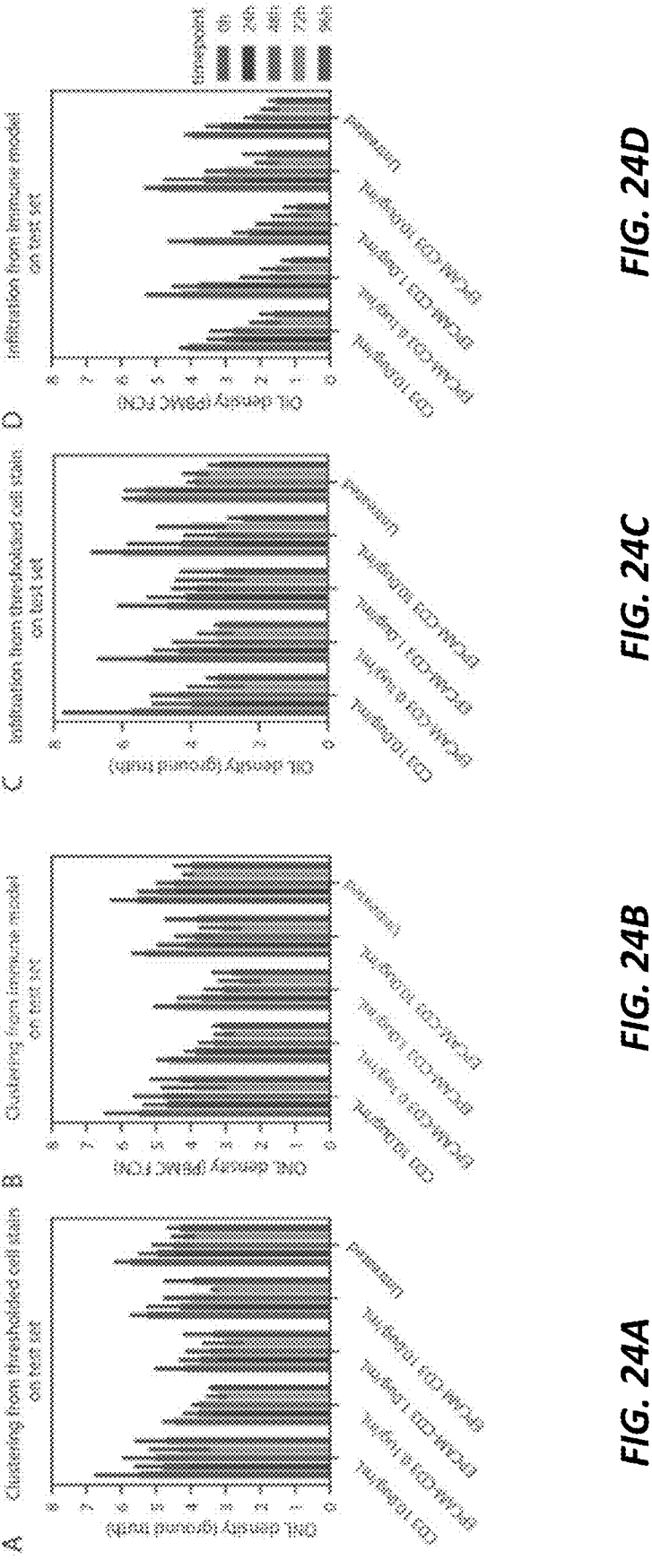
FIGS. 24A-24D are each time series plots illustrating clustering and infiltration of PBMCs over time compared between ground truth threshold cell stains and a segmentation model, in accordance with an example.
Figures 25A, 25B:
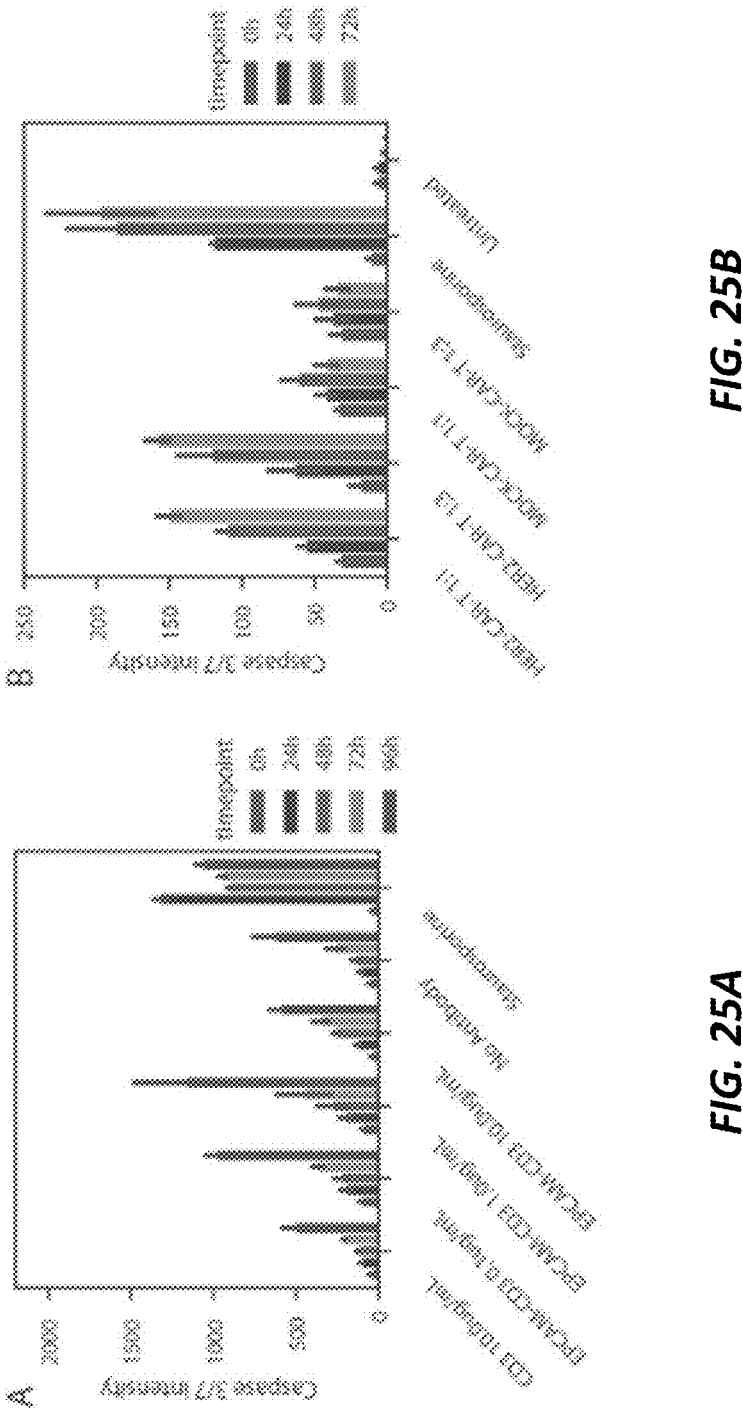
FIG. 25A are time series plots showing significant reduction of PBMC tumor killing activity where a cell counterstain, CellTrace Far-Red, is within the co-culture, in accordance with an example.
FIG. 25B are a series of time plots showing co-cultures with CAR-T cells and corresponding cell death measurements, in accordance with an example.

We applied the tumor organoid segmentation model output 1112 to calculate tumor organoid-specific cell death over time (FIG. 21B) in response to co-culture with PBMCs and an EPCAM-CD3 bispecific antibody, designed to bind to EpCAM proteins on tumor cells and CD3 receptors on immune cells. We observed that EPCAM-CD3 at 0.1 ug/mL and 1.0 ug/mL results in a higher cell death signal at each timepoint in comparison to both positive controls: staurosporine and muromonab-CD3 (OKT3), a clinically tested monoclonal antibody (FIG. 21A). However, at high dose (10 ug/mL), cell death signal was comparable with OKT3 and staurosporine, possibly due to the Hook effect. Notably, targeted CAR-T cells resulted in an equivalent level of cell death as the staurosporine positive control, in comparison to untargeted CAR-T cells, which performed only slightly better than the negative control (FIG. 22A). Upon examination of well-level output images over time, we observed the CAR-T cells approaching, clustering, then invading and dissolving the intact TOs into disparate dead cells over time (FIG. 22B). This visual representation was quantified in the time series plots shown in FIGS. 23A-24D. We quantified immune cell infiltration and clustering by combining the immune cell segmentation model output with the tumor organoid segmentation model output. We focused on the CAR-T experiments for this example because while the PBMC co-cultures utilize a mix of immune cells from a donor, where a subset are active T-cells, the CAR-T co-cultures utilize pure T-cell immune populations engineered to target tumor cells, making them more amenable to population-level tracking. FIGS. 24A-25D illustrate clustering and infiltration of PBMCs over time compared between ground truth threshold cell stains and a segmentation model as described herein. Furthermore, CAR-T cell exclusion due to the immunosuppressive microenvironment found within solid tumors has been reported as a mechanism of resistance. Brightfield identification of PBMCs was further complicated by the difficulty of achieving accurate labeling. Notably, we observed significant reduction of PBMC tumor killing activity in an experiment where a cell counterstain, CellTrace Far-Red, is applied (see, FIG. 25A).

Figures 26A, 26B, 26C, 26D:
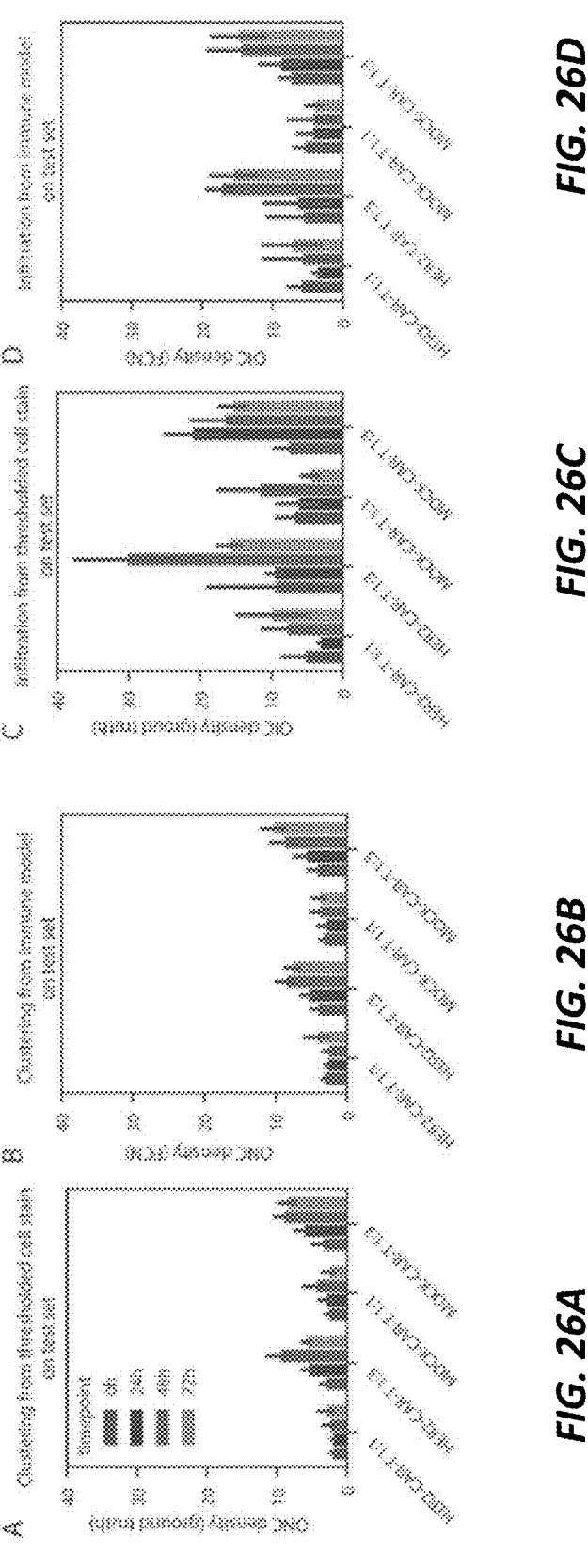
FIG. 26A-26D are each time series plots illustrating clustering and infiltration for CAR-T cells as analyzed by an image-based co-culture analysis system, in accordance with an example.
Figures 27A, 27B, 27C:
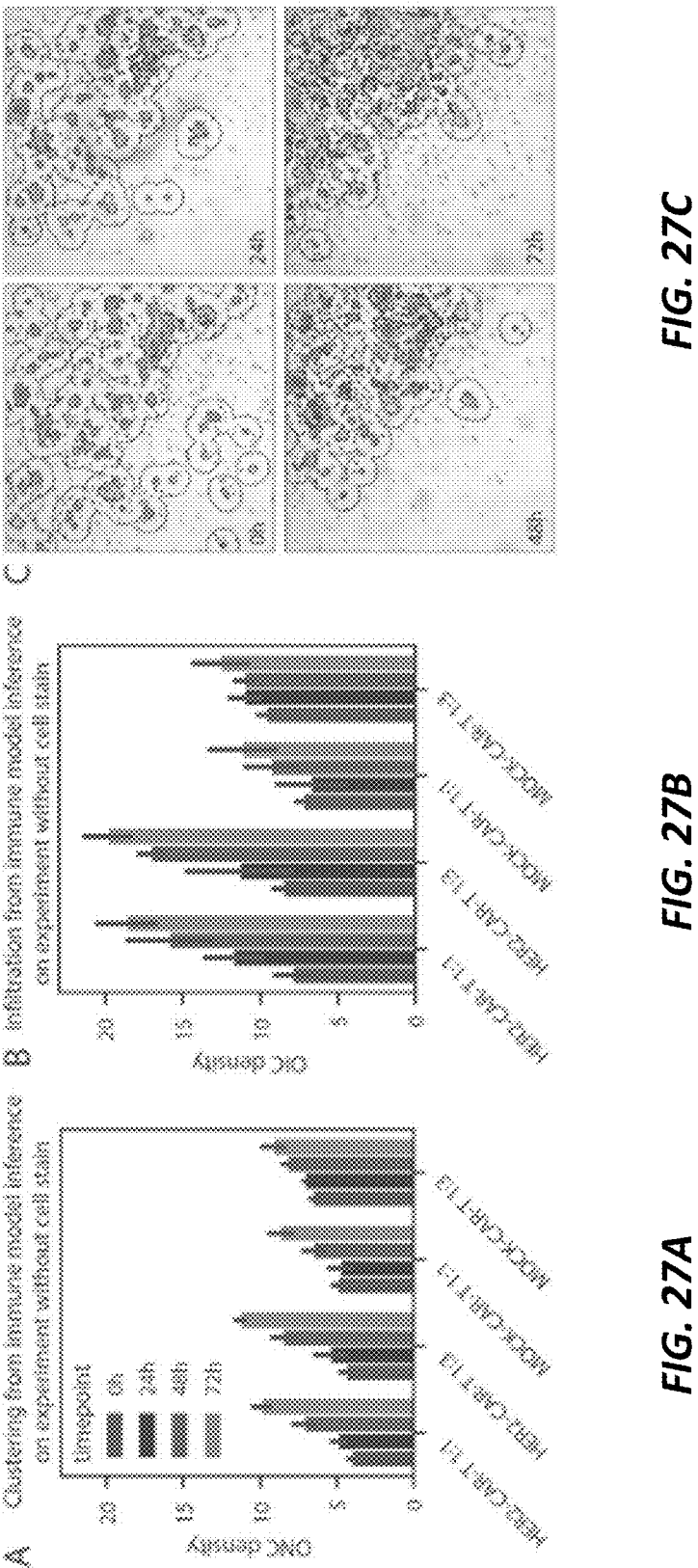
FIGS. 27A and 27B are each time series plots showing clustering and infiltration, respectively, of CAR-T cells, in accordance with another example.
FIG. 27C are images generated by an image-based co-culture analysis system showing clustering and infiltration and cell death, in accordance with an example.

We compared CAR-T clustering density between model predictions and ground truth in the labeled test set (see, FIGS. 26A & 27B). Overall trends in density were replicated in model predictions-surprisingly, clustering activity is similar between targeted and untargeted CAR-T cells. However, when we looked at infiltrated CAR-T cells for the labeled test set (see, FIGS. 26C & 27D), we then see a differentiation of response between targeted and untargeted lines. Therefore, although both types of CAR-T cells are drawn toward tumor organoids, the targeted line more effectively infiltrated and killed the tumors, as shown in the corresponding cell death measurements (see, FIG. 25B). In an unlabeled CAR-T experiment, we found that CAR-T clustering and infiltration (see, FIG. 27A-28C) generally tracked trends in cell death signal (see, FIG. 22A) for both targeted and untargeted cells at all ratios. In particular, we found that clustering and infiltration intensities increase over time at the 1:1 and 1:3 ratios, tracking increasing cell death signals up to 48 h. At 72 h, the tumor organoids were largely dead, resulting in less caspase 3/7 activation while the CAR-T cells continue to cluster around the remaining tumor organoid debris. Although we only observed a modest difference between targeted vs untargeted clustering, we observed a larger enhancement in the infiltration signal when comparing targeted to untargeted CAR-T cells. This mechanism likely explains the higher level of TO cell death in response to HER2-targeted CAR-Ts in the cell death measurements.

The experiment showed that through a cascaded approach using two different segmentation models and down-stream quantification, a highly effective solution that segments tumor organoids and immune cells from brightfield images may be used to examine and better understand their dynamics through analysis of time-lapse imaging. The two model approach allows for examination into the pharmacokinetics and mechanisms of CAR-T cells as well as PBMCs catalyzed by bi-specific antibody therapies. For example, we show quantification plots demonstrating a strong correlation between tumor organoid death and the degree of colocalization/infiltration by the immune cells across time, thus allowing for model interpretability and a much more informed drug discovery process.

In an example, the Infiltration metrics and clustering metrics were derived using post-processing methods where the inputs to these methods were the paired segmentation masks produced by the organoid segmentation model and the immune segmentation model, described above. For post-processing for clustering: At each timepoint, we defined a neighborhood around each of the TOs by dilating the TO segmentation mask using a kernel size of 100 pixels. The original TO mask was subtracted from this dilated mask to obtain an annulus region that defined the colocalization neighborhood around each TO. By tracking the density of immune cells in this annulus region, we measured the immune clustering around TOs. For the post-processing for infiltration: we further computed immune cell infiltration by quantifying the density of immune cells inside the area of the TO segmentation mask over time.

The methods and systems described above may be utilized in combination with or as part of a digital and laboratory health care platform that is generally targeted to medical care and research. It should be understood that many uses of the methods and systems described above, in combination with such a platform, are possible. One example of such a platform is described in U.S. Patent Publication No. 2021/0090694, titled "Data Based Cancer Research and Treatment Systems and Methods", and published Mar. 25, 2021, which is incorporated herein by reference and in its entirety for any and all purposes. For example, an implementation of one or more embodiments of the methods and systems as described above may include microservices constituting a digital and laboratory health care platform supporting imaging and analysis of organoid and immune cell co-cultures to measure organoid susceptibility to immune cells and/or immune-oncology therapies. Embodiments may include a single microservice for executing and delivering co-culture imaging analysis or may include a plurality of microservices each having a particular role which together implement one or more of the embodiments above. In one example, a first microservice may execute image capture in order to deliver images to a second microservice for measuring the interaction of organoids and immune cells and/or immune-oncology therapies. Similarly, the second microservice or a third microservice may execute instructions to generate the co-culture images using information generated by one or more of the first or second microservices and then to analyze the co-culture images according to an embodiment, above.

Where embodiments above are executed in one or more micro-services with or as part of a digital and laboratory health care platform, one or more of such micro-services may be part of an order management system that orchestrates the sequence of events as needed at the appropriate time and in the appropriate order necessary to instantiate embodiments above. A micro-services based order management system is disclosed, for example, in U.S. Patent Publication No. 2020/80365232, titled "Adaptive Order Fulfillment and Tracking Methods and Systems", and published Nov. 19, 2020, which is incorporated herein by reference and in its entirety for all purposes. For example, continuing with the above first and second microservices, an order management system may notify the first microservice that an order for a current therapy or treatment notification and clinically relevant event identification has been received and is ready for processing. The first microservice may execute and notify the order management system once the co-culture images are ready for the second microservice. Furthermore, the order management system may identify that execution parameters (prerequisites) for the second microservice are satisfied, including that the first microservice has completed, and notify the second microservice that it may continue analyzing the co-culture images according to an embodiment, above.

Where the digital and laboratory health care platform further includes a genetic analyzer system, the genetic analyzer system may include targeted panels and/or sequencing probes. An example of a targeted panel for sequencing cell-free (cf) DNA and determining various characteristics of a specimen based on the sequencing is disclosed, for example, in U.S. patent application Ser. No. 17/179,086, titled "Methods And Systems For Dynamic Variant Thresholding In A Liquid Biopsy Assay", and filed Feb. 18, 2021, U.S. patent application Ser. No. 17/179,267, titled "Estimation Of Circulating Tumor Fraction Using Off-Target Reads Of Targeted-Panel Sequencing", and filed Feb. 18, 2021, and U.S. patent application Ser. No. 17/179,279, titled "Methods And Systems For Refining Copy Number Variation In A Liquid Biopsy Assay", and filed Feb. 18, 2021 which are incorporated herein by reference and in their entirety for all purposes. In one example, targeted panels may enable the delivery of next generation sequencing results for organoid and/or immune cell characterization and/or therapy response data delivery according to an embodiment, above. An example of the design of next-generation sequencing probes is disclosed, for example, in U.S. Patent Publication No. 2021/0115511, titled "Systems and Methods for Next Generation Sequencing Uniform Probe Design", and published Jun. 22, 2021, and U.S. patent application Ser. No. 17/323,986, titled "Systems and Methods for Next Generation Sequencing Uniform Probe Design", and filed May 18, 2021, which are incorporated herein by reference and in their entirety for all purposes.

Where the digital and laboratory health care platform further includes an epigenetic analyzer system, the epigenetic analyzer system may analyze specimens to determine their epigenetic characteristics and may further use that information for monitoring a patient over time. An example of an epigenetic analyzer system is disclosed, for example, in U.S. patent application Ser. No. 17/352,231, titled "Molecular Response And Progression Detection From Circulating Cell Free DNA", and filed Jun. 18, 2021, which is incorporated herein by reference and in its entirety for all purposes.

Where the digital and laboratory health care platform further includes a bioinformatics pipeline, the methods and systems described above may be utilized after completion or substantial completion of the systems and methods utilized in the bioinformatics pipeline. As one example, the bioinformatics pipeline may receive next-generation genetic sequencing results and return a set of binary files, such as one or more BAM files, reflecting DNA and/or RNA read counts aligned to a reference genome. The methods and systems described above may be utilized, for example, to ingest the DNA and/or RNA read counts and produce organoid and/or immune cell characterization and/or therapy response data as a result.

When the digital and laboratory health care platform further includes an RNA data normalizer, any RNA read counts may be normalized before processing embodiments as described above. An example of an RNA data normalizer is disclosed, for example, in U.S. Patent Publication No. 2020/0098448, titled "Methods of Normalizing and Correcting RNA Expression Data", and published Mar. 26, 2020, which is incorporated herein by reference and in its entirety for all purposes.

When the digital and laboratory health care platform further includes a genetic data deconvolver, any system and method for deconvolving may be utilized for analyzing genetic data associated with a specimen having two or more biological components to determine the contribution of each component to the genetic data and/or determine what genetic data would be associated with any component of the specimen if it were purified. An example of a genetic data deconvolver is disclosed, for example, in U.S. Patent Publication No. 2020/0210852, published Jul. 2, 2020, and PCT/US19/69161, filed Dec. 31, 2019, and both titled "Transcriptome Deconvolution of Metastatic Tissue Samples"; and U.S. patent application Ser. No. 17/074,984, titled "Calculating Cell-type RNA Profiles for Diagnosis and Treatment", and filed Oct. 20, 2020, the contents of each of which are incorporated herein by reference and in their entirety for all purposes. RNA expression levels may be adjusted to be expressed as a value relative to a reference expression level. Furthermore, multiple RNA expression data sets may be adjusted, prepared, and/or combined for analysis and may be adjusted to avoid artifacts caused when the data sets have differences because they have not been generated by using the same methods, equipment, and/or reagents.

When the digital and laboratory health care platform further includes an automated RNA expression caller, RNA expression levels associated with multiple samples may be compared to determine whether an artifact is causing anomalies in the data. An example of an automated RNA expression caller is disclosed, for example, in U.S. Pat. No. 11,043,283, titled "Systems and Methods for Automating RNA Expression Calls in a Cancer Prediction Pipeline", and issued Jun. 22, 2021, which is incorporated herein by reference and in its entirety for all purposes.

The digital and laboratory health care platform may further include one or more insight engines to deliver information, characteristics, or determinations related to a disease state that may be based on genetic and/or clinical data associated with a patient and/or specimen. Exemplary insight engines may include a tumor of unknown origin engine, a human leukocyte antigen (HLA) loss of homozygosity (LOH) engine, a tumor mutational burden engine, a PD-L1 status engine, a homologous recombination deficiency engine, a cellular pathway activation report engine, an immune infiltration engine, a microsatellite instability engine, a pathogen infection status engine, a T cell receptor or B cell receptor profiling engine, a line of therapy engine, and so forth.

An example tumor of unknown origin engine is disclosed, for example, in U.S. Patent Publication No. 2020/0365268, titled "Systems and Methods for Multi-Label Cancer Classification", and published Nov. 19, 2020, which is incorporated herein by reference and in its entirety for all purposes.

An example of an HLA LOH engine is disclosed, for example, in U.S. Pat. No. 11,081,210, titled "Detection of Human Leukocyte Antigen Loss of Heterozygosity", and issued Aug. 3, 2021, which is incorporated herein by reference and in its entirety for all purposes.

An example of a tumor mutational burden (TMB) engine is disclosed, for example, in U.S. Patent Publication No. 2020/0258601, titled "Targeted-Panel Tumor Mutational Burden Calculation Systems and Methods", and published Aug. 13, 2020, which is incorporated herein by reference and in its entirety for all purposes.

An example of a PD-L1 status engine is disclosed, for example, in U.S. Patent Publication No. 2020/0395097, titled "A Pan-Cancer Model to Predict The PD-L1 Status of a Cancer Cell Sample Using RNA Expression Data and Other Patient Data", and published Dec. 17, 2020, which is incorporated herein by reference and in its entirety for all purposes. An additional example of a PD-L1 status engine is disclosed, for example, in U.S. Pat. No. 10,957,041, titled "Determining Biomarkers from Histopathology Slide Images", and issued Mar. 23, 2021, which is incorporated herein by reference and in its entirety for all purposes.

An example of a homologous recombination deficiency engine is disclosed, for example, in U.S. Pat. No. 10,975,445, issued Apr. 13, 2021 and PCT/US20/18002, filed Feb. 12, 2020, and both titled "An Integrative Machine-Learning Framework to Predict Homologous Recombination Deficiency", which are incorporated herein by reference and in their entirety for all purposes.

An example of a cellular pathway activation report engine is disclosed, for example, in U.S. Patent Publication No. 2021/0057042, titled "Systems And Methods For Detecting Cellular Pathway Dysregulation In Cancer Specimens", and published Feb. 25, 2021, which is incorporated herein by reference and in its entirety for all purposes.

An example of an immune infiltration engine is disclosed, for example, in U.S. Patent Publication No. 2020/0075169, titled "A Multi-Modal Approach to Predicting Immune Infiltration Based on Integrated RNA Expression and Imaging Features", and published Mar. 5, 2020, which is incorporated herein by reference and in its entirety for all purposes.

An example of an MSI engine is disclosed, for example, in U.S. Patent Publication No. 2020/0118644, titled "Microsatellite Instability Determination System and Related Methods", and published Apr. 16, 2020, which is incorporated herein by reference and in its entirety for all purposes. An additional example of an MSI engine is disclosed, for example, in U.S. Patent Publication No. 2021/0098078, titled "Systems and Methods for Detecting Microsatellite Instability of a Cancer Using a Liquid Biopsy", and published Apr. 1, 2021, which is incorporated herein by reference and in its entirety for all purposes.

An example of a pathogen infection status engine is disclosed, for example, in U.S. Pat. No. 11,043,304, titled "Systems And Methods For Using Sequencing Data For Pathogen Detection", and issued Jun. 22, 2021, which is incorporated herein by reference and in its entirety for all purposes. Another example of a pathogen infection status engine is disclosed, for example, in PCT/US21/18619, titled "Systems And Methods For Detecting Viral DNA From Sequencing", and filed Feb. 18, 2021, which is incorporated herein by reference and in its entirety for all purposes.

An example of a T cell receptor or B cell receptor profiling engine is disclosed, for example, in U.S. patent application Ser. No. 17/302,030, titled "TCR/BCR Profiling", and filed Apr. 21, 2021, which is incorporated herein by reference and in its entirety for all purposes.

An example of a line of therapy engine is disclosed, for example, in U.S. Patent Publication No. 2021/0057071, titled "Unsupervised Learning And Prediction Of Lines Of Therapy From High-Dimensional Longitudinal Medications Data", and published Feb. 25, 2021, which is incorporated herein by reference and in its entirety for all purposes.

When the digital and laboratory health care platform further includes a report generation engine, the methods and systems described above may be utilized to create a summary report of a patient's genetic profile and the results of one or more insight engines for presentation to a physician. For instance, the report may provide to the physician information about the extent to which the specimen that was sequenced contained tumor or normal tissue from a first organ, a second organ, a third organ, and so forth. For example, the report may provide a genetic profile for each of the tissue types, tumors, or organs in the specimen. The genetic profile may represent genetic sequences present in the tissue type, tumor, or organ and may include variants, expression levels, information about gene products, or other information that could be derived from genetic analysis of a tissue, tumor, or organ.

The report may include therapies and/or clinical trials matched based on a portion or all of the genetic profile or insight engine findings and summaries. For example, the clinical trials may be matched according to the systems and methods disclosed in U.S. Patent Publication No. 2020/0381087, titled "Systems and Methods of Clinical Trial Evaluation", and published Dec. 3, 2020, which is incorporated herein by reference and in its entirety for all purposes.

The report may include a comparison of the results (for example, molecular and/or clinical patient data) to a database of results from many specimens. An example of methods and systems for comparing results to a database of results are disclosed in U.S. Patent Publication No. 2020/0135303 titled "User Interface, System, And Method For Cohort Analysis" and published Apr. 30, 2020, and U.S. Patent Publication No. 2020/0211716 titled "Method and Process for Predicting and Analyzing Patient Cohort Response, Progression and Survival", and published Jul. 2, 2020, which is incorporated herein by reference and in its entirety for all purposes. The information may be used, sometimes in conjunction with similar information from additional specimens and/or clinical response information, to match therapies likely to be successful in treating a patient, discover biomarkers or design a clinical trial.

Any data generated by the systems and methods and/or the digital and laboratory health care platform may be downloaded by the user. In one example, the data may be downloaded as a CSV file comprising clinical and/or molecular data associated with tests, data structuring, and/or other services ordered by the user. In various embodiments, this may be accomplished by aggregating clinical data in a system backend, and making it available via a portal. This data may include not only variants and RNA expression data, but also data associated with immunotherapy markers such as MSI and TMB, as well as RNA fusions.

When the digital and laboratory health care platform further includes a device comprising a microphone and speaker for receiving audible queries or instructions from a user and delivering answers or other information, the methods and systems described above may be utilized to add data to a database the device can access. An example of such a device is disclosed, for example, in U.S. Patent Publication No. 2020/0335102, titled "Collaborative Artificial Intelligence Method And System", and published Oct. 22, 2020, which is incorporated herein by reference and in its entirety for all purposes.

When the digital and laboratory health care platform further includes a mobile application for ingesting patient records, including genomic sequencing records and/or results even if they were not generated by the same digital and laboratory health care platform, the methods and systems described above may be utilized to receive ingested patient records. An example of such a mobile application is disclosed, for example, in U.S. Pat. No. 10,395,772, titled "Mobile Supplementation, Extraction, And Analysis Of Health Records", and issued Aug. 27, 2019, which is incorporated herein by reference and in its entirety for all purposes. Another example of such a mobile application is disclosed, for example, in U.S. Pat. No. 10,902,952, titled "Mobile Supplementation, Extraction, And Analysis Of Health Records", and issued Jan. 26, 2021, which is incorporated herein by reference and in its entirety for all purposes. Another example of such a mobile application is disclosed, for example, in U.S. Patent Publication No. 2021/0151192, titled "Mobile Supplementation, Extraction, And Analysis Of Health Records", and filed May 20, 2021, which is incorporated herein by reference and in its entirety for all purposes.

When the digital and laboratory health care platform further includes organoids developed in connection with the platform (for example, from the patient specimen), the methods and systems may be used to further evaluate genetic sequencing data derived from an organoid and/or the organoid sensitivity, especially to therapies matched based on a portion or all of the information determined by the systems and methods, including predicted cancer type(s), likely tumor origin(s), etc. These therapies may be tested on the organoid, derivatives of that organoid, and/or similar organoids to determine an organoid's sensitivity to those therapies. Any of the results may be included in a report. If the organoid is associated with a patient specimen, any of the results may be included in a report associated with that patient and/or delivered to the patient or patient's physician or clinician. In various examples, organoids may be cultured and tested according to the systems and methods disclosed in U.S. Patent Publication No. 2021/0155989, titled "Tumor Organoid Culture Compositions, Systems, and Methods", published May 27, 2021; PCT/US20/56930, titled "Systems and Methods for Predicting Therapeutic Sensitivity", filed Oct. 22, 2020; U.S. Patent Publication No. 2021/0172931, titled "Large Scale Organoid Analysis", published Jun. 10, 2021; PCT/US2020/063619, titled "Systems and Methods for High Throughput Drug Screening", filed Dec. 7, 2020 and U.S. patent application Ser. No. 17/301,975, titled "Artificial Fluorescent Image Systems and Methods", filed Apr. 20, 2021 which are each incorporated herein by reference and in their entirety for all purposes. In one example, the drug sensitivity assays may be especially informative if the systems and methods return results that match with a variety of therapies, or multiple results (for example, multiple equally or similarly likely cancer types or tumor origins), each matching with at least one therapy.

When the digital and laboratory health care platform further includes application of one or more of the above in combination with or as part of a medical device or a laboratory developed test that is generally targeted to medical care and research, such laboratory developed test or medical device results may be enhanced and personalized through the use of artificial intelligence. An example of laboratory developed tests, especially those that may be enhanced by artificial intelligence, is disclosed, for example, in U.S. Patent Publication No. 2021/0118559, titled "Artificial Intelligence Assisted Precision Medicine Enhancements to Standardized Laboratory Diagnostic Testing", and published Apr. 22, 2021, which is incorporated herein by reference and in its entirety for all purposes.

It should be understood that the examples given above are illustrative and do not limit the uses of the systems and methods described herein in combination with a digital and laboratory health care platform.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components or multiple components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a microcontroller, field programmable gate array (FPGA) or an application-specific integrated circuit (ASIC)) to perform certain operations. A hardware module may also comprise programmable logic or circuitry (e.g., as encompassed within a processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a processor configured using software, the processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connects the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of the example methods described herein can be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method can be performed by one or more processors or processor-implemented hardware modules. The performance of certain of the operations may be distributed among the one or more processors, not only residing within a single machine, but also deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but also deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, nonvolatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

This detailed description is to be construed as an example only and does not describe every possible embodiment, as describing every possible embodiment would be impractical, if not impossible. One could implement numerous alternative embodiments, using either current technology or technology developed after the filing date of this application.

The invention claimed is:

1. A method for characterizing cancer organoid response to an immune cell based therapy, the method comprising:

providing a first combination to a first culturing well,
wherein the first combination comprises a mixture of one or more cancer organoid cells with one or more immune cells;

culturing the first combination under conditions which support growth of the one or more cancer organoid cells, wherein culturing the first combination creates cultured cancer organoid cells and cultured immune cells;

capturing, at different time points, a plurality of brightfield images of the first culturing well comprising the first combination;

capturing, at different time points and corresponding to the plurality of brightfield images, a plurality of fluorescent images of the first culturing well comprising the first combination;

providing the plurality of brightfield images and the plurality of fluorescent images to a trained model;

distinguishing the one or more cancer organoid cells from the one or more immune cells within the plurality of fluorescent images by:

using the trained model, generating from the plurality of brightfield images a plurality of masking images of segmented organoids;

applying the plurality of masking images to the plurality of fluorescent images to identify the segmented organoids in the plurality of fluorescent images;

characterizing a response of the one or more cancer organoid cells to the one or more immune cells by comparing at least one of the plurality of fluorescent images to another one of the plurality of fluorescent images;
and generating an analytical report including the cancer organoid response to the immune cell based therapy, wherein the analytical report includes a characterization of (i) cancer organoid morphology change over time caused by the immune cell based therapy and/or (ii) cell death caused by the immune cell based therapy.

2. The method of claim 1, further comprising:

performing a stacking process on the plurality of fluorescent images to generate flattened fluorescent images of organoids within the first culturing well for each different time point; and wherein providing the plurality of fluorescent images to the trained model comprises providing the flattened fluorescent images to the trained model.

3. The method of claim 1, wherein the plurality of fluorescent images are three-dimensional (3D) fluorescence images, the method further comprising:

performing a flattening process on the 3D fluorescence images to generate 2D fluorescence images of the first combination within the first culturing well for each different time point; and wherein providing the plurality of fluorescent images to the trained model comprises providing the 2D fluorescence images to the trained model.

4. The method of claim 1, wherein the plurality of fluorescent images are three-dimensional (3D) fluorescence images, the method further comprising:

performing a slice on the 3D fluorescence images to generate 2D fluorescence images of the first combination within the first culturing well for each different time point; and wherein providing the plurality of fluorescent images to the trained model comprises providing the 2D fluorescence images to the trained model.

5. The method of claim 1, further comprising, prior to providing the first combination of the one or more cancer organoid cells and the one or more immune cells to the first culturing well:

selecting the first combination of the one or more cancer organoid cells and the one or more immune cells based on cancer cell characteristics and the immune cell based therapy.

6. The method of claim 1, further comprising:

providing a second combination of the one or more cancer organoid cells and the one or more immune cells to a second culturing well, wherein the second combination represents a different concentration of the one or more cancer organoid cells to the one or more immune cells than the first combination.

7. The method of claim 6, wherein generating the analytical report comprises:

providing a comparison of immune cell based therapy efficacies between the first combination and the second combination.

8. The method of claim 1, wherein characterizing the cancer organoid morphology change caused by the immune cell based therapy comprises: characterizing cell death, cytokine secretion, and/or a shape change.

9. The method of claim 1, wherein characterizing the cancer organoid morphology change comprises: quantifying a number of cancer organoid cell deaths corresponding to each respective periodic capture of the plurality of bright-field images and the corresponding plurality of fluorescent images.

10. The method of claim 1, wherein characterizing the cancer organoid morphology change comprises:
determining (i) a number and/or percentage of the one or more cancer organoid cells undergoing a phenotypic change over the different time points, (ii) proliferation of the one or more cancer organoid cells over the different time points, and/or (iii) a change in morphology of the one or more cancer organoid cells over the different time points.

11. The method of claim 1, further comprising:
identifying, using the trained model, the one or more cancer organoid cells that are surrounded by the one or more immune cells;
identifying, using the trained model, a spatial relationship between the one or more cancer organoid cells resistant to the immune cell based therapy;
characterizing, using the trained model, migration and/or chemotaxis of the one or more immune cells, and/or
characterizing, using the trained model, co-localization of the one or more immune cells and the one or more cancer organoid cells.

12. The method of claim 1, further comprising:
quantifying a number of immune cell deaths in each of the plurality of brightfield images using the corresponding plurality of fluorescent images.

13. The method of claim 1, wherein the trained model comprises an organoid trained segmentation model for identifying cancer organoid cells in the plurality of brightfield images.

14. The method of claim 1, wherein the trained model comprises an immune cell trained segmentation model for identifying immune cells in the plurality of brightfield images.

15. The method of claim 1, wherein identifying and distinguishing the cultured cancer organoid cells and/or the cultured immune cells comprises:
using the trained model, generating from the plurality of brightfield images a second plurality of masking images of the one or more immune cells or a combination of the one or more cancer organoid cells and the one or more immune cells.

16. The method of claim 1, wherein the plurality of masking images comprises a binary mask of segmented cancer organoid cells.

17. The method of claim 15, wherein the second plurality of masking images comprises a binary mask of the one or more immune cells.

18. The method of claim 15, wherein the plurality of masking images comprise a categorical mask differentiating between the one or more cancer organoid cells and one or more types of immune cells, and wherein the categorical mask comprising a plurality of boundary types, each identifying a different one of the one or more cancer organoid cells and the one or more types of immune cells.

19. The method of claim 1, wherein the trained model comprises a machine learning algorithm trained using a plurality of training images, wherein at least some of the plurality of training images include annotations identifying one or more of organoid targets, organoids of different morphology, organoids of different locations, and organoids generated by different culturing methods.

20. The method of claim 1, wherein the trained model comprises a machine learning algorithm trained using a plurality of training images, wherein at least some of the plurality of training images include annotations identifying one or more of fluorescence dye regions, different cell types, immune cell therapies, and degrees of immune cell therapy response.

21. The method of claim 15, wherein the trained model comprises a machine learning algorithm trained using a plurality of training images, wherein the plurality of training images are obtained from a pre-trained segmentation model, and wherein the pre-trained segmentation model removed the one or more cancer organoid cells, leaving the one or more immune cells.

22. The method of claim 1, wherein the trained model comprises a machine learning algorithm trained using a plurality of training images, wherein the plurality of training images are obtained from a pre-trained segmentation model, and wherein the pre-trained segmentation model removed the one or more immune cells, leaving the one or more cancer organoid cells.

23. The method of claim 1, wherein the trained model comprises a machine learning algorithm trained using a plurality of training images obtained from a pre-trained segmentation model that is segmented out from a series of input images of the one or more immune cells and the one or more cancer organoid cells.

24. The method of claim 1, wherein the trained model comprises a segmentation model trained to detect the one or more cancer organoid cells and having a first machine learning algorithm trained using a plurality of training images.

25. The method of claim 15, wherein the trained model comprises a segmentation model trained to detect immune cells and having a first machine learning algorithm trained using a plurality of training images and a plurality of corresponding training fluorescence images having the one or more immune cells labeled.

26. The method of claim 1, wherein generating the analytical report comprises:
generating a time-lapse imaging of the one or more cancer organoid cells and/or the one or more immune cells at the different time points to identify cell death.

27. The method of claim 1, wherein generating the analytical report comprises:
identifying the one or more cancer organoid cells resistant to the immune cell based therapy and/or identifying the one or more cancer organoid cells susceptible to the immune cell based therapy based on changes in the one or more cancer organoid cells over the different time points.

28. The method of claim 1, wherein the analytical report further includes a structured file of intensity values, pixel location, size, index, and/or death of the one or more cancer organoid cells within the plurality of brightfield images and the corresponding plurality of fluorescent images.

29. The method of claim 1, further comprising: applying an intensity normalization process to each of the plurality of fluorescent images by determining a background intensity of each respective image and normalizing the background intensity by subtracting the background intensity from each respective image.

30. The method of claim 1, wherein providing the plurality of brightfield images and the plurality of fluorescent images to the trained model comprises: combining the plurality of brightfield images and the plurality of fluorescent images into one or more multi-channel images to be provided to the trained model.

31. The method of claim 1, further comprising: quantifying metabolic activity of the one or more cancer organoid cells and/or the one or more immune cells.

32. The method of claim 1, further comprising:

characterizing a presence or amount of one or more biomarkers; and generating the analytical report to further include the characterized presence or amount of the one or more biomarkers.

33. The method of claim 1, further comprising:

quantifying a proportion of specific cell types from the first combination of the one or more cancer organoid cells and the one or more immune cells using fluorescence-activated cell sorting (FACS); and generating the analytical report to further include the quantified proportion of specific cell types.

34. The method of claim 1, wherein the one or more immune cells are peripheral blood mononuclear cells (PBMCs).

35. The method of claim 1, wherein the one or more immune cells are lymphocytes, monocytes, and/or dendritic cells.

36. The method of claim 1, wherein the one or more immune cells are T cells and/or natural killer (NK) cells.

37. The method of claim 1, wherein the one or more immune cells are neutrophils, eosinophils, basophils, and/or macrophages.

38. The method of claim 1, wherein the one or more cancer organoid cells are derived from at least one of anal cancer, a basal cell skin cancer, a squamous cancer, a benign cancer, a brain cancer, a glioblastoma, a breast cancer, a bladder cancer, a cervical cancer, a colon cancer, a colorectal cancer, an endometrial cancer, an esophageal cancer, a head and neck cancer, a liver cancer, a hepatobiliary cancer, a kidney cancer, a renal cancer, a gastric cancer, a gastrointestinal cancer, a lung cancer, a non-small cell lung cancer (NSCLC), a mesothelial cancer of the pleural cavity, a mesothelioma, an ovarian cancer, a pancreatic cancer, a prostate cancer, a rectal cancer, a lymphoma, a melanoma, a skin cancer, a meningioma, a sarcoma, and a thymus cancer.

\* \* \* \* \*